United States Patent
Dimitrov et al.

(10) Patent No.: US 9,598,492 B2
(45) Date of Patent: Mar. 21, 2017

(54) HUMAN MONOCLONAL ANTIBODIES SPECIFIC FOR CD22

(71) Applicant: The United States of America as represented by the Secretary of the Department of Health and Human Services, Washington, DC (US)

(72) Inventors: Dimiter S. Dimitrov, Frederick, MD (US); Xiaodong Xiao, Frederick, MD (US); Ira H. Pastan, Potomac, MD (US)

(73) Assignee: The United States of America as represented by the Secretary of the Department of Health and Human Services, Washington, DC (US)

( * ) Notice: Subject to any disclaimer, the term of this patent is extended or adjusted under 35 U.S.C. 154(b) by 0 days.

(21) Appl. No.: 15/012,023

(22) Filed: Feb. 1, 2016

(65) Prior Publication Data

US 2016/0145338 A1     May 26, 2016

Related U.S. Application Data

(62) Division of application No. 13/959,061, filed on Aug. 5, 2013, now Pat. No. 9,279,019, which is a division of application No. 12/934,214, filed as application No. PCT/US2009/039080 on Apr. 1, 2009, now Pat. No. 8,591,889.

(60) Provisional application No. 61/042,329, filed on Apr. 4, 2008.

(51) Int. Cl.

| | |
|---|---|
| *A61K 39/395* | (2006.01) |
| *C07K 16/28* | (2006.01) |
| *A61K 38/16* | (2006.01) |
| *A61K 47/48* | (2006.01) |
| *A61K 39/00* | (2006.01) |

(52) U.S. Cl.
CPC ........ *C07K 16/2803* (2013.01); *A61K 38/164* (2013.01); *A61K 47/4863* (2013.01); *A61K 47/48484* (2013.01); *C07K 16/2896* (2013.01); *A61K 39/00* (2013.01); *A61K 39/39558* (2013.01); *A61K 2039/505* (2013.01); *C07K 16/28* (2013.01); *C07K 2317/21* (2013.01); *C07K 2317/51* (2013.01); *C07K 2317/515* (2013.01); *C07K 2317/55* (2013.01); *C07K 2317/565* (2013.01); *C07K 2317/622* (2013.01); *C07K 2317/92* (2013.01)

(58) Field of Classification Search
CPC .................. A61K 39/39558; A61K 2039/505
See application file for complete search history.

(56) References Cited

U.S. PATENT DOCUMENTS

| | | | |
|---|---|---|---|
| 5,789,650 | A | 8/1998 | Lonberg et al. |
| 5,798,230 | A | 8/1998 | Bornkamm et al. |
| 6,146,894 | A | 11/2000 | Nicolaides et al. |
| 2004/0192900 | A1 | 9/2004 | Kunz et al. |
| 2005/0118182 | A1 | 6/2005 | Pastan et al. |
| 2005/0123900 | A1 | 6/2005 | Dimitrov et al. |
| 2005/0244828 | A1 | 11/2005 | Kreitman et al. |
| 2006/0057136 | A1 | 3/2006 | Goldenberg |
| 2007/0003556 | A1 | 1/2007 | Tsuchiya et al. |
| 2007/0189962 | A1 | 8/2007 | Pastan et al. |
| 2007/0258981 | A1 | 11/2007 | Hilbert et al. |
| 2007/0264260 | A1 | 11/2007 | Tuscano et al. |

FOREIGN PATENT DOCUMENTS

| | | |
|---|---|---|
| WO | WO 96/33735 | 10/1996 |
| WO | WO 96/34096 | 10/1996 |
| WO | WO 98/41641 | 9/1998 |
| WO | WO 03/027135 | 4/2003 |
| WO | WO 03/093320 | 11/2003 |
| WO | WO 2007/048077 | 4/2007 |
| WO | WO 2007/103469 | 9/2007 |
| WO | WO 2007/103470 | 9/2007 |
| WO | WO 2007/140371 | 12/2007 |
| WO | WO 2008/070569 | 6/2008 |

OTHER PUBLICATIONS

Henry et al. (Cancer Res. Nov. 1, 2004; 64: 7995-8001).*
McDevitt et al. (Cancer Res. Nov. 1, 2000; 60: 6095-6100).*
Takeshita et al. (Leukemia. Jul. 2009; 23 (7): 1329-36).*
Pettersen et al. (J. Immunol. Jun. 15, 1999; 162 (12): 7031-7040).*
Bernard et al. (Human Immunol. 1986; 17: 388-405).*
Jiang et al. (J. Biol. Chem. Feb. 11, 2005; 280 (6): 4656-4662).*
Stancovski et al. (Proceedings of the National Academy of Science USA. 1991; 88: 8691-8695).*
Campbell et al (Blood Rev. 2003; 17: 143-152).*
Kipps et al. (J. Exp. Med. Jan. 1, 1985; 161 (1): 1-17).*
Arons et al. "Minimal Residual Disease in Hairy Cell Leukemia Patients Assessed by Clone-Specific Polymerase Chain Reaction," *Clinical Cancer Research* 12(9):2804-2811, May 1, 2006.
Bang et al. "HA22 (R490A) Is a Recombinant Immunotoxin with Increased Antitumor Activity without an Increase in Animal Toxicity," *Clinical Cancer Research* 11:1545-1550, Feb. 15, 2005.

(Continued)

*Primary Examiner* — Stephen Rawlings
(74) *Attorney, Agent, or Firm* — Klarquist Sparkman, LLP

(57) ABSTRACT

Disclosed herein are isolated human monoclonal antibodies that specifically bind human CD22 with a dissociation constant ($K_d$) of 25 nM or less. Nucleic acids encoding these antibodies, expression vectors including these nucleic acid molecules, and isolated host cells that express the nucleic acid molecules are also disclosed. The antibodies can be used to detect human CD22 in a sample. In some cases, CD22 is soluble CD22. Methods of diagnosing a B-cell malignancy, or confirming a B-cell malignancy diagnosis, are disclosed herein that utilize these antibodies. Methods of treating a subject with a B-cell malignancy are also disclosed.

13 Claims, 10 Drawing Sheets

(56) References Cited

OTHER PUBLICATIONS

Bernard et al, A Unique Epitope on the CD2 Molecule Defined by the Monoclonal Antibody 9-1: Epitope-Specific Modulation of the E-Rosette Receptor and Effects on T-Cell Functions, *Human Immunol.*, vol. 17:388-405, 1986.
Boyer et al., "Relative Cytotoxic Activity of Immunotoxins Reactive with Different Epitopes on the Extracellular Domain of the c-erbB-2 (HER-2/neu) Gene Product p185," *Int. J. Cancer*, vol. 82:525-531, 1999.
Caldas et al., "Humanization of the Anti-CD18 Antibody 6.7: An Unexpected Effect of a Framework Residue in Binding to Antigen," *Mol. Immunol.*, vol. 39:941-952, 2003.
Campbell et al., "Monoclonal Antibody Therapy for Lymphoma," *Blood Rev.*, vol. 17:143-152, 2003.
Casset et al., "A Peptide Mimetic of an Anti-CD4 Monoclonal Antibody by Rational Design," *Biochem. Biophys. Res. Commun.*, vol. 307:198-205, 2003.
Chien et al., "Significant Structural and Functional Change of an Antigen-Binding Site by a Distant Amino Acid Substitution: Proposal of a Structural Mechanism," *Proc. Natl. Acad. Sci. USA*, vol. 86:5532-5536, 1989.
Damle et al., "B-cell Chronic Lymphocytic Leukemia Cells Express a Surface Membrane Phenotype of Activated, Antigen-Experienced B Lymphocytes: Presented in part of the 42$^{nd}$ Annual Meeting of the American Society of Hematology, Dec. 1, 2000, San Francisco, CA," *Blood*, vol. 99:4087-4093, 2002.
Decker et al. "Induction of caspase-dependent programmed cell death in B-cell chronic lymphocytic leukemia by anti-CD22 immunotoxins," *Blood* 103:2718-2726, Oct. 2, 2003.
Decker et al. "Sensitization of B-cell chronic lymphocytic leukemia cells to recombinant immunotoxin by immunostimulatory phosphorothioate oligodeoxynucleotides," *Blood* 99(4):1320-1326, 2002.
De Pascalis et al., "Grafting of "Abbreviated" Complementarity-Determining Regions Containing Specificity-Determining Residues Essential for Ligand Contact to Engineer a Less Immunogenic Humanized Monoclonal Antibody," *J. Immunol.*, vol. 169:3076-3084, 2002.
DiJoseph et al. "Antitumor Efficacy of a Combination of CMC-544 (Inotuzumab Ozogamicin), a CD22-Targeted Cytotoxic Immunoconjugate of Calicheamicin, and Rituximab against Non-Hodgkin's B-Cell Lymphoma," *Clinical Cancer Research.* 12(1):242-249, Jan. 1, 2006.
Giusti et al., "Somatic Diversification of S107 from an Antiphosphocholine to an Anti-DNA Autoantibody is due to a Single Base Change in its Heavy Chain Variable Region," *Proc. Natl. Acad. Sci. USA*, vol. 84:2926-2930, 1987.
Güssow et al., "Humanization and Monoclonal Antibodies," *Methods Enzymol.*, vol. 203: 99-121, 1991.
Henry et al., "A Prostate-Specific Membrane Antigen-Targeted Monoclonal Antibody-Chemotherapeutic Conjugate Designed for the Treatment of Prostate Cancer," *Cancer Res.*, vol. 64:7995-8001, 2004.
Ho et al. "Isolation of anti-CD22 Fv with high affinity by Fv display on human cells," *PNAS* 103(25):9637-9642, Jun. 20, 2006.
Ho et al. "In Vitro Antibody Evolution Targeting Germline Hot Spots to Increase Activity of an Anti-CD22 Immunotoxin," *The Journal of Biological Chemistry* 280(1):607-617, 2005.
Holm et al., Functional Mapping and Single Chain Construction of the Anti-Cytokeratin 8 Monoclonal Antibody TS1, *Mol. Immunol.*, vol. 44:1075-1084, 2007.
Jiang et al., "A Novel Peptide Isolated from a Phage Display Peptide Library with Trastuzumab Can Mimic Antigen Epitope of HER-2," *J. Biol. Chem.*, vol. 280(6):4656-4662, 2005.
Kim et al., "Both the Epitope Specificity and Isotype are Important in the Antitumor Effect of Monoclonal Antibodies Against HER-2/NEU Antigen," *Int. J. Cancer*, vol. 102:428-434, 2002.

Kipps et al., "Importance of Immunoglobulin Isotype in Human Antibody-Dependent, Cell-Mediated Cytotoxicity Directed by Murine Monoclonal Antibodies," *J. Exp. Med.*, vol. 161:1-17, 1985.
Kreitman et al. "Efficacy of the Anti-CD22 Recombinant Immunotoxin BL22 in Chemotherapy-Resistant Hairy-Cell Leukemia," *New England Journal of Medicine* 345(4):241-247, Jul. 26, 2001.
Kreitman et al. "Cytotoxic Activity of Disulfide-stabilized Recombinant Immunotoxin RFB4(dsFv)-PE38 (BL22) toward Fresh Malignant Cells from Patients with B-Cell Leukemias," *Clinical Cancer Research* 6:1476-1487, Apr. 2000.
Leonard et al. "Epratuzumab, a Humanized Anti-CD22 Antibody, in Aggressive Non-Hodgkin's Lymphoma: Phase I/II Clinical Trial Results," *Clinical Cancer Research* 10:5327-5334, Aug. 15, 2004.
Lewis et al., "Differential Responses of Human Tumor Cell Lines to Anti-p185$^{HER2}$ Monoclonal Antibodies," *Cancer Immunol. Immunother.*, vol. 37:255-263, 1993.
Li et al. "Human antibodies for immunotherapy development generated via a human B cell hybridoma technology," *PNAS* 103(10):3557-3562, Mar. 7, 2006.
Li et al. "Eradication of Tumor Colonization and Invasion by a B Cell-Specific Immunotoxin in a Murine Model for Human Primary Intraocular Lymphoma," *Cancer Research* 66(21):10586-10593, Nov. 1, 2006.
MacCallum et al., "Antibody-Antigen Interactions: Contact Analysis and Binding Site Topography," *J. Mol. Biol.*, vol. 262:732-745, 1996.
Mansfield et al. "Recombinant RFB4 Immunotoxins Exhibit Potent Cytotoxic Activity for CD22-Bearing Cells and Tumors," *Blood* 90:2020-2026, 1997.
Mariuzza et al., "The Structural Basis of Antigen-Antibody Recognition," *Ann. Rev. Biophys. Biophys. Chem.*, vol. 16:139-159, 1987.
Masui et al., "Mechanism of Antitumor Activity in Mice for Anti-Epidermal Growth Factor Receptor Monoclonal Antibodies with Different Isotypes," *Cancer Res.*, vol. 46:5592-5598, 1986.
Matsushita et al., "Soluble CD22 as a Tumor Marker for Hairy Cell Leukemia," *Blood*, vol. 112:2272-2277, 2008.
McDevitt et al., "An α-Particle Emitting Antibody ([$^{213}$Bi]J591) for Radioimmunotherapy of Prostate Cancer," *Cancer Res.*, vol. 60:6095-6100, 2000.
Onda et al. "Lowering the Isoelectric Point of the Fv Portion of Recombinant Immunotoxins Leads to Decreased Nonspecific Animal Toxicity without Affecting Antitumor Activity," *Cancer Research* 61:5070-5077, Jul. 1, 2001.
Pettersen et al., "CD47 Signals T Cell Death," *J. Immunol.*, vol. 162:7031-7040, 1999.
Press et al., "Ricin A-Chain Containing Immunotoxins Directed Against Different Epitopes on the CD2 Molecule Differ in their Ability to Kill Normal and Malignant T Cells," *J. Immunol.*, vol. 141:4410-4417, 1988.
Riemer et al., "Matching of Trastuzumab (Herceptin®) Epitope Mimics onto the Surface of Her-2/neu—A New Method of Epitope Definition," *Mol. Immunol.*, vol. 42:1121-1124, 2005.
Rothe et al. "Ribosome display and selection of human anti-CD22 scFvs derived from an acute lymphocytic leukemia patient," *Biological Chemistry* 389(4):433-439, Apr. 2008.
Rudikoff et al., "Single Amino Acid Substitution Altering Antigen-Binding Specificity," *Proc. Natl. Acad. Sci. USA*, vol. 79:1979-1983, 1982.
Salvatore et al. "Improved Cytotoxic Activity toward Cell Lines and Fresh Leukemia Cells of a Mutant Anti-CD22 Immunotoxin Obtained by Antibody Phage Display," *Clinical Cancer Research* 8:995-1002, Apr. 2002.
Stancovski et al., "Mechanistic Aspects of the Opposing Effects of Monoclonal Antibodies to the ERBB2 Receptor on Tumor Growth," *Proc. Natl. Acad. Sci. USA*, vol. 88:8691-8695, 1991.
Takeshita et al., CMC-544 (inotuzumab ozogamicin), An Anti-CD22 Immuno-Conjugate of Calicheamicin, Alters the Levels of Target Molecules of Malignant B-Cells, *Leukemia*, vol. 23:1329-1336, 2009.
Tedder et al. "CD22, A B Lymphocyte-Specific Adhesion Molecule That Regulates Antigen Receptor Signaling," *Annu. Rev. Immunol* 15:481-504, 1997.

(56) References Cited

OTHER PUBLICATIONS

Vajdos et al., "Comprehensive Functional Maps of the Antigen-Binding Site of an Anti-ErbB2 Antibody Obtained with Shotgun Scanning Mutagenesis," *J. Mol. Biol.*, vol. 320:415-428, 2002.

Vuist et al., "Two Distinct Mechanisms of Antitumor Activity Mediated by the Combination of Interleukin 2 and Monoclonal Antibodies," *Cancer Res.*, vol. 50:5767-5772, 1990.

Wark et al. "Latest technologies for the enhancement of antibody affinity," *Advanced Drug Delivery Reviews* 58(5-6):657-670, Aug. 7, 2006.

Winkler et al., "Changing the Antigen Binding Specificity by Single Point Mutations of an Anti-24 (HIV-1) Antibody," *J. Immunol.*, vol. 165:4505-4514, 2000.

Wu et al., "Humanization of a Murine Monoclonal Antibody by Simultaneous Optimization of Framework and CDR Residues," *J. Mol. Biol.*, vol. 294:151-162, 1999.

International Search Report and Written Opinion of corresponding PCT Application No. PCT/US2009/039080 dated Jul. 8, 2009.

\* cited by examiner

HUMAN MONOCLONAL ANTIBODIES SPECIFIC FOR CD22

CROSS REFERENCE TO RELATED APPLICATIONS

This is a divisional of U.S. patent application Ser. No. 13/959,061, filed Aug. 5, 2013, issued as U.S. Pat. No. 9,279,019 on Mar. 8, 2016, which is a divisional of U.S. application Ser. No. 12/934,214, filed Sep. 23, 2010, issued as U.S. Pat. No. 8,591,889, on Nov. 26, 2013 which is the U.S. National Stage of International Application No. PCT/US2009/039080, filed Apr. 1, 2009, published in English under PCT Article 21(2), which claims the benefit of U.S. Provisional Application No. 61/042,329, filed Apr. 4, 2008. All of the above-listed applications are herein incorporated by reference in their entirety.

FIELD

This disclosure relates to monoclonal antibodies, particularly human monoclonal antibodies that specifically bind CD22, and their use.

BACKGROUND

CD22 is a 135 kDa sialoglycoprotein expressed on the surface of B-cells at the mature stages of cell differentiation (Dorken et al., *J. Immunol.* 136:4470-4479, 1986). CD22 functions in B-cell activation and as an adhesion molecule, mediating interactions with activated blood cells and accessory cells (Hanasaki et al., *J. Biol. Chem.* 270(13):7533-7542, 1995). CD22 is not found on the surface of B cells during the early stages of development, nor is it expressed in stem cells. However, 60-70% of all B-cell lymphomas and leukemias express CD22.

Expression of CD22 in a number of B-cell malignancies has made CD22 an attractive target for immunotherapy. For example, Epratuzumab, a humanized anti-CD22 antibody has been evaluated in patients with aggressive non-Hodgkin's lymphoma (Leonard et al., *Clin. Cancer Res.* 10:5327-5334, 2004). Immunoconjugates including chimeric (humanized) anti-CD22 antibodies have also been studied, such as CMC-544 (DiJoseph et al., *Clin. Cancer Res.* 12(1):242-249, 2006). An anti-CD22 immunotoxin BL22, a mouse anti-CD22 antibody linked to *Pseudomonas* exotoxin PE38, has been evaluated for efficacy in the treatment of hairy cell leukemia (Kreitman et al., *N. Engl. J. Med.* 345(4):241-247; U.S. Patent Application Publication Nos. 2005/0118182 and 2007/0189962).

CD22-specific antibodies have potential as cancer therapeutic and diagnostic reagents. However, a major limitation in the clinical use of mouse monoclonal antibodies is the development of a human anti-murine antibody (HAMA) response. The HAMA response can involve allergic reactions and an increased rate of clearance of the administered antibody from the serum. A need remains for fully human antibodies that specifically bind CD22 with high affinity, which can be used in the diagnosis and treatment of cancer, particularly in the treatment of B-cell malignancies. However, it is difficult to produce fully human antibodies to human antigens, as these antigens are generally recognized as self antigens.

SUMMARY

Isolated human monoclonal antibodies specific for human CD22 are provided herein. The human monoclonal antibodies bind CD22 with a dissociation constant ($K_d$) of about 25 nM or less. In some embodiments, the $K_d$ is about 2 to about 20 nM. In some examples, the $K_d$ is about 20 nM. In other examples, the $K_d$ is about 2 nM. Further provided are compositions including the CD22-specific antibodies, nucleic acids encoding these antibodies, expression vectors comprising the nucleic acids, and isolated host cells that express the nucleic acids.

Also provided are immunoconjugates comprising the human monoclonal antibodies specific for human CD22. Compositions comprising the immunoconjugates are also provided.

The antibodies and compositions provided herein can be used for a variety of purposes, such as for diagnosing and for confirming the diagnosis of a B-cell malignancy in a subject. Thus, provided herein is a method of confirming the diagnosis of a B-cell malignancy in a subject, comprising contacting a sample from the subject diagnosed with a B-cell malignancy with a human monoclonal antibody that specifically binds CD22, and detecting binding of the antibody to the sample. An increase in binding of the antibody to the sample relative to binding of the antibody to a control sample confirms the B-cell malignancy diagnosis. In some examples, the antibody binds soluble CD22 in the sample. In some embodiments, the methods further comprise contacting a second antibody that specifically recognizes the CD22-specific antibody with the sample, and detecting binding of the second antibody.

Similarly, provided herein is a method of detecting a B-cell malignancy in a subject, comprising contacting a sample from the subject with a human monoclonal antibody that specifically binds CD22, and detecting binding of the antibody to the sample. An increase in binding of the antibody to the sample relative to a control sample detects a B-cell malignancy in the subject. In some examples, the antibody binds soluble CD22 in the sample. In some embodiments, the methods further comprise contacting a second antibody that specifically recognizes the CD22-specific antibody with the sample, and detecting binding of the second antibody.

Further provided is a method of treating a subject diagnosed with a B-cell malignancy, comprising administering a therapeutically effective amount of a human CD22-specific monoclonal antibody, or an immunoconjugate comprising the antibody, to the subject.

The foregoing and other features and advantages will become more apparent from the following detailed description of several embodiments, which proceeds with reference to the accompanying figures.

BRIEF DESCRIPTION OF THE FIGURES

In FIG. 1D, m972 scFv was tested in comparison to the established CD22-specific HA22 scFv.

(FIG. 4A) Increasing concentrations of both IgG1 m971 and IgG1 m972 were incubated with BJAB cells in a flow cytometry assay as described in Example 1 below. (FIG. 4B) The median fluorescence intensities from flow cytometry were plotted against the corresponding concentrations used for IgG1 m971 and IgG1 m972.

SEQUENCE LISTING

Figure 1A:
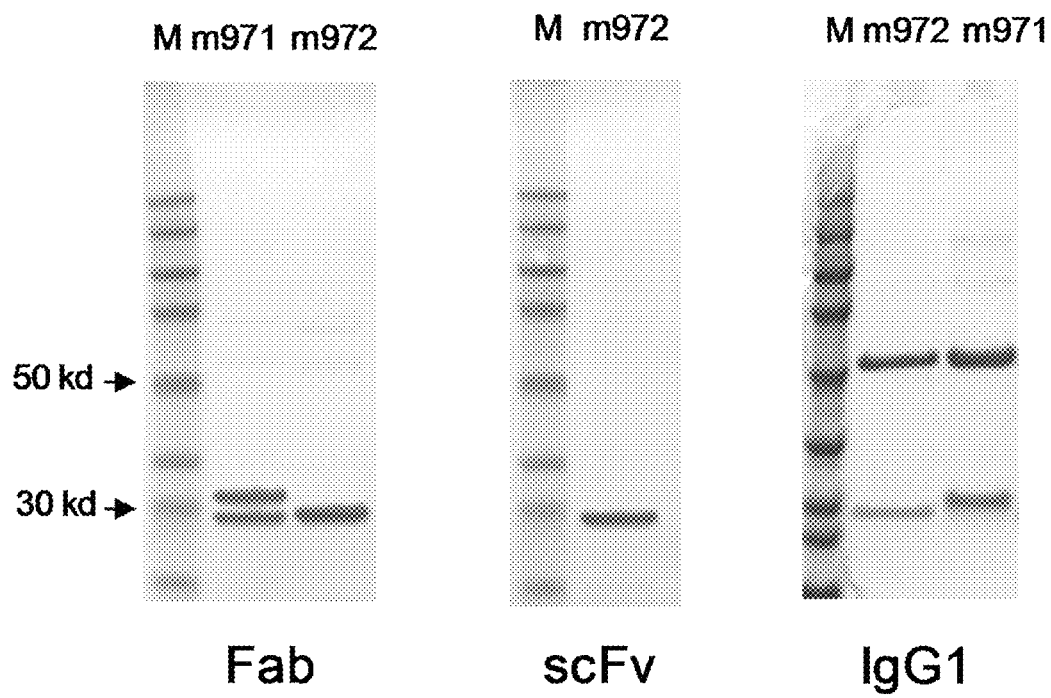
FIG. 1A is a series of digital images of electrophoretic gels of m971 and m972 in Fab, scFv and IgG1 formats. Antibodies in the indicated formats were run on 4-12% gradient SDS-PAGE gels under reducing conditions and stained with Coomassie blue. The heavy and light chains of m971 have a different molecular weight, whereas the heavy and light chains of m972 ran at the same position. M=molecular weight marker.

The nucleic and amino acid sequences listed in the accompanying sequence listing are shown using standard letter abbreviations for nucleotide bases, and three letter code for amino acids, as defined in 37 C.F.R. 1.822. Only one strand of each nucleic acid sequence is shown, but the complementary strand is understood as included by any reference to the displayed strand. The Sequence Listing is submitted as an ASCII text file, created on Jan. 28, 2016, 32.7 KB, which is incorporated by reference herein. In the accompanying sequence listing:

SEQ ID NO: 1 is the amino acid sequence of the heavy chain of CD22-specific antibody m972.

SEQ ID NO: 2 is the amino acid sequence of the light chain of CD22-specific antibody m972.

SEQ ID NO: 3 is the amino acid sequence of the heavy chain of CD22-specific antibody m971.

SEQ ID NO: 4 is the amino acid sequence of the light chain of CD22-specific antibody m971.

SEQ ID NOs: 5 and 6 are the nucleotide and amino acid sequences, respectively, of human CD22, deposited under GENBANK™ Accession No. NM_001771 on Sep. 13, 2007.

SEQ ID NO: 7 is the nucleotide sequence encoding the heavy chain of CD22-specific antibody m972.

SEQ ID NO: 8 is the nucleotide sequence encoding the light chain of CD22-specific antibody m972.

SEQ ID NO: 9 is the nucleotide sequence encoding the heavy chain of CD22-specific antibody m971.

SEQ ID NO: 10 is the nucleotide sequence encoding the light chain of CD22-specific antibody m971.

SEQ ID NO: 11 is the amino acid sequence of a peptide linker.

DETAILED DESCRIPTION

I. Abbreviations

3SR: Self-sustained sequence replication
ADCC: Antibody-dependent cell-mediated cytotoxicity
CDR: Complementarity determining region
CLL: Chronic lymphocytic leukemia
DT: Diphtheria toxin
ELISA: Enzyme-linked immunosorbent assay
EM: Effector molecule
FACS: Fluorescence-activated cell sorting
FBS: Fetal bovine serum
FITC: Fluorescein isothiocyanate
HCL: Hairy cell leukemia
HRP: Horseradish peroxidase
Ig: Immunoglobulin
LCR: Ligase chain reaction
LDH: Lactate dehydrogenase
NHL: Non-Hodgkin's lymphoma
mAb: Monoclonal antibody
MALT: Mucosa-associated lymphoid tissue
MPBS: Milk/PBS
PAGE: Polyacrylamide gel electrophoresis
PBMC: Peripheral blood mononuclear cells
PBS: Phosphate-buffered saline
PBST: PBS-Tween 20
PCR: Polymerase chain reaction
PE: *Pseudomonas* exotoxin
RIA: Radioimmunoassay
sCD22: Soluble CD22
SDS: Sodium dodecyl sulfate II. Terms Unless otherwise noted, technical terms are used according to conventional usage. Definitions of common terms in molecular biology may be found in Benjamin Lewin, *Genes V*, published by Oxford University Press, 1994 (ISBN 0-19-854287-9); Kendrew et al. (eds.), *The Encyclopedia of Molecular Biology*, published by Blackwell Science Ltd., 1994 (ISBN 0-632-02182-9); and Robert A. Meyers (ed.), *Molecular Biology and Biotechnology: a Comprehensive Desk Reference*, published by VCH Publishers, Inc., 1995 (ISBN 1-56081-569-8).

In order to facilitate review of the various embodiments of the disclosure, the following explanations of specific terms are provided:

Animal: Living multi-cellular vertebrate organisms, a category that includes, for example, mammals and birds. The term mammal includes both human and non-human mammals. Similarly, the term "subject" includes both human and veterinary subjects.

Antibody: A polypeptide ligand comprising at least a light chain or heavy chain immunoglobulin variable region which specifically recognizes and binds an epitope of an antigen, such as CD22 or a fragment thereof. Antibodies are composed of a heavy and a light chain, each of which has a variable region, termed the variable heavy ($V_H$) region and the variable light ($V_L$) region. Together, the $V_H$ region and the $V_L$ region are responsible for binding the antigen recognized by the antibody.

Antibodies include intact immunoglobulins and the variants and portions of antibodies well known in the art, such as Fab fragments, Fab' fragments, F(ab)'2 fragments, single chain Fv proteins ("scFv"), and disulfide stabilized Fv proteins ("dsFv"). A scFv protein is a fusion protein in which a light chain variable region of an immunoglobulin and a heavy chain variable region of an immunoglobulin are bound by a linker, while in dsFvs, the chains have been mutated to introduce a disulfide bond to stabilize the association of the chains. The term also includes genetically engineered forms such as chimeric antibodies (for example, humanized murine antibodies), heteroconjugate antibodies (such as, bispecific antibodies). See also, *Pierce Catalog and Handbook*, 1994-1995 (Pierce Chemical Co., Rockford, Ill.); Kuby, J., *Immunology*, $3^{rd}$ Ed., W. H. Freeman & Co., New York, 1997.

Typically, a naturally occurring immunoglobulin has heavy (H) chains and light (L) chains interconnected by disulfide bonds. There are two types of light chain, lambda (λ) and kappa (k). There are five main heavy chain classes (or isotypes) which determine the functional activity of an antibody molecule: IgM, IgD, IgG, IgA and IgE.

Each heavy and light chain contains a constant region and a variable region, (the regions are also known as "domains"). In combination, the heavy and the light chain variable regions specifically bind the antigen. Light and heavy chain variable regions contain a "framework" region interrupted by three hypervariable regions, also called "complementarity-determining regions" or "CDRs." The extent of the framework region and CDRs have been defined (see, Kabat et al., *Sequences of Proteins of Immunological Interest*, U.S. Department of Health and Human Services, 1991). The Kabat database is now maintained online. The sequences of the framework regions of different light or heavy chains are relatively conserved within a species, such as humans. The framework region of an antibody, that is the combined framework regions of the constituent light and heavy chains, serves to position and align the CDRs in three-dimensional space.

The CDRs are primarily responsible for binding to an epitope of an antigen. The CDRs of each chain are typically referred to as CDR1, CDR2, and CDR3, numbered sequentially starting from the N-terminus, and are also typically identified by the chain in which the particular CDR is located. Thus, a $V_H$ CDR3 is located in the variable domain of the heavy chain of the antibody in which it is found, whereas a $V_L$ CDR1 is the CDR1 from the variable domain of the light chain of the antibody in which it is found. An antibody that binds CD22 will have a specific $V_H$ region and the $V_L$ region sequence, and thus specific CDR sequences.

Antibodies with different specificities (i.e. different combining sites for different antigens) have different CDRs. Although it is the CDRs that vary from antibody to antibody, only a limited number of amino acid positions within the CDRs are directly involved in antigen binding. These positions within the CDRs are called specificity determining residues (SDRs).

References to "$V_H$" or "VH" refer to the variable region of an immunoglobulin heavy chain, including that of an Fv, scFv, dsFv or Fab. References to "$V_L$" or "VL" refer to the variable region of an immunoglobulin light chain, including that of an Fv, scFv, dsFv or Fab.

A "monoclonal antibody" is an antibody produced by a single clone of B-lymphocytes or by a cell into which the light and heavy chain genes of a single antibody have been transfected. Monoclonal antibodies are produced by methods known to those of skill in the art, for instance by making hybrid antibody-forming cells from a fusion of myeloma cells with immune spleen cells. Monoclonal antibodies include humanized monoclonal antibodies.

A "chimeric antibody" has framework residues from one species, such as human, and CDRs (which generally confer antigen binding) from another species, such as a murine antibody that specifically binds CD22.

A "humanized" immunoglobulin is an immunoglobulin including a human framework region and one or more CDRs from a non-human (for example a mouse, rat, or synthetic) immunoglobulin. The non-human immunoglobulin providing the CDRs is termed a "donor," and the human immunoglobulin providing the framework is termed an "acceptor." In one embodiment, all the CDRs are from the donor immunoglobulin in a humanized immunoglobulin. Constant regions need not be present, but if they are, they must be substantially identical to human immunoglobulin constant regions, i.e., at least about 85-90%, such as about 95% or more identical. Hence, all parts of a humanized immunoglobulin, except the CDRs, are substantially identical to corresponding parts of natural human immunoglobulin sequences. A "humanized antibody" is an antibody comprising a humanized light chain and a humanized heavy chain immunoglobulin. A humanized antibody binds to the same antigen as the donor antibody that provides the CDRs. The acceptor framework of a humanized immunoglobulin or antibody may have a limited number of substitutions by amino acids taken from the donor framework. Humanized or other monoclonal antibodies can have additional conservative amino acid substitutions which have substantially no effect on antigen binding or other immunoglobulin functions. Humanized immunoglobulins can be constructed by means of genetic engineering (see for example, U.S. Pat. No. 5,585,089).

A "human" antibody (also called a "fully human" antibody) is an antibody that includes human framework regions and all of the CDRs from a human immunoglobulin. In one example, the framework and the CDRs are from the same originating human heavy and/or light chain amino acid sequence. However, frameworks from one human antibody can be engineered to include CDRs from a different human antibody. All parts of a human immunoglobulin are substantially identical to corresponding parts of natural human immunoglobulin sequences.

B-cell malignancy: As used herein "B-cell malignancy" includes any type of leukemia or lymphoma of B cells. B-cell malignancies include, but are not limited to, non-Hodgkin's lymphoma, Burkitt's lymphoma, small lymphocytic lymphoma, primary effusion lymphoma, diffuse large B-cell lymphoma, splenic marginal zone lymphoma, MALT (mucosa-associated lymphoid tissue) lymphoma, hairy cell leukemia, chronic lymphocytic leukemia and B-cell prolymphocytic leukemia.

Binding affinity: Affinity of an antibody for an antigen. In one embodiment, affinity is calculated by a modification of the Scatchard method described by Frankel et al. (*Mol. Immunol.*, 16:101-106, 1979). In another embodiment, binding affinity is measured by an antigen/antibody dissociation rate. In another embodiment, a high binding affinity is measured by a competition radioimmunoassay. In another embodiment, binding affinity's measured by ELISA. In one embodiment, the antibodies bind CD22 with a dissociation constant ($K_d$) of about 25 nM or less. In several embodiments, the human monoclonal antibodies bind human CD22 with a binding affinity of about 20 nM or less, about 19 nM or less, about 18 nM or less, about 17 nM or less, about 16 nM or less, or about 15 nM or less. In other embodiments, the human monoclonal antibodies bind human CD22 with a binding affinity of about 10 nM or less, about 9 nM or less, about 8 nM or less, about 7 nM or less, about 6 nM or less, or about 5 nM or less. In other embodiments, the human monoclonal antibodies bind human CD22 with a binding affinity of about 4 nM or less, about 3 nM or less, about 2.5 nM or less, about 2 nM or less, about 1.5 nM or less, or about 1 nM or less. In other embodiments, the human monoclonal antibodies bind human CD22 with a binding affinity of about 1 nM or less, about 0.75 nM or less, about 0.5 nM or less, about 0.25 nM or less, or about 0.1 nM or less. In one example, the binding affinity is about 20 nM. In another example, the binding affinity is about 2 nM. As used herein, a binding affinity of "about 20 nM" includes binding affinities of 19 to 21 nM. Similarly, a binding affinity of "about 2 nM" includes binding affinities of 1 nM to 3 nM.

Biological sample: A sample obtained from cells, tissue or bodily fluid of a subject, such as peripheral blood, cerebrospinal fluid, serum, bone marrow, urine, saliva, tissue biopsy, surgical specimen, amniocentesis samples and autopsy material. A biological sample is also referred to herein as a "sample."

Body fluid: Includes any bodily fluid from an animal, for instance blood, serum, semen, urine, cerebrospinal fluid or saliva.

CD22: A lineage-restricted B cell antigen belonging to the immunoglobulin superfamily. CD22 is expressed in 60-70% of B cell lymphomas and leukemias. CD22 is not present on the cell surface in the early stages of B cell development or on stem cells. As used herein "CD22" refers to a CD22 polypeptide or variant or fragment thereof. Sequences of human CD22 are known in the art (see, for example Torres et al., *J. Immunol.* 149(8):2641-2649, 1992; and Wilson et al., *J. Exp. Med.* 173(1):137-146, 1991). Exemplary CD22 nucleotide and amino acid sequences also are provided herein as SEQ ID NO: 5 and SEQ ID NO: 6, respectively. The term "CD22" also includes soluble forms of CD22, referred to as sCD22.

Chemotherapeutic agents: Any chemical agent with therapeutic usefulness in the treatment of diseases characterized by abnormal cell growth. Such diseases include tumors, neoplasms, and cancer as well as diseases characterized by hyperplastic growth such as psoriasis. In one embodiment, a chemotherapeutic agent is an agent of use in treating a B-cell malignancy, such as non-Hodgkin's lymphoma, hairy cell leukemia or chronic lymphocytic leukemia. In one embodiment, a chemotherapeutic agent is a radioactive compound. One of skill in the art can readily identify a chemotherapeutic agent of use (see for example, Slapak and Kufe, *Principles of Cancer Therapy*, Chapter 86 in Harrison's Principles of Internal Medicine, 14th edition; Perry et al., *Chemotherapy*, Ch. 17 in Abeloff, Clinical Oncology $2^{nd}$ ed., © 2000 Churchill Livingstone, Inc; Baltzer, L., Berkery, R. (eds.): *Oncology Pocket Guide to Chemotherapy*, 2nd ed. St. Louis, Mosby-Year Book, 1995; Fischer, D. S., Knobf, M. F., Durivage, H. J. (eds): *The Cancer Chemotherapy Handbook*, 4th ed. St. Louis, Mosby-Year Book, 1993). Combination chemotherapy is the administration of more than one agent to treat cancer. One example is the administration of an antibody that binds CD22 or a fragment thereof used in combination with a radioactive or chemical compound.

Chronic lymphocytic leukemia (CLL) is a lymphoproliferative disorder characterized by lymphocytosis, lymphadenopathy, and organomegaly. It can be conceived of as a lymphoma that involves the peripheral blood.

Conservative variants: "Conservative" amino acid substitutions are those substitutions that do not substantially affect or decrease the affinity of an antibody to CD22. For example, a human antibody that specifically binds CD22 can include at most about 1, at most about 2, at most about 5, and most about 10, or at most about 15 conservative substitutions and specifically bind the original CD22 polypeptide. The term conservative variation also includes the use of a substituted amino acid in place of an unsubstituted parent amino acid, provided that antibody specifically binds CD22. Non-conservative substitutions are those that reduce an activity or binding to CD22.

Conservative amino acid substitution tables providing functionally similar amino acids are well known to one of ordinary skill in the art. The following six groups are examples of amino acids that are considered to be conservative substitutions for one another:

1) Alanine (A), Serine (S), Threonine (T);
2) Aspartic acid (D), Glutamic acid (E);
3) Asparagine (N), Glutamine (Q);
4) Arginine (R), Lysine (K);
5) Isoleucine (I), Leucine (L), Methionine (M), Valine (V); and
6) Phenylalanine (F), Tyrosine (Y), Tryptophan (W).

Complementarity determining region (CDR): Amino acid sequences which together define the binding affinity and specificity of the natural Fv region of a native Ig binding site. The light and heavy chains of an Ig each have three CDRs, designated L-CDR1, L-CDR2, L-CDR3 and H-CDR1, H-CDR2, H-CDR3, respectively.

Contacting: Placement in direct physical association; includes both in solid and liquid form.

Cytotoxicity: The toxicity of a molecule, such as an immunotoxin, to the cells intended to be targeted, as opposed to the cells of the rest of an organism. In one embodiment, in contrast, the term "toxicity" refers to toxicity of an immunotoxin to cells other than those that are the cells intended to be targeted by the targeting moiety of the immunotoxin, and the term "animal toxicity" refers to toxicity of the immunotoxin to an animal by toxicity of the immunotoxin to cells other than those intended to be targeted by the immunotoxin.

Degenerate variant (of CD22): A polynucleotide encoding a CD22 polypeptide or an antibody that binds CD22 that includes a sequence that is degenerate as a result of the genetic code. There are 20 natural amino acids, most of which are specified by more than one codon. Therefore, all degenerate nucleotide sequences are included as long as the amino acid sequence of the CD22 polypeptide or antibody that binds CD22 encoded by the nucleotide sequence is unchanged.

Detecting (or detection): Refers to quantitatively or qualitatively determining the presence of a biomolecule under investigation. For example, in one embodiment, detecting a B-cell malignancy includes quantitatively or qualitatively determining the presence of soluble CD22 in a sample.

Diagnosing: Diagnosing or diagnosis of a B-cell malignancy includes both detecting a B-cell malignancy and identifying a B-cell malignancy, for example identifying a B-cell malignancy as non-Hodgkin's lymphoma, hairy cell leukemia or chronic lymphocytic leukemia.

Effector molecule (EM): The portion of a chimeric molecule that is intended to have a desired effect on a cell to which the chimeric molecule is targeted. Effector molecule is also known as an effector moiety, therapeutic agent, or diagnostic agent, or similar terms. In some embodiments disclosed herein, the EM is a toxin or a detectable label.

Therapeutic agents include such compounds as nucleic acids, proteins, peptides, amino acids or derivatives, glycoproteins, radioisotopes, lipids, carbohydrates, or recombinant viruses. Nucleic acid therapeutic and diagnostic moieties include antisense nucleic acids, derivatized oligonucleotides for covalent cross-linking with single or duplex DNA, and triplex forming oligonucleotides. Alternatively, the molecule linked to a targeting moiety, such as an anti-CD22 antibody, may be an encapsulation system, such as a liposome or micelle that contains a therapeutic composition such as a drug, a nucleic acid (such as an antisense nucleic acid), or another therapeutic moiety that can be shielded from direct exposure to the circulatory system. Means of preparing liposomes attached to antibodies are well known to those of skill in the art (see, for example, U.S. Pat. No. 4,957,735; and Connor et al., *Pharm. Ther.* 28:341-365, 1985). Diagnostic agents or moieties include radioisotopes and other detectable labels. Detectable labels useful for such purposes are also well known in the art, and include radioactive isotopes such as $^{32}$P, $^{125}$I, and $^{131}$I, fluorophores, chemiluminescent agents, and enzymes.

Epitope: An antigenic determinant. These are particular chemical groups or peptide sequences on a molecule that are antigenic, i.e. that elicit a specific immune response. An antibody specifically binds a particular antigenic epitope on a polypeptide, such as CD22.

Expressed: Translation of a nucleic acid into a protein. Proteins may be expressed and remain intracellular, become a component of the cell surface membrane, or be secreted into the extracellular matrix or medium.

Framework region: Amino acid sequences interposed between CDRs. Includes variable light and variable heavy framework regions. The framework regions serve to hold the CDRs in an appropriate orientation for antigen binding.

Hairy cell leukemia (HCL) is a malignant disorder of small B-lymphocytes that gets its name from the presence of cytoplasmic projections in these cells. Subjects with HCL commonly present with pancytopenia, splenomegaly and marrow fibrosis. The peripheral blood usually contains a small number of hairy cells. Hairy cells proliferate in the red pulp of the spleen, so splenomegaly is common.

Host cells: Cells in which a vector can be propagated and its DNA expressed. The cell may be prokaryotic or eukaryotic. The term also includes any progeny of the subject host cell. It is understood that all progeny may not be identical to the parental cell since there may be mutations that occur during replication. However, such progeny are included when the term "host cell" is used.

Human anti-murine antibody (HAMA) response: An immune response in a human subject to the variable and constant regions of a murine antibody that has been administered to the patient. Repeated antibody administration may lead to an increased rate of clearance of the antibody from the patient's serum and may also elicit allergic reactions in the patient.

Immune response: A response of a cell of the immune system, such as a B cell, T cell, or monocyte, to a stimulus. In one embodiment, the response is specific for a particular antigen (an "antigen-specific response"), such as CD22. In one embodiment, an immune response is a T cell response, such as a CD4+ response or a CD8+ response. In another embodiment, the response is a B cell response, and results in the production of specific antibodies.

Immunoconjugate: A covalent linkage of an effector molecule to an antibody. The effector molecule can be a detectable label or a toxin. Specific, non-limiting examples of toxins include, but are not limited to, abrin, ricin, *Pseudomonas* exotoxin (PE, such as PE35, PE37, PE38, and PE40), diphtheria toxin (DT), botulinum toxin, or modified toxins thereof, or other toxic agents that directly or indirectly inhibit cell growth or kill cells. For example, PE and DT are highly toxic compounds that typically bring about death through liver toxicity. PE and DT, however, can be modified into a form for use as an immunotoxin by removing the native targeting component of the toxin (such as the domain Ia of PE and the B chain of DT) and replacing it with a different targeting moiety, such as an antibody. A "chimeric molecule" is a targeting moiety, such as a ligand or an antibody, conjugated (coupled) to an effector molecule. The term "conjugated" or "linked" refers to making two polypeptides into one contiguous polypeptide molecule. In one embodiment, an antibody is joined to an effector molecule. In another embodiment, an antibody joined to an effector molecule is further joined to a lipid or other molecule to a protein or peptide to increase its half-life in the body. The linkage can be either by chemical or recombinant means. In one embodiment, the linkage is chemical, wherein a reaction between the antibody moiety and the effector molecule has produced a covalent bond formed between the two molecules to form one molecule. A peptide linker (short peptide sequence) can optionally be included between the antibody and the effector molecule. Because immunoconjugates were originally prepared from two molecules with separate functionalities, such as an antibody and an effector molecule, they are also sometimes referred to as "chimeric molecules." The term "chimeric molecule," as used herein, therefore refers to a targeting moiety, such as a ligand or an antibody, conjugated (coupled) to an effector molecule.

Immunogenic peptide: A peptide, such as a CD22 peptide, which comprises an allele-specific motif or other sequence, such as an N-terminal repeat, such that the peptide will bind an MHC molecule and induce a cytotoxic T lymphocyte ("CTL") response, or a B cell response (e.g. antibody production) against the antigen from which the immunogenic peptide is derived.

In one embodiment, immunogenic peptides are identified using sequence motifs or other methods, such as neural net or polynomial determinations, known in the art. Typically, algorithms are used to determine the "binding threshold" of peptides to select those with scores that give them a high probability of binding at a certain affinity and will be immunogenic. The algorithms are based either on the effects on MHC binding of a particular amino acid at a particular position, the effects on antibody binding of a particular amino acid at a particular position, or the effects on binding of a particular substitution in a motif-containing peptide. Within the context of an immunogenic peptide, a "conserved residue" is one which appears in a significantly higher frequency than would be expected by random distribution at a particular position in a peptide. In one embodiment, a conserved residue is one where the MHC structure may provide a contact point with the immunogenic peptide. In one specific non-limiting example, an immunogenic polypeptide includes a region of CD22, or a fragment thereof, wherein the polypeptide that is expressed on the cell surface of a host cell that expresses the full-length CD22 polypeptide.

Immunogenic composition: As used herein, an immunogenic composition is a composition comprising a CD22 polypeptide that induces a measurable CTL response against cells expressing CD22 polypeptide, or induces a measurable B cell response (such as production of antibodies) against a CD22 polypeptide. It further refers to isolated nucleic acids encoding a CD22 polypeptide that can be used to express the CD22 polypeptide (and thus be used to elicit an immune response against this polypeptide). For in vitro use, an immunogenic composition may consist of the isolated protein or peptide epitope. For in vivo use, the immunogenic composition will typically comprise the protein or immunogenic peptide in pharmaceutically acceptable carriers, and/or other agents. Any particular peptide, such as a CD22 polypeptide, or nucleic acid encoding the polypeptide, can be readily tested for its ability to induce a CTL or B cell response by art-recognized assays. Immunogenic compositions can include adjuvants, which are well known to one of skill in the art.

Immunologically reactive conditions: Includes reference to conditions which allow an antibody raised against a particular epitope to bind to that epitope to a detectably greater degree than, and/or to the substantial exclusion of, binding to substantially all other epitopes. Immunologically reactive conditions are dependent upon the format of the antibody binding reaction and typically are those utilized in immunoassay protocols or those conditions encountered in vivo. See Harlow & Lane (*Antibodies, A Laboratory Manual*, Cold Spring Harbor Publications, New York, 1988) for a description of immunoassay formats and conditions. The immunologically reactive conditions employed in the methods are "physiological conditions" which include reference to conditions (such as temperature, osmolarity, pH) that are typical inside a living mammal or a mammalian cell. While it is recognized that some organs are subject to extreme conditions, the intra-organismal and intracellular environment normally lies around pH 7 (i.e., from pH 6.0 to pH 8.0, more typically pH 6.5 to 7.5), contains water as the predominant solvent, and exists at a temperature above 0° C. and below 50° C. Osmolarity is within the range that is supportive of cell viability and proliferation.

Isolated: An "isolated" biological component, such as a nucleic acid, protein (including antibodies) or organelle, has been substantially separated or purified away from other biological components in the environment (such as a cell) in which the component naturally occurs, i.e., other chromosomal and extra-chromosomal DNA and RNA, proteins and organelles. Nucleic acids and proteins that have been "isolated" include nucleic acids and proteins purified by standard purification methods. The term also embraces nucleic acids and proteins prepared by recombinant expression in a host cell as well as chemically synthesized nucleic acids.

Label: A detectable compound or composition that is conjugated directly or indirectly to another molecule, such as an antibody or a protein, to facilitate detection of that molecule. Specific, non-limiting examples of labels include fluorescent tags, enzymatic linkages, and radioactive isotopes. In one example, a "labeled antibody" refers to incorporation of another molecule in the antibody. For example, the label is a detectable marker, such as the incorporation of a radiolabeled amino acid or attachment to a polypeptide of biotinyl moieties that can be detected by marked avidin (for example, streptavidin containing a fluorescent marker or enzymatic activity that can be detected by optical or colorimetric methods). Various methods of labeling polypeptides and glycoproteins are known in the art and may be used. Examples of labels for polypeptides include, but are not limited to, the following: radioisotopes or radionucleotides (such as $^{35}$S or $^{131}$I) fluorescent labels (such as fluorescein isothiocyanate (FITC), rhodamine, lanthanide phosphors), enzymatic labels (such as horseradish peroxidase, beta-galactosidase, luciferase, alkaline phosphatase), chemiluminescent markers, biotinyl groups, predetermined polypeptide epitopes recognized by a secondary reporter (such as a leucine zipper pair sequences, binding sites for secondary antibodies, metal binding domains, epitope tags), or magnetic agents, such as gadolinium chelates. In some embodiments, labels are attached by spacer arms of various lengths to reduce potential steric hindrance.

Linker: In some cases, a linker is a peptide within an antibody binding fragment (such as an Fv fragment) which serves to indirectly bond the variable heavy chain to the variable light chain. "Linker" can also refer to a peptide serving to link a targeting moiety, such as an antibody, to an effector molecule, such as a cytotoxin or a detectable label.

The terms "conjugating," "joining," "bonding" or "linking" refer to making two polypeptides into one contiguous polypeptide molecule, or to covalently attaching a radionuclide or other molecule to a polypeptide, such as an scFv. In the specific context, the terms include reference to joining a ligand, such as an antibody moiety, to an effector molecule. The linkage can be either by chemical or recombinant means. "Chemical means" refers to a reaction between the antibody moiety and the effector molecule such that there is a covalent bond formed between the two molecules to form one molecule.

Mammal: This term includes both human and non-human mammals. Similarly, the term "subject" includes both human and veterinary subjects.

Major histocompatibility complex (MHC): Generic designation meant to encompass the histocompatibility antigen systems (class I and class II) described in different species, including the human leukocyte antigens ("HLA"). The term "motif" refers to the pattern of residues in a peptide of defined length, usually about 8 to about 11 amino acids, which is recognized by a particular MHC allele. The peptide motifs are typically different for each MHC allele and differ in the pattern of the highly conserved residues and negative binding residues.

Neoplasia, malignancy, cancer or tumor: A neoplasm is an abnormal growth of tissue or cells that results from excessive cell division. Neoplastic growth can produce a tumor. The amount of a tumor in an individual is the "tumor burden" which can be measured as the number, volume, or weight of the tumor. A tumor that does not metastasize is referred to as "benign." A tumor that invades the surrounding tissue and/or can metastasize is referred to as "malignant." Examples of hematological tumors include leukemias, including acute leukemias (such as acute lymphocytic leukemia, acute myelocytic leukemia, acute myelogenous leukemia and myeloblastic, promyelocytic, myelomonocytic, monocytic and erythroleukemia), chronic leukemias (such as chronic myelocytic (granulocytic) leukemia, chronic myelogenous leukemia, and chronic lymphocytic leukemia), polycythemia vera, lymphoma, Hodgkin's disease, non-Hodgkin's lymphoma (indolent and high grade forms), multiple myeloma, Waldenstrom's macroglobulinemia, heavy chain disease, myelodysplastic syndrome, hairy cell leukemia and myelodysplasia.

Examples of solid tumors, such as sarcomas and carcinomas, include fibrosarcoma, myxosarcoma, liposarcoma, chondrosarcoma, osteogenic sarcoma, and other sarcomas, synovioma, mesothelioma, Ewing's tumor, leiomyosarcoma, rhabdomyosarcoma, colon carcinoma, lymphoid malignancy, pancreatic cancer, breast cancer, lung cancers, ovarian cancer, prostate cancer, hepatocellular carcinoma, squamous cell carcinoma, basal cell carcinoma, adenocarcinoma, sweat gland carcinoma, medullary thyroid carcinoma, papillary thyroid carcinoma, pheochromocytomas sebaceous gland carcinoma, papillary carcinoma, papillary adenocarcinomas, medullary carcinoma, bronchogenic carcinoma, renal cell carcinoma, hepatoma, bile duct carcinoma, choriocarcinoma, Wilms' tumor, cervical cancer, testicular tumor, seminoma, bladder carcinoma, and CNS tumors (such as a glioma, astrocytoma, medulloblastoma, craniopharyogioma, ependymoma, pinealoma, hemangioblastoma, acoustic neuroma, oligodendroglioma, menangioma, melanoma, neuroblastoma and retinoblastoma).

In several examples, the malignancy is a B-cell malignancy, such as, but not limited to non-Hodgkin's lymphoma, hairy cell leukemia or chronic lymphocytic leukemia.

Non-Hodgkin's lymphoma (NHL): Refers to a heterogeneous group of cancers principally arising from B lymphocytes. The subtypes of NHL are typically grouped into three distinct categories based on their aggressiveness, or histologic grade. These categories are indolent (low-grade), aggressive (intermediate-grade) and highly aggressive (high-grade). NHLs include, but are not limited to, diffuse large B-cell lymphoma, mantle cell lymphoma, MALT lymphoma, follicular lymphoma, small lymphocytic lymphoma and Burkitt's lymphoma.

Nucleic acid: A polymer composed of nucleotide units (ribonucleotides, deoxyribonucleotides, related naturally occurring structural variants, and synthetic non-naturally occurring analogs thereof) linked via phosphodiester bonds, related naturally occurring structural variants, and synthetic non-naturally occurring analogs thereof. Thus, the term includes nucleotide polymers in which the nucleotides and the linkages between them include non-naturally occurring synthetic analogs, such as, for example and without limitation, phosphorothioates, phosphoramidates, methyl phosphonates, chiral-methyl phosphonates, 2-O-methyl ribonucleotides, peptide-nucleic acids (PNAs), and the like. Such polynucleotides can be synthesized, for example, using an automated DNA synthesizer. The term "oligonucleotide" typically refers to short polynucleotides, generally no greater than about 50 nucleotides. It will be understood that when a nucleotide sequence is represented by a DNA sequence (i.e., A, T, G, C), this also includes an RNA sequence (i.e., A, U, G, C) in which "U" replaces "T."

Conventional notation is used herein to describe nucleotide sequences: the left-hand end of a single-stranded nucleotide sequence is the 5'-end; the left-hand direction of a double-stranded nucleotide sequence is referred to as the 5'-direction. The direction of 5' to 3' addition of nucleotides to nascent RNA transcripts is referred to as the transcription direction. The DNA strand having the same sequence as an mRNA is referred to as the "coding strand;" sequences on the DNA strand having the same sequence as an mRNA transcribed from that DNA and which are located 5' to the 5'-end of the RNA transcript are referred to as "upstream sequences;" sequences on the DNA strand having the same sequence as the RNA and which are 3' to the 3' end of the coding RNA transcript are referred to as "downstream sequences."

"cDNA" refers to a DNA that is complementary or identical to an mRNA, in either single stranded or double stranded form.

"Encoding" refers to the inherent property of specific sequences of nucleotides in a polynucleotide, such as a gene, a cDNA, or an mRNA, to serve as templates for synthesis of other polymers and macromolecules in biological processes having either a defined sequence of nucleotides (i.e., rRNA, tRNA and mRNA) or a defined sequence of amino acids and the biological properties resulting therefrom. Thus, a gene encodes a protein if transcription and translation of mRNA produced by that gene produces the protein in a cell or other biological system. Both the coding strand, the nucleotide sequence of which is identical to the mRNA sequence and is usually provided in sequence listings, and non-coding strand, used as the template for transcription, of a gene or cDNA can be referred to as encoding the protein or other product of that gene or cDNA. Unless otherwise specified, a "nucleotide sequence encoding an amino acid sequence" includes all nucleotide sequences that are degenerate versions of each other and that encode the same amino acid sequence. Nucleotide sequences that encode proteins and RNA may include introns.

Oligonucleotide: A linear polynucleotide sequence of up to about 100 nucleotide bases in length.

Operably linked: A first nucleic acid sequence is operably linked with a second nucleic acid sequence when the first nucleic acid sequence is placed in a functional relationship with the second nucleic acid sequence. For instance, a promoter, such as the CMV promoter, is operably linked to a coding sequence if the promoter affects the transcription or expression of the coding sequence. Generally, operably linked DNA sequences are contiguous and, where necessary to join two protein-coding regions, in the same reading frame.

ORF (open reading frame): A series of nucleotide triplets (codons) coding for amino acids without any termination codons. These sequences are usually translatable into a peptide.

Pharmaceutical agent: A chemical compound or composition capable of inducing a desired therapeutic or prophylactic effect when properly administered to a subject or a cell.

Pharmaceutically acceptable carriers: The pharmaceutically acceptable carriers of use are conventional. *Remington's Pharmaceutical Sciences*, by E. W. Martin, Mack Publishing Co., Easton, Pa., 15th Edition, 1975, describes compositions and formulations suitable for pharmaceutical delivery of the antibodies disclosed herein.

In general, the nature of the carrier will depend on the particular mode of administration being employed. For instance, parenteral formulations usually comprise injectable fluids that include pharmaceutically and physiologically acceptable fluids such as water, physiological saline, balanced salt solutions, aqueous dextrose, glycerol or the like as a vehicle. For solid compositions (such as powder, pill, tablet, or capsule forms), conventional non-toxic solid carriers can include, for example, pharmaceutical grades of mannitol, lactose, starch, or magnesium stearate. In addition to biologically neutral carriers, pharmaceutical compositions to be administered can contain minor amounts of non-toxic auxiliary substances, such as wetting or emulsifying agents, preservatives, and pH buffering agents and the like, for example sodium acetate or sorbitan monolaurate.

Polynucleotide: The term polynucleotide or nucleic acid sequence refers to a polymeric form of nucleotide at least 10 bases in length. A recombinant polynucleotide includes a polynucleotide that is not immediately contiguous with both of the coding sequences with which it is immediately contiguous (one on the 5' end and one on the 3' end) in the naturally occurring genome of the organism from which it is derived. The term therefore includes, for example, a recombinant DNA which is incorporated into a vector; into an autonomously replicating plasmid or virus; or into the genomic DNA of a prokaryote or eukaryote, or which exists as a separate molecule (such as a cDNA) independent of other sequences. The nucleotides can be ribonucleotides, deoxyribonucleotides, or modified forms of either nucleotide. The term includes single- and double-stranded forms of DNA.

Polypeptide: Any chain of amino acids, regardless of length or post-translational modification (such as glycosylation or phosphorylation). In one embodiment, the polypeptide is CD22 polypeptide. A "residue" refers to an amino acid or amino acid mimetic incorporated in a polypeptide by an amide bond or amide bond mimetic. A polypeptide has an amino terminal (N-terminal) end and a carboxy terminal (C-terminal) end.

Preventing, treating or ameliorating a disease: "Preventing" a disease refers to inhibiting the full development of a disease. "Treating" refers to a therapeutic intervention that ameliorates a sign or symptom of a disease or pathological condition after it has begun to develop, such as a B-cell malignancy. "Ameliorating" refers to the reduction in the number or severity of signs or symptoms of a disease, such as a B-cell malignancy.

Promoter: A promoter is an array of nucleic acid control sequences that directs transcription of a nucleic acid. A promoter includes necessary nucleic acid sequences near the start site of transcription, for example, in the case of a polymerase II type promoter, a TATA element. A promoter also optionally includes distal enhancer or repressor elements which can be located as much as several thousand base pairs from the start site of transcription. Both constitutive and inducible promoters are included (see for example, Bitter et al., *Methods in Enzymology* 153:516-544, 1987).

Specific, non-limiting examples of promoters include promoters derived from the genome of mammalian cells (such as the metallothionein promoter) or from mammalian viruses (such as the retrovirus long terminal repeat; the adenovirus late promoter; the vaccinia virus 7.5K promoter) may be used. Promoters produced by recombinant DNA or synthetic techniques may also be used. A polynucleotide can be inserted into an expression vector that contains a promoter sequence which facilitates the efficient transcription of the inserted genetic sequence of the host. The expression vector typically contains an origin of replication, a promoter, as well as specific nucleic acid sequences that allow phenotypic selection of the transformed cells.

Purified: The term purified does not require absolute purity; rather, it is intended as a relative term. Thus, for example, a purified peptide preparation is one in which the peptide or protein is more enriched than the peptide or protein is in its natural environment within a cell. In one embodiment, a preparation is purified such that the protein or peptide represents at least 50%, such as at least 60%, at least 70%, at least 80%, at least 90%, at least 95%, or at least 98%, of the total peptide or protein content of the preparation.

The CD22 polypeptides disclosed herein, or antibodies that specifically bind CD22, can be purified by any of the means known in the art. See for example *Guide to Protein Purification*, ed. Deutscher, *Meth. Enzymol.* 185, Academic Press, San Diego, 1990; and Scopes, *Protein Purification: Principles and Practice*, Springer Verlag, New York, 1982. Substantial purification denotes purification from other proteins or cellular components. A substantially purified protein is at least 60%, 70%, 80%, 90%, 95% or 98% pure. Thus, in one specific, non-limiting example, a substantially purified protein is 90% free of other proteins or cellular components.

Recombinant: A recombinant nucleic acid is one that has a sequence that is not naturally occurring or has a sequence that is made by an artificial combination of two otherwise separated segments of sequence. This artificial combination is often accomplished by chemical synthesis or, more commonly, by the artificial manipulation of isolated segments of nucleic acids, for example, by genetic engineering techniques.

Recombinant toxins: Chimeric proteins in which a cell targeting moiety is fused to a toxin (Pastan et al., *Science*, 254:1173-1177, 1991). If the cell targeting moiety is the Fv portion of an antibody, the molecule is termed a recombinant immunotoxin (Chaudhary et al., *Nature*, 339:394-397, 1989). The toxin moiety is genetically altered so that it cannot bind to the toxin receptor present on most normal cells. Recombinant immunotoxins selectively kill cells which are recognized by the antigen binding domain. These recombinant toxins and immunotoxins can be used to treat cancer, for example, cancers in which CD22 is expressed.

Sequence identity: The similarity between amino acid sequences is expressed in terms of the similarity between the sequences, otherwise referred to as sequence identity. Sequence identity is frequently measured in terms of percentage identity (or similarity or homology); the higher the percentage, the more similar the two sequences are. Homologs or variants of a polypeptide will possess a relatively high degree of sequence identity when aligned using standard methods.

Methods of alignment of sequences for comparison are well known in the art. Various programs and alignment algorithms are described in: Smith and Waterman, *Adv. Appl. Math.* 2:482, 1981; Needleman and Wunsch, *J. Mol. Biol.* 48:443, 1970; Pearson and Lipman, *Proc. Natl. Acad. Sci. U.S.A.* 85:2444, 1988; Higgins and Sharp, *Gene* 73:237, 1988; Higgins and Sharp, *CABIOS* 5:151, 1989; Corpet et al., *Nucleic Acids Research* 16:10881, 1988; and Pearson and Lipman, *Proc. Natl. Acad. Sci. U.S.A.* 85:2444, 1988. Altschul et al., *Nature Genet.* 6:119, 1994, presents a detailed consideration of sequence alignment methods and homology calculations.

The NCBI Basic Local Alignment Search Tool (BLAST) (Altschul et al., *J. Mol. Biol.* 215:403, 1990) is available from several sources, including the National Center for Biotechnology Information (NCBI, Bethesda, Md.) and on the internet, for use in connection with the sequence analysis programs blastp, blastn, blastx, tblastn and tblastx. A description of how to determine sequence identity using this program is available on the NCBI website on the internet.

Homologs and variants of a $V_L$ or a $V_H$ of an antibody that specifically binds a CD22 polypeptide are typically characterized by possession of at least about 75%, for example at least about 80%, 90%, 95%, 96%, 97%, 98% or 99% sequence identity counted over the full length alignment with the amino acid sequence of the antibody using the NCBI Blast 2.0, gapped blastp set to default parameters. For comparisons of amino acid sequences of greater than about 30 amino acids, the Blast 2 sequences function is employed using the default BLOSUM62 matrix set to default parameters, (gap existence cost of 11, and a per residue gap cost of 1). When aligning short peptides (fewer than around 30 amino acids), the alignment should be performed using the Blast 2 sequences function, employing the PAM30 matrix set to default parameters (open gap 9, extension gap 1 penalties). Proteins with even greater similarity to the reference sequences will show increasing percentage identities when assessed by this method, such as at least 80%, at least 85%, at least 90%, at least 95%, at least 98%, or at least 99% sequence identity. When less than the entire sequence is being compared for sequence identity, homologs and variants will typically possess at least 80% sequence identity over short windows of 10-20 amino acids, and may possess sequence identities of at least 85% or at least 90% or 95% depending on their similarity to the reference sequence. Methods for determining sequence identity over such short windows are available at the NCBI website on the internet. One of skill in the art will appreciate that these sequence identity ranges are provided for guidance only; it is entirely possible that strongly significant homologs could be obtained that fall outside of the ranges provided.

Soluble CD22 (sCD22): A non-membrane-bound form of CD22, a 135 kDa phosphoglycoprotein adhesion molecule present on the surface of B cells, including human B cell malignancies. Soluble CD22 can be any portion of the CD22 protein not connected to the membrane, and is usually a truncated form of CD22. For example, sCD22 can be about 100 kDa, however it can also be no more than or no less than about 90, 80, 70, 60, 50, 40, or 30 kDa, or smaller. Standard software is available for determining the transmembrane domain of CD22.

Specific binding agent: An agent that binds substantially only to a defined target. Thus a CD22 specific binding agent is an agent that binds substantially to a CD22 polypeptide. In one embodiment, the specific binding agent is a human monoclonal antibody that specifically binds the CD22 polypeptide.

The term "specifically binds" refers, with respect to an antigen such as CD22, to the preferential association of an antibody or other ligand, in whole or part, with a cell or tissue bearing that antigen and not to cells or tissues lacking that antigen. It is recognized that a certain degree of non-specific interaction may occur between a molecule and a non-target cell or tissue. Nevertheless, specific binding may be distinguished as mediated through specific recognition of the antigen. Although selectively reactive antibodies bind antigen, they may do so with low affinity. On the other hand, specific binding results in a much stronger association between the antibody (or other ligand) and cells bearing the antigen than between the bound antibody (or other ligand) and cells lacking the antigen. Specific binding typically results in greater than 2-fold, such as greater than 5-fold, greater than 10-fold, or greater than 100-fold increase in amount of bound antibody or other ligand (per unit time) to a cell or tissue bearing the CD22 polypeptide as compared to a cell or tissue lacking the polypeptide. Specific binding to a protein under such conditions requires an antibody that is selected for its specificity for a particular protein. A variety of immunoassay formats are appropriate for selecting antibodies or other ligands specifically immunoreactive with a particular protein. For example, solid-phase ELISA immunoassays are routinely used to select monoclonal antibodies specifically immunoreactive with a protein. See Harlow & Lane (*Antibodies, A Laboratory Manual*, Cold Spring Harbor Publications, New York, 1988) for a description of immunoassay formats and conditions that can be used to determine specific immunoreactivity.

Subject: Living multi-cellular vertebrate organisms, a category that includes both human and veterinary subjects, including human and non-human mammals.

Therapeutically effective amount: A quantity of a specific substance sufficient to achieve a desired effect in a subject being treated. For instance, this can be the amount necessary to inhibit or suppress growth of a tumor. In one embodiment, a therapeutically effective amount is the amount necessary to eliminate a tumor. When administered to a subject, a dosage will generally be used that will achieve target tissue concentrations (for example, in tumors) that has been shown to achieve a desired in vitro effect.

Toxin: A molecule that is cytotoxic for a cell. Toxins include abrin, ricin, *Pseudomonas* exotoxin (PE), diphtheria toxin (DT), botulinum toxin, saporin, restrictocin or gelonin, or modified toxins thereof. For example, PE and DT are highly toxic compounds that typically bring about death through liver toxicity. PE and DT, however, can be modified into a form for use as an immunotoxin by removing the native targeting component of the toxin (such as domain Ia of PE or the B chain of DT) and replacing it with a different targeting moiety, such as an antibody.

Transduced: A transduced cell is a cell into which has been introduced a nucleic acid molecule by molecular biology techniques. As used herein, the term transduction encompasses all techniques by which a nucleic acid molecule might be introduced into such a cell, including transfection with viral vectors, transformation with plasmid vectors, and introduction of naked DNA by electroporation, lipofection, and particle gun acceleration.

Vector: A nucleic acid molecule as introduced into a host cell, thereby producing a transformed host cell. A vector may include nucleic acid sequences that permit it to replicate in a host cell, such as an origin of replication. A vector may also include one or more selectable marker genes and other genetic elements known in the art.

Unless otherwise explained, all technical and scientific terms used herein have the same meaning as commonly understood by one of ordinary skill in the art to which this disclosure belongs. The singular terms "a," "an," and "the" include plural referents unless context clearly indicates otherwise. Similarly, the word "or" is intended to include "and" unless the context clearly indicates otherwise. Hence "comprising A or B" means including A, or B, or A and B. It is further to be understood that all base sizes or amino acid sizes, and all molecular weight or molecular mass values, given for nucleic acids or polypeptides are approximate, and are provided for description. Although methods and materials similar or equivalent to those described herein can be used in the practice or testing of the present disclosure, suitable methods and materials are described below. All publications, patent applications, patents, and other references mentioned herein are incorporated by reference in their entirety. In case of conflict, the present specification, including explanations of terms, will control. In addition, the materials, methods, and examples are illustrative only and not intended to be limiting.

III. Human Monoclonal Antibodies that Specifically Bind CD22

Described herein are isolated human monoclonal antibodies specific for human CD22. The human monoclonal antibodies bind CD22 with a dissociation constant ($K_d$) of about 25 nM or less. In some embodiments, the human monoclonal antibodies bind human CD22 with a binding affinity of about 25 nM or less, 24 nM or less, 23 nM or less, 22 nM or less, 21 nM or less, 20 nM or less, about 19 nM or less, about 18 nM or less, about 17 nM or less, about 16 nM or less, or about 15 nM or less. In other embodiments, the human monoclonal antibodies bind human CD22 with a binding affinity of about 10 nM or less, about 9 nM or less, about 8 nM or less, about 7 nM or less, about 6 nM or less, or about 5 nM or less. In other embodiments, the human monoclonal antibodies bind human CD22 with a binding affinity of about 4 nM or less, about 3 nM or less, about 2.5 nM or less, about 2 nM or less, about 1.5 nM or less, or about 1 nM or less. In other embodiments, the human monoclonal antibodies bind human CD22 with a binding affinity of about 1 nM or less, about 0.75 nM or less, about 0.5 nM or less, about 0.25 nM or less, or about 0.1 nM or less. In one example, the binding affinity is about 20 nM. In another example, the binding affinity is about 2 nM.

Also described are compositions comprising the provided human monoclonal antibodies and a pharmaceutically acceptable carrier. Nucleic acids encoding these antibodies, expression vectors comprising these nucleic acids, and isolated host cells that express the nucleic acids are also provided.

Also described herein are immunoconjugates comprising the human monoclonal antibodies specific for human CD22. The immunoconjugates can comprise any therapeutic agent, toxin or other moiety. In one example, the toxin is PE or a variant or fragment thereof. Compositions comprising the immunoconjugates are also described.

Compositions comprising the human monoclonal antibodies specific for CD22 can be used for research, diagnostic and therapeutic purposes. For example, the human monoclonal antibodies can be used to treat a subject diagnosed with a B-cell malignancy, such as, but not limited to, non-Hodgkin's lymphoma, Burkitt's lymphoma, small lymphocytic lymphoma, primary effusion lymphoma, diffuse large B-cell lymphoma, splenic marginal zone lymphoma, MALT (mucosa-associated lymphoid tissue) lymphoma, hairy cell leukemia, chronic lymphocytic leukemia and B-cell prolymphocytic leukemia. Immunoconjugates comprising the CD22 antibodies also can be used to treat a patient diagnosed with a B-cell malignancy. The human monoclonal antibodies can also be used to diagnose a B-cell malignancy in a subject. For example, the human monoclonal antibodies can be contacted with a blood sample from the patient to detect elevated levels of soluble CD22, or an elevated number of cells expressing CD22. The antibodies and compositions provided herein can also be used to detect a B-cell malignancy in a subject or to confirm the diagnosis of a B-cell malignancy in a patient. The antibodies can also be used to study the biology of CD22-expressing cancers.

Disclosed herein are fully human monoclonal antibodies that specifically bind human CD22. A major limitation in the clinical use of mouse monoclonal antibodies is the development of a human anti-murine antibody (HAMA) response in the patients receiving the treatments. The HAMA response can involve allergic reactions and an increased rate of clearance of the administered antibody from the serum. Various types of modified monoclonal antibodies have been developed to minimize the HAMA response while trying to maintain the antigen binding affinity of the parent monoclonal antibody. One type of modified monoclonal antibody is a human-mouse chimera in which a murine antigen-binding variable region is coupled to a human constant domain (Morrison and Schlom, *Important Advances in Oncology*, Rosenberg, S. A. (Ed.), 1989). A second type of modified monoclonal antibody is the complementarity determining region (CDR)-grafted, or humanized, monoclonal antibody (Winter and Harris, *Immunol. Today* 14:243-246, 1993). However, the antibodies disclosed herein are fully human; both the framework region and the CDRs are from human antibodies. Thus, a HAMA is not induced when these antibodies are administered to a human subject.

In one embodiment, the antibodies bind CD22 with a dissociation constant ($K_d$) of about 25 nM or less. In several embodiments, the human monoclonal antibodies bind human CD22 with a binding affinity of about 25 nM, about 24 nM, about 23 nM, about 22 nM, about 21 nM about 20 nM, about 15 nM, about 10 nM, about 5 nM, about 4 nM, about 3 nM, about 2.5 nM, about 2 nM, about 1.5 nM, about 1 nM or about 0.5 nM or less.

In some embodiments, the human monoclonal antibody comprises at least a portion of the heavy chain amino acid sequence set forth as SEQ ID NO: 1 or SEQ ID NO: 2. In some embodiments, the human monoclonal antibody comprises at least a portion of the light chain amino acid sequence set forth as SEQ ID NO: 2 or SEQ ID NO: 4. In some examples, the portion of the light chain or heavy chain comprises one or more CDRs. In particular examples, the heavy chain of the antibody comprises amino acids 26-33 of SEQ ID NO: 1, amino acids 51-59 of SEQ ID NO: 1 or amino acids 97-106 of SEQ ID NO: 1, or a combination thereof; or the light chain of the antibody comprises amino acids 27-32 of SEQ ID NO: 2, amino acids 50-52 of SEQ ID NO: 2 or amino acids 89-98 of SEQ ID NO: 2, or a combination thereof; or both. In other examples, the heavy chain of the antibody comprises amino acids 26-35 of SEQ ID NO: 3, amino acids 53-61 of SEQ ID NO: 3 or amino acids 100-113 of SEQ ID NO: 3, or a combination thereof; or the light chain of the antibody comprises amino acids 27-32 of SEQ ID NO: 4, amino acids 50-52 of SEQ ID NO: 4 or amino acids 89-97 of SEQ ID NO: 4, or a combination thereof; or both.

The monoclonal antibody can be of any isotype. The monoclonal antibody can be, for example, an IgM or an IgG antibody, such as IgG$_1$ or an IgG$_2$. The class of an antibody that specifically binds CD22 can be switched with another. In one aspect, a nucleic acid molecule encoding $V_L$ or $V_H$ is isolated using methods well-known in the art, such that it does not include any nucleic acid sequences encoding the constant region of the light or heavy chain, respectively. The nucleic acid molecule encoding $V_L$ or $V_H$ is then operatively linked to a nucleic acid sequence encoding a $C_L$ or $C_H$ from a different class of immunoglobulin molecule. This can be achieved using a vector or nucleic acid molecule that comprises a $C_L$ or $C_H$ chain, as known in the art. For example, an antibody that specifically binds CD22 that was originally IgM may be class switched to an IgG. Class switching can be used to convert one IgG subclass to another, such as from IgG$_1$ to IgG$_2$.

Fully human monoclonal antibodies include a human framework region. This human framework region can include the framework regions disclosed in one or more of SEQ ID NOs: 1-4 (these sequences include CDR sequences as well as framework sequences). However, the framework regions can be from another source. Additional examples of framework sequences that can be used include the amino acid framework sequences of the heavy and light chains disclosed in PCT Publication No. WO 2006/074071 (see, for example, SEQ ID NOs: 1-16 of WO 2006/074071).

Antibody fragments are encompassed by the present disclosure, such as Fab, F(ab')$_2$, and Fv which include a heavy chain and light chain variable region and are capable of binding the epitopic determinant on CD22. These antibody fragments retain the ability to selectively bind with the antigen. These fragments include:

(1) Fab, the fragment which contains a monovalent antigen-binding fragment of an antibody molecule, can be produced by digestion of whole antibody with the enzyme papain to yield an intact light chain and a portion of one heavy chain;

(2) Fab', the fragment of an antibody molecule can be obtained by treating whole antibody with pepsin, followed by reduction, to yield an intact light chain and a portion of the heavy chain; two Fab' fragments are obtained per antibody molecule;

(3) (Fab')$_2$, the fragment of the antibody that can be obtained by treating whole antibody with the enzyme pepsin without subsequent reduction; F(ab')$_2$ is a dimer of two Fab' fragments held together by two disulfide bonds;

(4) Fv, a genetically engineered fragment containing the variable region of the light chain and the variable region of the heavy chain expressed as two chains; and (5) Single chain antibody (such as scFv), defined as a genetically engineered molecule containing the variable region of the light chain, the variable region of the heavy chain, linked by a suitable polypeptide linker as a genetically fused single chain molecule.

(6) A dimer of a single chain antibody (scFV$_2$), defined as a dimer of an scFV. This has also been termed a "miniantibody."

Methods of making these fragments are known in the art (see for example, Harlow and Lane, *Antibodies: A Laboratory Manual*, Cold Spring Harbor Laboratory, New York, 1988). In several examples, the variable region included in the antibody is the variable region of m971 or m972.

In a further group of embodiments, the antibodies are Fv antibodies, which are typically about 25 kDa and contain a complete antigen-binding site with three CDRs per each heavy chain and each light chain. To produce these antibodies, the $V_H$ and the $V_L$ can be expressed from two individual nucleic acid constructs in a host cell. If the $V_H$ and the $V_L$ are expressed non-contiguously, the chains of the Fv antibody are typically held together by noncovalent interactions. However, these chains tend to dissociate upon dilution, so methods have been developed to crosslink the chains through glutaraldehyde, intermolecular disulfides, or a peptide linker. Thus, in one example, the Fv can be a disulfide stabilized Fv (dsFv), wherein the heavy chain variable region and the light chain variable region are chemically linked by disulfide bonds.

In an additional example, the Fv fragments comprise $V_H$ and $V_L$ chains connected by a peptide linker. These single-chain antigen binding proteins (scFv) are prepared by constructing a structural gene comprising DNA sequences encoding the $V_H$ and $V_L$ domains connected by an oligonucleotide. The structural gene is inserted into an expression vector, which is subsequently introduced into a host cell such as *E. coli*. The recombinant host cells synthesize a single polypeptide chain with a linker peptide bridging the two V domains. Methods for producing scFvs are known in the art (see Whitlow et al., *Methods: a Companion to Methods in Enzymology*, Vol. 2, page 97, 1991; Bird et al., *Science* 242:423, 1988; U.S. Pat. No. 4,946,778; Pack et al., *Bio/Technology* 11:1271, 1993; and Sandhu, supra). Dimers of a single chain antibody (scFV$_2$), are also contemplated.

Antibody fragments can be prepared by proteolytic hydrolysis of the antibody or by expression in *E. coli* of DNA encoding the fragment. Antibody fragments can be obtained by pepsin or papain digestion of whole antibodies by conventional methods. For example, antibody fragments can be produced by enzymatic cleavage of antibodies with pepsin to provide a 5S fragment denoted F(ab')2. This fragment can be further cleaved using a thiol reducing agent, and optionally a blocking group for the sulfhydryl groups resulting from cleavage of disulfide linkages, to produce 3.5S Fab' monovalent fragments. Alternatively, an enzymatic cleavage using pepsin produces two monovalent Fab' fragments and an Fc fragment directly (see U.S. Pat. No. 4,036,945 and U.S. Pat. No. 4,331,647, and references contained therein; Nisonhoff et al., *Arch. Biochem. Biophys.* 89:230, 1960; Porter, *Biochem. J.* 73:119, 1959; Edelman et al., *Methods in Enzymology*, Vol. 1, page 422, Academic Press, 1967; and Coligan et al. at sections 2.8.1-2.8.10 and 2.10.1-2.10.4).

Other methods of cleaving antibodies, such as separation of heavy chains to form monovalent light-heavy chain fragments, further cleavage of fragments, or other enzymatic, chemical, or genetic techniques may also be used, so long as the fragments bind to the antigen that is recognized by the intact antibody.

One of skill will realize that conservative variants of the antibodies can be produced. Such conservative variants employed in antibody fragments, such as dsFv fragments or in scFv fragments, will retain critical amino acid residues necessary for correct folding and stabilizing between the $V_H$ and the $V_L$ regions, and will retain the charge characteristics of the residues in order to preserve the low pI and low toxicity of the molecules. Amino acid substitutions (such as at most one, at most two, at most three, at most four, or at most five amino acid substitutions) can be made in the $V_H$ and the $V_L$ regions to increase yield. Conservative amino acid substitution tables providing functionally similar amino acids are well known to one of ordinary skill in the art. The following six groups are examples of amino acids that are considered to be conservative substitutions for one another:

1) Alanine (A), Serine (S), Threonine (T);
2) Aspartic acid (D), Glutamic acid (E);
3) Asparagine (N), Glutamine (Q);
4) Arginine (R), Lysine (K);
5) Isoleucine (I), Leucine (L), Methionine (M), Valine (V); and
6) Phenylalanine (F), Tyrosine (Y), Tryptophan (W).

Additional recombinant anti-CD22 human antibodies can be isolated by screening of a recombinant combinatorial antibody library, such as a Fab phage display library (see, for example, U.S. Patent Application Publication No. 2005/0123900). In some cases the phage display libraries are prepared using cDNAs of the variable regions of heavy and light chains prepared from mRNA derived from human lymphocytes. Methodologies for preparing and screening such libraries are known in the art. There are commercially available kits for generating phage display libraries (for example, the Pharmacia Recombinant Phage Antibody System, catalog no. 27-9400-01; and the Stratagene SurfZAP™ phage display kit, catalog no. 240612). There are also other methods and reagents that can be used in generating and screening antibody display libraries (see, for example, U.S. Pat. No. 5,223,409; PCT Publication No. WO 92/18619; PCT Publication No. WO 91/17271; PCT Publication No. WO 92/20791; PCT Publication No. WO 92/15679; PCT Publication No. WO 93/01288; PCT Publication No. WO 92/01047; PCT Publication No. WO 92/09690; Fuchs et al., *Bio/Technology* 9:1370-1372, 1991; Hay et al., *Hum. Antibod. Hybridomas* 3:81-85, 1992; Huse et al., *Science* 246: 1275-1281, 1989; McCafferty et al., *Nature* 348:552-554, 1990; Griffiths et al., *EMBO J.* 12:725-734, 1993)

In one embodiment, to isolate additional human antibodies that specifically bind CD22, a human antibody that specifically binds CD22, as described herein, is first used to select human heavy and light chain sequences having similar binding activity toward CD22, such as using the epitope imprinting methods disclosed in PCT Publication No. WO 93/06213. The antibody libraries used in this method are scFv libraries prepared and screened, using methods such as those as described in PCT Publication No. WO 92/01047, McCafferty et al., *Nature* 348:552-554, 1990; and/or Griffiths et al., *EMBO J.* 12:725-734, 1993 using human CD22 as the antigen.

Once initial human variable light chain (VL) and variable heavy chain (VH) segments are selected, "mix and match" experiments, in which different pairs of the initially selected VL and VH segments are screened for CD22 binding, are performed to select VL/VH pair combinations of interest. Additionally, to increase binding affinity of the antibody, the VL and VH segments can be randomly mutated, such as within H-CDR3 region or the L-CDR3 region, in a process analogous to the in vivo somatic mutation process responsible for affinity maturation of antibodies during a natural immune response. This in vitro affinity maturation can be accomplished by amplifying VH and VL regions using PCR primers complimentary to the H-CDR3 or L-CDR3, respectively. In this process, the primers have been "spiked" with a random mixture of the four nucleotide bases at certain positions such that the resultant PCR products encode VH and VL segments into which random mutations have been introduced into the VH and/or VL CDR3 regions. These randomly mutated VH and VL segments can be tested to determine the binding affinity for CD22.

Following screening and isolation of an antibody that binds CD22 from a recombinant immunoglobulin display library, nucleic acid encoding the selected antibody can be recovered from the display package (for example, from the phage genome) and subcloned into other expression vectors by standard recombinant DNA techniques, as described herein. If desired, the nucleic acid can be further manipulated to create other antibody fragments, also as described herein. To express a recombinant human antibody isolated by screening of a combinatorial library, the DNA encoding the antibody is cloned into a recombinant expression vector and introduced into a mammalian host cell, as described herein.

IV. Immunoconjugates and Other Therapeutic Moieties

The human monoclonal antibodies specific for human CD22 described herein can be conjugated to a therapeutic agent. Immunoconjugates include, but are not limited to, molecules in which there is a covalent linkage of a therapeutic agent to an antibody. A therapeutic agent is an agent with a particular biological activity directed against a particular target molecule or a cell bearing a target molecule. One of skill in the art will appreciate that therapeutic agents can include various drugs such as vinblastine, daunomycin and the like, cytotoxins such as native or modified *Pseudomonas* exotoxin or Diphtheria toxin, encapsulating agents (such as liposomes) which themselves contain pharmacological compositions, radioactive agents such as $^{125}I$, $^{32}P$, $^{14}C$, $^{3}H$ and $^{35}S$ and other labels, target moieties and ligands.

The choice of a particular therapeutic agent depends on the particular target molecule or cell, and the desired biological effect. Thus, for example, the therapeutic agent can be a cytotoxin that is used to bring about the death of a particular target cell. Conversely, where it is desired to invoke a non-lethal biological response, the therapeutic agent can be conjugated to a non-lethal pharmacological agent or a liposome containing a non-lethal pharmacological agent.

With the therapeutic agents and antibodies described herein, one of skill can readily construct a variety of clones containing functionally equivalent nucleic acids, such as nucleic acids which differ in sequence but which encode the same EM or antibody sequence. Thus, the present invention provides nucleic acids encoding antibodies and conjugates and fusion proteins thereof.

Effector molecules can be linked to an antibody of interest using any number of means known to those of skill in the art. Both covalent and noncovalent attachment means may be used. The procedure for attaching an effector molecule to an antibody varies according to the chemical structure of the effector. Polypeptides typically contain a variety of functional groups; such as carboxylic acid (COOH), free amine (—NH$_2$) or sulfhydryl (—SH) groups, which are available for reaction with a suitable functional group on an antibody to result in the binding of the effector molecule. Alternatively, the antibody is derivatized to expose or attach additional reactive functional groups. The derivatization may involve attachment of any of a number of linker molecules such as those available from Pierce Chemical Company, Rockford, Ill. The linker can be any molecule used to join the antibody to the effector molecule. The linker is capable of forming covalent bonds to both the antibody and to the effector molecule. Suitable linkers are well known to those of skill in the art and include, but are not limited to, straight or branched-chain carbon linkers, heterocyclic carbon linkers, or peptide linkers. Where the antibody and the effector molecule are polypeptides, the linkers may be joined to the constituent amino acids through their side groups (such as through a disulfide linkage to cysteine) or to the alpha carbon amino and carboxyl groups of the terminal amino acids.

In some circumstances, it is desirable to free the effector molecule from the antibody when the immunoconjugate has reached its target site. Therefore, in these circumstances, immunoconjugates will comprise linkages that are cleavable in the vicinity of the target site. Cleavage of the linker to release the effector molecule from the antibody may be prompted by enzymatic activity or conditions to which the immunoconjugate is subjected either inside the target cell or in the vicinity of the target site.

In view of the large number of methods that have been reported for attaching a variety of radiodiagnostic compounds, radiotherapeutic compounds, label (such as enzymes or fluorescent molecules) drugs, toxins, and other agents to antibodies one skilled in the art will be able to determine a suitable method for attaching a given agent to an antibody or other polypeptide.

The antibodies or antibody fragments disclosed herein can be derivatized or linked to another molecule (such as another peptide or protein). In general, the antibodies or portion thereof is derivatized such that the binding to CD22 is not affected adversely by the derivatization or labeling. For example, the antibody can be functionally linked (by chemical coupling, genetic fusion, noncovalent association or otherwise) to one or more other molecular entities, such as another antibody (for example, a bispecific antibody or a diabody), a detection agent, a pharmaceutical agent, and/or a protein or peptide that can mediate associate of the antibody or antibody portion with another molecule (such as a streptavidin core region or a polyhistidine tag).

One type of derivatized antibody is produced by cross linking two or more antibodies (of the same type or of different types, such as to create bispecific antibodies). Suitable crosslinkers include those that are heterobifunctional, having two distinctly reactive groups separated by an appropriate spacer (such as m-maleimidobenzoyl-N-hydroxysuccinimide ester) or homobifunctional (such as disuccinimidyl suberate). Such linkers are available from Pierce Chemical Company, Rockford, Ill.

A human antibody that specifically binds CD22 can be labeled with a detectable moiety. For example, the antibodies can be covalently or non-covalently linked to a detectable label. Detectable labels suitable for such use include any composition detectable by spectroscopic, photochemical, biochemical, immunochemical, electrical, optical or chemical means.

Useful detection agents include fluorescent compounds, including fluorescein, fluorescein isothiocyanate, rhodamine, 5-dimethylamine-1-napthalenesulfonyl chloride, phycoerythrin, lanthanide phosphors and the like. Bioluminescent markers are also of use, such as luciferase, Green fluorescent protein (GFP), Yellow fluorescent protein (YFP). An antibody can also be labeled with enzymes that are useful for detection, such as horseradish peroxidase, β-galactosidase, luciferase, alkaline phosphatase, glucose oxidase and the like. When an antibody is labeled with a detectable enzyme, it can be detected by adding additional reagents that the enzyme uses to produce a reaction product that can be discerned. For example, when the agent horseradish peroxidase is present, the addition of hydrogen peroxide and diaminobenzidine leads to a colored reaction product, which is visually detectable. An antibody may also be labeled with biotin, and detected through indirect measurement of avidin or streptavidin binding. It should be noted that the avidin itself can be labeled with an enzyme or a fluorescent label.

An antibody may be labeled with a magnetic agent, such as gadolinium. Antibodies can also be labeled with lanthanides (such as europium and dysprosium), and manganese. Paramagnetic particles such as superparamagnetic iron oxide are also of use as labels. An antibody may also be labeled with a predetermined polypeptide epitopes recognized by a secondary reporter (such as leucine zipper pair sequences, binding sites for secondary antibodies, metal binding domains, epitope tags). In some embodiments, labels are attached by spacer arms of various lengths to reduce potential steric hindrance.

An antibody can also be labeled with a radiolabeled amino acid. The radiolabel may be used for both diagnostic and therapeutic purposes. For instance, the radiolabel may be used to detect CD22 by x-ray, emission spectra, or other diagnostic techniques. Examples of labels for polypeptides include, but are not limited to, the following radioisotopes or radionucleotides: $^{3}H$, $^{14}C$, $^{15}N$, $^{35}S$, $^{90}Y$, $^{99}Tc$, $^{111}In$, $^{125}I$, $^{131}I$.

Means of detecting such labels are well known to those of skill in the art. Thus, for example, radiolabels may be detected using photographic film or scintillation counters, fluorescent markers may be detected using a photodetector to detect emitted illumination. Enzymatic labels are typically detected by providing the enzyme with a substrate and detecting the reaction product produced by the action of the enzyme on the substrate, and colorimetric labels are detected by simply visualizing the colored label.

An antibody can also be derivatized with a chemical group such as polyethylene glycol (PEG), a methyl or ethyl group, or a carbohydrate group. These groups may be useful to improve the biological characteristics of the antibody, such as to increase serum half-life or to increase tissue binding.

Toxins can be employed with the CD22-specific human monoclonal antibodies described herein to produce immunotoxins. Exemplary toxins include ricin, abrin, diphtheria toxin and subunits thereof, as well as botulinum toxins A through F. These toxins are readily available from commercial sources (for example, Sigma Chemical Company, St. Louis, Mo.). Contemplated toxins also include variants of the toxins described herein (see, for example, see, U.S. Pat. Nos. 5,079,163 and 4,689,401). In one embodiment, the toxin is Pseudomonas exotoxin (PE) (U.S. Pat. No. 5,602,095). As used herein "Pseudomonas exotoxin" refers to a full-length native (naturally occurring) PE or a PE that has been modified. Such modifications can include, but are not limited to, elimination of domain Ia, various amino acid deletions in domains Ib, II and III, single amino acid substitutions and the addition of one or more sequences at the carboxyl terminus (for example, see Siegall et al., *J. Biol. Chem.* 264:14256-14261, 1989). In one embodiment, the cytotoxic fragment of PE retains at least 50%, at least 75%, at least 90%, or at least 95% of the cytotoxicity of native PE. In some examples, the cytotoxic fragment is more toxic than native PE.

Native *Pseudomonas* exotoxin A (PE) is an extremely active monomeric protein (molecular weight 66 kD), secreted by *Pseudomonas aeruginosa*, which inhibits protein synthesis in eukaryotic cells. The method of PE action is inactivation of the ADP-ribosylation of elongation factor 2 (EF-2). The exotoxin contains three structural domains that act in concert to cause cytotoxicity. Domain 1a mediates cell binding. Domain II is responsible for translocation into the cytosol and domain III mediates ADP ribosylation of elongation factor 2. The function of domain Ib is unknown. PE employed with the monoclonal antibodies described herein can include the native sequence, cytotoxic fragments of the native sequence, and conservatively modified variants of native PE and its cytotoxic fragments. Cytotoxic fragments of PE include those which are cytotoxic with or without subsequent proteolytic or other processing in the target cell. Cytotoxic fragments of PE include PE40, PE38, and PE35. For additional description of PE and variants thereof, see for example, U.S. Pat. Nos. 4,892,827; 5,512,658; 5,602,095; 5,608,039; 5,821,238; and 5,854,044; PCT Publication No. WO 99/51643; Pal et al., *Proc. Natl. Acad. Sci. USA* 88:3358-3362, 1991; Kondo et al., *J. Biol. Chem.* 263:9470-9475, 1988; Pastan et al., *Biochim. Biophys. Acta* 1333:C1-C6, 1997.

The CD22-specific antibodies described herein can also be used to target any number of different diagnostic or therapeutic compounds to cells expressing CD22 on their surface. This can be done for research or therapeutic purposes. Thus, an antibody of the present disclosure can be attached directly or via a linker to a drug that is to be delivered directly to cells expressing cell-surface CD22. Therapeutic agents include such compounds as nucleic acids, proteins, peptides, amino acids or derivatives, glycoproteins, radioisotopes, lipids, carbohydrates, or recombinant viruses. Nucleic acid therapeutic and diagnostic moieties include antisense nucleic acids, derivatized oligonucleotides for covalent cross-linking with single or duplex DNA, and triplex forming oligonucleotides.

Alternatively, the molecule linked to an anti-CD22 antibody can be an encapsulation system, such as a liposome or micelle that contains a therapeutic composition such as a drug, a nucleic acid (for example, an antisense nucleic acid), or another therapeutic moiety that is preferably shielded from direct exposure to the circulatory system. Means of preparing liposomes attached to antibodies are well known to those of skill in the art (see, for example, U.S. Pat. No. 4,957,735; Connor et al., *Pharm. Ther.* 28:341-365, 1985).

V. CD22 Antibody Polynucleotides and Polypeptides

Nucleic acid molecules (also referred to as polynucleotides) encoding the polypeptides provided herein (including, but not limited to antibodies, immunoconjugates and fusion proteins) can readily be produced by one of skill in the art, using the amino acid sequences provided herein, sequences available in the art, and the genetic code. In addition, one of skill can readily construct a variety of clones containing functionally equivalent nucleic acids, such as nucleic acids which differ in sequence but which encode the same effector molecule or antibody sequence. Thus, nucleic acids encoding antibodies, conjugates and fusion proteins are provided herein.

In some embodiments, the nucleotide sequence of the heavy chain of the CD22-specific human monoclonal antibody comprises SEQ ID NO: 7, or a portion thereof (such as a portion that encodes one or more CDRs). In other embodiments, the nucleotide sequence of the heavy chain of the CD22-specific human monoclonal antibody comprises SEQ ID NO: 9, or a portion thereof. In some embodiments, the nucleotide sequence of the light chain of the CD22-specific human monoclonal antibody comprises SEQ ID NO: 8, or a portion thereof (such as a portion that encodes one or more CDRs). In other embodiments, the nucleotide sequence of the light chain of the CD22-specific human monoclonal antibody comprises SEQ ID NO: 10, or a portion thereof.

Nucleic acid sequences encoding the human antibodies that specifically bind CD22 can be prepared by any suitable method including, for example, cloning of appropriate sequences or by direct chemical synthesis by methods such as the phosphotriester method of Narang et al., *Meth. Enzymol.* 68:90-99, 1979; the phosphodiester method of Brown et al., *Meth. Enzymol.* 68:109-151, 1979; the diethylphosphoramidite method of Beaucage et al., *Tetra. Lett.* 22:1859-1862, 1981; the solid phase phosphoramidite triester method described by Beaucage & Caruthers, *Tetra. Letts.* 22(20):1859-1862, 1981, for example, using an automated synthesizer as described in, for example, Needham-VanDevanter et al., *Nucl. Acids Res.* 12:6159-6168, 1984; and, the solid support method of U.S. Pat. No. 4,458,066. Chemical synthesis produces a single stranded oligonucleotide. This can be converted into double stranded DNA by hybridization with a complementary sequence, or by polymerization with a DNA polymerase using the single strand as a template. One of skill would recognize that while chemical synthesis of DNA is generally limited to sequences of about 100 bases, longer sequences may be obtained by the ligation of shorter sequences.

Exemplary nucleic acids encoding human antibodies that specifically bind CD22 can be prepared by cloning techniques. Examples of appropriate cloning and sequencing techniques, and instructions sufficient to direct persons of skill through many cloning exercises are found in Sambrook et al., supra, Berger and Kimmel (eds.), supra, and Ausubel, supra. Product information from manufacturers of biological reagents and experimental equipment also provide useful information. Such manufacturers include the SIGMA Chemical Company (Saint Louis, Mo.), R&D Systems (Minneapolis, Minn.), Pharmacia Amersham (Piscataway, N.J.), CLONTECH Laboratories, Inc. (Palo Alto, Calif.), Chem Genes Corp., Aldrich Chemical Company (Milwaukee, Wis.), Glen Research, Inc., GIBCO BRL Life Technologies, Inc. (Gaithersburg, Md.), Fluka Chemica-Biochemika Analytika (Fluka Chemie AG, Buchs, Switzerland), Invitrogen (Carlsbad, Calif.), and Applied Biosystems (Foster City, Calif.), as well as many other commercial sources known to one of skill.

Nucleic acids encoding native EM or anti-CD22 antibodies can be modified to form the EM, antibodies, or immunoconjugates of the present disclosure. Modification by site-directed mutagenesis is well known in the art. Nucleic acids can also be prepared by amplification methods. Amplification methods include polymerase chain reaction (PCR), the ligase chain reaction (LCR), the transcription-based amplification system (TAS), the self-sustained sequence replication system (3SR). A wide variety of cloning methods, host cells, and in vitro amplification methodologies are well known to persons of skill.

In one embodiment, immunoconjugates are prepared by inserting the cDNA which encodes a human CD22-specific monoclonal antibody into a vector which comprises the cDNA encoding the EM. The insertion is made so that the antibody and the EM are read in frame, that is in one continuous polypeptide which contains a functional antibody region and a functional EM region. In one embodiment, cDNA encoding an EM, such as a label or enzyme, is ligated to an antibody so that the EM is located at the carboxyl terminus of the antibody. In another embodiment, the EM is located at the amino terminus of the antibody. In another example, cDNA encoding the EM is ligated to a heavy chain variable region of an antibody, so that the EM is located at the carboxyl terminus of the heavy chain variable region. The heavy chain-variable region can subsequently be ligated to a light chain variable region of the antibody using disulfide bonds. In a yet another example, cDNA encoding an EM is ligated to a light chain variable region of an antibody, so that the EM is located at the carboxyl terminus of the light chain variable region. The light chain-variable region can subsequently be ligated to a heavy chain variable region of the antibody using disulfide bonds.

Once the nucleic acids encoding an EM, anti-CD22 antibody, or an immunoconjugate are isolated and cloned, the desired protein can be expressed in a recombinantly engineered cell such as bacteria, plant, yeast, insect and mammalian cells. It is expected that those of skill in the art are knowledgeable in the numerous expression systems available for expression of proteins including *E. coli*, other bacterial hosts, yeast, and various higher eukaryotic cells such as the Cos, CHO, HeLa and myeloma cell lines.

One or more DNA sequences encoding the antibody or fragment thereof can be expressed in vitro by DNA transfer into a suitable host cell. The cell may be prokaryotic or eukaryotic. The term also includes any progeny of the subject host cell. It is understood that all progeny may not be identical to the parental cell since there may be mutations that occur during replication. Methods of stable transfer, meaning that the foreign DNA is continuously maintained in the host, are known in the art. Hybridomas expressing the antibodies of interest are also encompassed by this disclosure.

The expression of nucleic acids encoding the isolated proteins described herein can be achieved by operably linking the DNA or cDNA to a promoter (which is either constitutive or inducible), followed by incorporation into an expression cassette. The cassettes can be suitable for replication and integration in either prokaryotes or eukaryotes. Typical expression cassettes contain specific sequences useful for regulation of the expression of the DNA encoding the protein. For example, the expression cassettes can include appropriate promoters, enhancers, transcription and translation terminators, initiation sequences, a start codon (i.e., ATG) in front of a protein-encoding gene, splicing signal for introns, maintenance of the correct reading frame of that gene to permit proper translation of mRNA, and stop codons.

To obtain high level expression of a cloned gene, it is desirable to construct expression cassettes which contain, at the minimum, a strong promoter to direct transcription, a ribosome binding site for translational initiation, and a transcription/translation terminator. For *E. coli*, this includes a promoter such as the T7, trp, lac, or lambda promoters, a ribosome binding site, and preferably a transcription termination signal. For eukaryotic cells, the control sequences can include a promoter and/or an enhancer derived from, for example, an immunoglobulin gene, SV40 or cytomegalovirus, and a polyadenylation sequence, and can further include splice donor and acceptor sequences. The cassettes can be transferred into the chosen host cell by well-known methods such as transformation or electroporation for *E. coli* and calcium phosphate treatment, electroporation or lipofection for mammalian cells. Cells transformed by the cassettes can be selected by resistance to antibiotics conferred by genes contained in the cassettes, such as the amp, gpt, neo and hyg genes.

When the host is a eukaryote, such methods of transfection of DNA as calcium phosphate coprecipitates, conventional mechanical procedures such as microinjection, electroporation, insertion of a plasmid encased in liposomes, or virus vectors may be used. Eukaryotic cells can also be cotransformed with polynucleotide sequences encoding the antibody, labeled antibody, or functional fragment thereof, and a second foreign DNA molecule encoding a selectable phenotype, such as the herpes simplex thymidine kinase gene. Another method is to use a eukaryotic viral vector, such as simian virus 40 (SV40) or bovine papilloma virus, to transiently infect or transform eukaryotic cells and express the protein (see for example, *Eukaryotic Viral Vectors*, Cold Spring Harbor Laboratory, Gluzman ed., 1982). One of skill in the art can readily use an expression systems such as plasmids and vectors of use in producing proteins in cells including higher eukaryotic cells such as the Cos, CHO, HeLa and myeloma cell lines.

Modifications can be made to a nucleic acid encoding a polypeptide described herein (i.e., a human CD22-specific monoclonal antibody or an immunoconjugate comprising the antibody) without diminishing its biological activity. Some modifications can be made to facilitate the cloning, expression, or incorporation of the targeting molecule into a fusion protein. Such modifications are well known to those of skill in the art and include, for example, termination codons, a methionine added at the amino terminus to provide an initiation, site, additional amino acids placed on either terminus to create conveniently located restriction sites, or additional amino acids (such as poly His) to aid in purification steps. In addition to recombinant methods, the immunoconjugates, effector moieties, and antibodies of the present disclosure can also be constructed in whole or in part using standard peptide synthesis well known in the art.

Once expressed, the recombinant immunoconjugates, antibodies, and/or effector molecules can be purified according to standard procedures of the art, including ammonium sulfate precipitation, affinity columns, column chromatography, and the like (see, generally, R. Scopes, PROTEIN PURIFICATION, Springer-Verlag, N. Y., 1982). The antibodies, immunoconjugates and effector molecules need not be 100% pure. Once purified, partially or to homogeneity as desired, if to be used therapeutically, the polypeptides should be substantially free of endotoxin.

Methods for expression of antibodies and/or refolding to an appropriate active form, including single chain antibodies, from bacteria such as *E. coli* have been described and are well-known and are applicable to the antibodies disclosed herein. See, Buchner et al., *Anal. Biochem.* 205:263-270, 1992; Pluckthun, *Biotechnology* 9:545, 1991; Huse et al., *Science* 246:1275, 1989 and Ward et al., *Nature* 341:544, 1989.

Often, functional heterologous proteins from *E. coli* or other bacteria are isolated from inclusion bodies and require solubilization using strong denaturants, and subsequent refolding. During the solubilization step, as is well known in the art, a reducing agent must be present to separate disulfide bonds. An exemplary buffer with a reducing agent is: 0.1 M Tris pH 8, 6 M guanidine, 2 mM EDTA, 0.3 M DTE (dithioerythritol). Reoxidation of the disulfide bonds can occur in the presence of low molecular weight thiol reagents in reduced and oxidized form, as described in Saxena et al., *Biochemistry* 9: 5015-5021, 1970, and especially as described by Buchner et al., supra.

Renaturation is typically accomplished by dilution (for example, 100-fold) of the denatured and reduced protein into refolding buffer. An exemplary buffer is 0.1 M Tris, pH 8.0, 0.5 M L-arginine, 8 mM oxidized glutathione (GSSG), and 2 mM EDTA.

As a modification to the two chain antibody purification protocol, the heavy and light chain regions are separately solubilized and reduced and then combined in the refolding solution. An exemplary yield is obtained when these two proteins are mixed in a molar ratio such that a 5 fold molar excess of one protein over the other is not exceeded. Excess oxidized glutathione or other oxidizing low molecular weight compounds can be added to the refolding solution after the redox-shuffling is completed.

In addition to recombinant methods, the antibodies, labeled antibodies and functional fragments thereof that are disclosed herein can also be constructed in whole or in part using standard peptide synthesis. Solid phase synthesis of the polypeptides of less than about 50 amino acids in length can be accomplished by attaching the C-terminal amino acid of the sequence to an insoluble support followed by sequential addition of the remaining amino acids in the sequence. Techniques for solid phase synthesis are described by Barany & Merrifield, *The Peptides: Analysis, Synthesis, Biology. Vol. 2: Special Methods in Peptide Synthesis, Part A.* pp. 3-284; Merrifield et al., *J. Am. Chem. Soc.* 85:2149-2156, 1963, and Stewart et al., *Solid Phase Peptide Synthesis*, 2nd ed., Pierce Chem. Co., Rockford, Ill., 1984. Proteins of greater length may be synthesized by condensation of the amino and carboxyl termini of shorter fragments. Methods of forming peptide bonds by activation of a carboxyl terminal end (such as by the use of the coupling reagent N,N'-dicylohexylcarbodimide) are well known in the art.

VI. Compositions and Therapeutic Methods

Compositions are provided that include one or more of the antibodies that specifically bind CD22 that are disclosed herein in a carrier. Compositions comprising EMs, such as immunoconjugates or immunotoxins, are also provided. The compositions can be prepared in unit dosage forms for administration to a subject. The amount and timing of administration are at the discretion of the treating physician to achieve the desired purposes. The antibody can be formulated for systemic or local (such as intra-tumor) administration. In one example, the antibody that specifically binds CD22 is formulated for parenteral administration, such as intravenous administration.

The compositions for administration can include a solution of the antibody that specifically binds CD22 dissolved in a pharmaceutically acceptable carrier, such as an aqueous carrier. A variety of aqueous carriers can be used, for example, buffered saline and the like. These solutions are sterile and generally free of undesirable matter. These compositions may be sterilized by conventional, well known sterilization techniques. The compositions may contain pharmaceutically acceptable auxiliary substances as required to approximate physiological conditions such as pH adjusting and buffering agents, toxicity adjusting agents and the like, for example, sodium acetate, sodium chloride, potassium chloride, calcium chloride, sodium lactate and the like. The concentration of antibody in these formulations can vary widely, and will be selected primarily based on fluid volumes, viscosities, body weight and the like in accordance with the particular mode of administration selected and the subject's needs.

A typical pharmaceutical composition for intravenous administration includes about 0.1 to 10 mg of antibody per subject per day. Dosages from 0.1 up to about 100 mg per subject per day, such as 0.5 to 50 mg per day or 0.5 to 15 mg per day, may be used, particularly if the agent is administered to a secluded site and not into the circulatory or lymph system, such as into a body cavity or into a lumen of an organ. Actual methods for preparing administrable compositions will be known or apparent to those skilled in the art and are described in more detail in such publications as *Remington's Pharmaceutical Science*, 19th ed., Mack Publishing Company, Easton, Pa. (1995).

Antibodies may be provided in lyophilized form and rehydrated with sterile water before administration, although they are also provided in sterile solutions of known concentration. The antibody solution is then added to an infusion bag containing 0.9% sodium chloride, USP, and typically administered at a dosage of from 0.5 to 15 mg/kg of body weight. Considerable experience is available in the art in the administration of antibody drugs, which have been marketed in the U.S. since the approval of RITUXAN® in 1997. Antibodies can be administered by slow infusion, rather than in an intravenous push or bolus. In some cases, a higher loading dose is administered, with subsequent, maintenance doses being administered at a lower level. For example, an initial loading dose of 4 mg/kg may be infused over a period of some 90 minutes, followed by weekly maintenance doses for 4-8 weeks of 2 mg/kg infused over a 30 minute period if the previous dose was well tolerated.

The antibody that specifically binds CD22 can be administered to slow or inhibit the growth or replication of cells, such as malignant B cells. In these applications, a therapeutically effective amount of an antibody is administered to a subject in an amount sufficient to inhibit the progression of a B-cell malignancy, or to inhibit a sign or a symptom of the B-cell malignancy. Suitable subjects may include those diagnosed with a B-cell malignancy, such as, but not limited to, non-Hodgkin's lymphoma, Burkitt's lymphoma, small lymphocytic lymphoma, primary effusion lymphoma, diffuse large B-cell lymphoma, splenic marginal zone lymphoma, MALT (mucosa-associated lymphoid tissue) lymphoma, hairy cell leukemia, chronic lymphocytic leukemia or B-cell prolymphocytic leukemia.

A therapeutically effective amount of a human CD22-specific antibody will depend upon the severity of the disease and the general state of the patient's health. A therapeutically effective amount of the antibody is that which provides either subjective relief of a symptom(s) or an objectively identifiable improvement as noted by the clinician or other qualified observer. These compositions can be administered in conjunction with another chemotherapeutic agent, either simultaneously or sequentially.

Many chemotherapeutic agents are presently known in the art. In one embodiment, the chemotherapeutic agents is selected from the group consisting of mitotic inhibitors, alkylating agents, anti-metabolites, intercalating antibiotics, growth factor inhibitors, cell cycle inhibitors, enzymes, topoisomerase inhibitors, anti-survival agents, biological response modifiers, anti-hormones, e.g. anti-androgens, and anti-angiogenesis agents.

Single or multiple administrations of the compositions are administered depending on the dosage and frequency as required and tolerated by the patient. In any event, the composition should provide a sufficient quantity of at least one of the antibodies or immunoconjugates disclosed herein to effectively treat the patient. The dosage can be administered once but may be applied periodically until either a therapeutic result is achieved or until side effects warrant discontinuation of therapy. In one example, a dose of the antibody is infused for thirty minutes every other day. In this example, about one to about ten doses can be administered, such as three or six doses can be administered every other day. In a further example, a continuous infusion is administered for about five to about ten days. The subject can be treated at regular intervals, such as monthly, until a desired therapeutic result is achieved. Generally, the dose is sufficient to treat or ameliorate symptoms or signs of disease without producing unacceptable toxicity to the patient.

Controlled release parenteral formulations can be made as implants, oily injections, or as particulate systems. For a broad overview of protein delivery systems see, Banga, A. J., *Therapeutic Peptides and Proteins: Formulation, Processing, and Delivery Systems*, Technomic Publishing Company, Inc., Lancaster, Pa., (1995). Particulate systems include microspheres, microparticles, microcapsules, nanocapsules, nanospheres, and nanoparticles. Microcapsules contain the therapeutic protein, such as a cytotoxin, antibody or a drug, as a central core. In microspheres the therapeutic is dispersed throughout the particle. Particles, microspheres, and microcapsules smaller than about 1 µm are generally referred to as nanoparticles, nanospheres, and nanocapsules, respectively. Capillaries have a diameter of approximately 5 µm so that only nanoparticles are administered intravenously. Microparticles are typically around 100 µm in diameter and are administered subcutaneously or intramuscularly. See, for example, Kreuter, J., *Colloidal Drug Delivery Systems*, J. Kreuter, ed., Marcel Dekker, Inc., New York, N.Y., pp. 219-342 (1994); and Tice & Tabibi, *Treatise on Controlled Drug Delivery*, A. Kydonieus, ed., Marcel Dekker, Inc. New York, N.Y., pp. 315-339, (1992).

Polymers can be used for ion-controlled release of the antibody compositions disclosed herein. Various degradable and nondegradable polymeric matrices for use in controlled drug delivery are known in the art (Langer, *Accounts Chem. Res.* 26:537-542, 1993). For example, the block copolymer, polaxamer 407, exists as a viscous yet mobile liquid at low temperatures but forms a semisolid gel at body temperature. It has been shown to be an effective vehicle for formulation and sustained delivery of recombinant interleukin-2 and urease (Johnston et al., *Pharm. Res.* 9:425-434, 1992; and Pec et al., *J. Parent. Sci. Tech.* 44(2):58-65, 1990). Alternatively, hydroxyapatite has been used as a microcarrier for controlled release of proteins (Ijntema et al., *Int. J. Pharm.* 112:215-224, 1994). In yet another aspect, liposomes are used for controlled release as well as drug targeting of the lipid-capsulated drug (Betageri et al., *Liposome Drug Delivery Systems*, Technomic Publishing Co., Inc., Lancaster, Pa. (1993)). Numerous additional systems for controlled delivery of therapeutic proteins are known (see U.S. Pat. No. 5,055,303; U.S. Pat. No. 5,188,837; U.S. Pat. No. 4,235,871; U.S. Pat. No. 4,501,728; U.S. Pat. No. 4,837,028; U.S. Pat. No. 4,957,735; U.S. Pat. No. 5,019,369; U.S. Pat. No. 5,055,303; U.S. Pat. No. 5,514,670; U.S. Pat. No. 5,413,797; U.S. Pat. No. 5,268,164; U.S. Pat. No. 5,004,697; U.S. Pat. No. 4,902,505; U.S. Pat. No. 5,506,206; U.S. Pat. No. 5,271,961; U.S. Pat. No. 5,254,342 and U.S. Pat. No. 5,534,496).

VI. Diagnostic Methods and Kits

A method is provided herein for the detection of expression of CD22 in vitro or in vivo. In one example, expression of CD22 is detected in a biological sample. The sample can be any sample, including, but not limited to, tissue from biopsies, autopsies and pathology specimens. Biological samples also include sections of tissues, for example, frozen sections taken for histological purposes. Biological samples further include body fluids, such as blood, serum, plasma, sputum, spinal fluid or urine. A biological sample is typically obtained from a mammal, such as a rat, mouse, cow, dog, guinea pig, rabbit, or primate. In one embodiment, the primate is a human.

In several embodiments, a method is provided for detecting a B-cell malignancy such as non-Hodgkin's lymphoma, Burkitt's lymphoma, small lymphocytic lymphoma, primary effusion lymphoma, diffuse large B-cell lymphoma, splenic marginal zone lymphoma, MALT lymphoma, hairy cell leukemia, chronic lymphocytic leukemia or B-cell prolymphocytic leukemia. CD22 is expressed in 60-70% of B cell lymphomas and leukemias. Thus, CD22-specific antibodies can be used to detect the number of cells expressing CD22 in a blood sample from a subject to detect a B-cell malignancy in the subject, or to confirm a diagnosis of a B-cell malignancy in a subject.

The invention provides a method for detecting CD22 in a biological sample. In one embodiment, the biological sample comprises PBMCs collected from a subject. The method for detecting CD22 includes contacting a biological sample with a human antibody that binds CD22 under conditions conducive to the formation of an immune complex, and detecting the immune complex, to detect the CD22 in the biological sample. In one example, an increase in the number of CD22-positive cells in the sample indicates that the subject has a B-cell malignancy. In another example, detecting an increase in the number of CD22-positive cells in the sample confirms a diagnosis of a B-cell malignancy in a subject.

It has also been demonstrated that soluble forms of CD22 can be detected and quantified in body fluid samples, such as serum or blood samples, from subjects with B-cell malignancies (see, for example, U.S. Patent Application Publication No. 2005/0244828). The major species of sCD22 protein is about 100 kDa, which is smaller than the reported size of the membrane-bound CD22 antigen (135 kDa). Levels of sCD22 are elevated in subjects with B-cell malignancies, such as CLL and HCL, as compared to sCD22 levels in healthy individuals. In addition, levels of sCD22 correlate well to tumor burden in subjects with CLL and HCL, and sCD22 levels decrease with effective cancer therapies.

In general, relative levels of sCD22 in serum samples can be measured against reference serum baselines from subjects free from B-cell malignancy in order to provide a framework for determining normal CD22 levels versus elevated CD22 levels. Thus, an elevated sCD22 level in a subject as compared to a control indicates the presence of a B-cell malignancy.

Additionally, sCD22 levels can be monitored periodically in subjects with B-cell malignancy as they undergo successive rounds of cancer therapy. A lowered (or lowering) sCD22 level is an indicator of therapeutic effectiveness. Conversely, elevated sCD22 indicates that a particular therapeutic intervention is ineffective at treating the cancer. Similarly, the absence of a decline in sCD22 is also an indication that tumor burden is not declining in response to this therapy. Thus, sCD22 levels can be used to make decisions regarding choice of therapy, as well as to diagnose or prognose development or progression of a B-cell malignancy.

Soluble CD22 levels are also useful as for the screening of new anti-cancer therapeutic compounds. For instance, potential therapeutic compounds are administered to a subject with a B-cell lymphoma or leukemia, and the therapeutic efficacy of the compounds is ascertained by monitoring sCD22 levels in the subject over time. Efficacy is determined as discussed above for treatments.

In one embodiment, the human antibody that specifically binds CD22 is directly labeled with a detectable label. In another embodiment, the human antibody that specifically binds CD22 (the first antibody) is unlabeled and a second antibody or other molecule that can bind the human antibody that specifically binds CD22 is labeled. As is well known to one of skill in the art, a second antibody is chosen that is able to specifically bind the specific species and class of the first antibody. For example, if the first antibody is a human IgG, then the secondary antibody may be an anti-human-lgG. Other molecules that can bind to antibodies include, without limitation, Protein A and Protein G, both of which are available commercially.

Suitable labels for the antibody or secondary antibody are described above, and include various enzymes, prosthetic groups, fluorescent materials, luminescent materials, magnetic agents and radioactive materials. Non-limiting examples of suitable enzymes include horseradish peroxidase, alkaline phosphatase, beta-galactosidase, or acetylcholinesterase. Non-limiting examples of suitable prosthetic group complexes include streptavidin/biotin and avidin/biotin. Non-limiting examples of suitable fluorescent materials include umbelliferone, fluorescein, fluorescein isothiocyanate, rhodamine, dichlorotriazinylamine fluorescein, dansyl chloride or phycoerythrin. A non-limiting exemplary luminescent material is luminol; a non-limiting exemplary a magnetic agent is gadolinium, and non-limiting exemplary radioactive labels include $^{125}$I, $^{131}$I, $^{35}$S or $^{3}$H.

In an alternative embodiment, CD22 can be assayed in a biological sample by a competition immunoassay utilizing CD22 standards labeled with a detectable substance and an unlabeled human antibody that specifically binds CD22. In this assay, the biological sample, the labeled CD22 standards and the human antibody that specifically bind CD22 are combined and the amount of labeled CD22 standard bound to the unlabeled antibody is determined. The amount of CD22 in the biological sample is inversely proportional to the amount of labeled CD22 standard bound to the antibody that specifically binds CD22.

The methods disclosed herein can be used for a number of purposes. In one embodiment, the human antibody that specifically binds CD22 can be used to detect the production of CD22 in cells in cell culture, or the expression of CD22 on the surface of cells in culture. In another embodiment, the antibody can be used to detect the amount of CD22 in a biological sample, the number of cells in a sample that express CD22, or the level of expression of CD22 in a cell population. In one embodiment, the antibodies described herein can be used to detect the presence of sCD22 in a biological sample, such as a blood or serum sample.

CD22 is expressed in 60-70% of all B-cell malignancies. In addition, sCD22 has been detected in the serum or blood of patients diagnosed with B-cell malignancies. In one embodiment, a kit is provided for detecting CD22 in a biological sample, such as a blood sample. For example, to confirm a B-cell malignancy diagnosis in a subject, a blood sample can be obtained from the subject, PBMCs from the sample isolated, and the cells evaluated for expression of CD22, particularly for the number of cells expressing CD22. In another example, a B-cell malignancy diagnosis is confirmed by obtaining a blood sample from a subject and detecting sCD22 in the sample. An increased level of sCD22 relative to a control subject, or a known standard, confirms the B-cell malignancy diagnosis.

Kits for detecting a CD22 polypeptide, including cytoplasmic CD22, cell-surface CD22 and/or sCD22, will typically comprise a human antibody that specifically binds CD22, such as any of the antibodies disclosed herein. In some embodiments, an antibody fragment, such as an Fv fragment or an Fab is included in the kit. In a further embodiment, the antibody is labeled (for example, with a fluorescent, radioactive, or an enzymatic label).

In one embodiment, a kit includes instructional materials disclosing means of use of an antibody that specifically binds CD22. The instructional materials may be written, in an electronic form (such as a computer diskette or compact disk) or may be visual (such as video files). The kits may also include additional components to facilitate the particular application for which the kit is designed. Thus, for example, the kit may additionally contain means of detecting a label (such as enzyme substrates for enzymatic labels, filter sets to detect fluorescent labels, appropriate secondary labels such as a secondary antibody, or the like). The kits may additionally include buffers and other reagents routinely used for the practice of a particular method. Such kits and appropriate contents are well known to those of skill in the art.

In one embodiment, the diagnostic kit comprises an immunoassay. Although the details of the immunoassays may vary with the particular format employed, the method of detecting CD22 in a biological sample generally includes the steps of contacting the biological sample with an antibody which specifically reacts, under immunologically reactive conditions, to a CD22 polypeptide. The antibody is allowed to specifically bind under immunologically reactive conditions to form an immune complex, and the presence of the immune complex (bound antibody) is detected directly or indirectly.

Methods of determining the presence or absence of a cell surface marker are well known in the art. For example, the antibodies can be conjugated to other compounds including, but not limited to, enzymes, magnetic beads, colloidal magnetic beads, haptens, fluorochromes, metal compounds, radioactive compounds or drugs. The antibodies can also be utilized in immunoassays such as but not limited to radioimmunoassays (RIAs), enzyme linked immunosorbent assays (ELISA), or immunohistochemical assays. The antibodies can also be used for fluorescence activated cell sorting (FACS). A FACS employs a plurality of color channels, low angle and obtuse light-scattering detection channels, and impedance channels, among other more sophisticated levels of detection, to separate or sort cells (see U.S. Pat. No. 5,061,620). Any of the human antibodies that specifically bind CD22, as disclosed herein, can be used in these assays. Thus, the antibodies can be used in a conventional immunoassay, including, without limitation, an ELISA, an RIA, FACS, tissue immunohistochemistry, Western blot or immunoprecipitation.

The following examples are provided to illustrate certain particular features and/or embodiments. These examples should not be construed to limit the disclosure to the particular features or embodiments described.

EXAMPLES

Example 1

Identification and Characterization of Human Anti-CD22 mAbs

Materials and Methods

Proteins

Soluble CD22 was purchased from PeproTech (Rocky Hill, N.J.). CD22-Fc was generated according to standard procedures. Briefly, the extracellular domain of CD22 protein was expressed as a fusion to human IgG1 Fc using pCDNA1.1-22-Fc as described previously (Ho et al., *J. Biol. Chem.* 280, 607-617, 2005). The plasmid was transfected into 293T cells by LIPOFECTAMINE™ reagent (Invitrogen, Carlsbad, Calif.), and the CD22-Fc protein was harvested from the culture supernatant and purified with a protein A column (GE Healthcare, Piscataway, N.J.). For production of CD22 sub-domain proteins, DNA fragments encoding various domains were PCR-amplified, introducing EcoRI and XhoI restriction sites into the 5 and 3' ends, respectively. The DNA fragments were then digested with both enzymes and cloned into the pSecTag2C (Invitrogen) expression vector digested with the same two enzymes. Different CD22 domains were expressed by transient transfection into 293T cells using the POLYFECT™ transfection agent (Qiagen, Hilden, Germany) according to the manufacturer's protocol.

Since the pSecTag vector has the murine kappa chain leader fused to N-terminus of the protein expressed from it, the resulting fusion protein is secreted to the supernatant. In addition, all the expressed CD22 domain proteins had c-Myc and His tags from the vector fused to their C-termini. They were used for detection in ELISA and affinity purification. Cell culture supernatant containing the secreted CD22 fragments was used directly in ELISA assay, and purified CD22 fragments were used for selecting antibodies targeting specific CD22 regions. Specifically, the CD22 fragment containing Ig-like domains 1 and 2 was purified using the Ni-NTA-agarose column (Qiagen) for selecting CD22-specific antibodies targeting this region. Briefly, supernatant from 293T cells transfected with pSecTag2C-CD22 (domains 1+2) was buffer exchanged to PBS before it was loaded on the Ni-NTA-agarose column for native purification according to the manufacture's protocol. The final product was dialyzed against PBS. Purified CD22 fragments were used in phage panning.

Cell Lines

T lymphoma cell line SupT1 and B lymphoma cell lines Raji, BJAB, and ST486 were obtained from ATCC (Manassas, Va.). SupT1 cells were maintained in RPMI containing 10% FBS, whereas the B cell lines were maintained in RPMI containing 20% FBS.

Selection of CD22 Antibody

Two different panning procedures were used to isolate anti-CD22 antibody from a human naïve Fab library (Zhu et al., *Proc. Natl. Acad. Sci. USA* 104:12123-12128, 2007). CD22-Fc and purified CD22 domains 1+2 were coated directly to Maxisorp plates (Nunc, Denmark) in PBS buffer at 40° C. overnight for the plate format panning. Soluble CD22 was labeled first with EZ-link Sulfo-NHS-LC-Biotin (Pierce, Rockford, Ill.) for the streptavidin-conjugated magnetic bead format panning. For the plate format, approximately $10^{12}$ Fabs displayed on the surface of phage amplified from the large naïve library were suspended in PBS with 2% dry milk and applied first to wells coated with irrelevant Fc fusion proteins for pre-absorption in the case of panning against CD22-Fc. After 1 hour at room temperature, phage suspension was transferred to the wells coated with CD22-Fc. After two-hour incubation at room temperature, the wells were washed and the phage was rescued with TG1 cells.

For panning against CD22 domains 1+2, the pre-incubation step with irrelevant Fc fusion protein was omitted. For the bead format, biotin-labeled CD22 were first incubated with the phage in 1 ml of a PBS+2% dry milk suspension at room temperature for 2 hours. Fifteen μl of DYNABEADS™ MyOne Streptavidin T1 (Invitrogen Dynal AS, Oslo, Norway) pre-blocked with PBS+2% dry milk was added to the antigen/phage mixture for another one hour at room temperature. The beads were then washed and phage was rescued with TG1 cells. A total of four rounds were performed for each format. Monoclonal ELISA was then performed to select for positive clones. Two hundred clones were screened from each format. One dominant positive clone from each procedure was finally selected.

Fab, IgG1, and scFv Expression and Purification

Plasmids of the positive clones were used to transform the *E. coli* strain HB2151 for Fab expression. The heavy and light chains of each clone were transferred to the pDR12 vector for making the IgG1 format of the two antibodies. To make the scFv format of the antibody, the DNA fragments encoding the heavy and light chains of the clone were linked through an overlapping PCR procedure. The resulting scFv gene had the heavy chain followed by a linker containing amino acids GGGGS (SEQ ID NO: 11), and the light chain. One SfiI restriction site was also introduced during the PCR procedure to each end of the scFv DNA fragment, which was cloned into the pComb3x vector (Scott et al., "Phage-display vector," In. Phage display: a laboratory manual. Cold Spring Harbor, New York: Cold Spring Harbor Laboratory Press, Barbas, C F, III, editor, 2001) digested with SfiI for protein expression. ScFv plasmid was used to transform *E. coli* strain HB2151 for expression. IgG1 plasmids were transiently transfected to 293 free style cells (Invitrogen) for IgG1 production. Fab and scFv were purified using the Ni-NTA agarose bead (Qiagen) and IgG1 with the protein A SEPHAROSE™ column (GE Healthcare, Piscataway, N.J.).

ELISA

CD22 or CD22-Fc in PBS was coated to a 96-well plate overnight at 4° C. The plate was then washed with PBST (PBS+0.05% Tween) and blocked with PBST supplemented with 5% dry milk. Fab, scFv or IgG1 diluted in PBST+milk was added to the wells. The Fab and scFv binding was detected using the anti-His-IgG-HRP (Qiagen) and the IgG1 binding was detected using the anti-human Fc-IgG-HRP (Sigma, St. Louis, Mo.). After washing, ABTS substrate (Roche, Mannheim, Germany) was added to each well and $OD_{405}$ was recorded after five to ten minutes. For competition ELISA, one antibody was first coated to the ELISA plate. CD22-Fc was mixed with indicated Fabs or scFv in the PBST+5% milk buffer and added to each well. The bound CD22-Fc was then detected with anti-human Fc-IgG-HRP.

Epitope Mapping

CD22 sub-domains secreted into the culture supernatant were used directly in an ELISA assay. Briefly, the testing antibodies and anti-His antibody (Qiagen) were coated to the ELISA plates. Cell culture supernatant (100 μl) containing CD22 fragments with both His and c-Myc tags were added to the pre-coated wells. After washing, anti-c-Myc-IgG-HRP was added to each well to measure the amount of CD22 fragments captured either by anti-His antibody as a measurement of expression of each CD22 fragment, or by testing antibodies as a measurement of their epitopes.

Flow Cytometry

SupT1, Raji, BJAB, and ST486 cells in suspension culture were collected by centrifugation and then re-suspended in ice-cold RPMI+10% FBS medium at a density of $1 \times 10^6$/ml. ScFv or IgG1 at different concentrations were added to the cells. Cells were left on ice for half an hour before being washed with the same complete RPMI medium. For scFv HA22, a mixture of mouse anti-His and anti-mouse-IgG-FITC was added to the cells for another half an hour on ice. For IgG1, anti-human-IgG-FITC was added to the cells. The cells were then washed with RPMI medium twice and re-suspended in PBS and subjected to flow cytometry analysis using the FACSCalibur™ (Becton Dickinson, San Jose, Calif.)

Results

Two CD22-specific Fabs were isolated. Using CD22-Fc as the panning antigen and the plate format, one dominant clone, m971, was isolated. Another clone, m972, was isolated in parallel using biotin-labeled CD22 as the panning antigen and the streptavidin bead format. The heavy and light chain amino acid sequences of m972 and m971 are shown below and are set forth herein as SEQ ID NOS: 1-4. CDR sequences are underlined. The corresponding nucleotide sequences of the heavy and light chains are set forth herein as SEQ ID NOS: 7-10.

m972 heavy chain
(SEQ ID NO: 1)
EVQLVQSGGGVVRPGGSLRLPCAAS<u>GFTFDDYGMS</u>WVRQAPGKGLEWVSG <u>INWNGGSTGYADS</u>VKGRFTISRDNAKNSLYLQMNSLRAEDTALYHC<u>ARGG</u>

<u>DDAFDI</u>WGQGTMVTVSSASTKGPSVFPLAPSSKSTSGGTAALGCLVKDYF

PEPVTVSWNSGALTSGVHTFPAVLQSSGLYSLSSVVTVPSSSLGTQTYIC

NVNHKPSNTKVDKKVEPKSCDKTSGQAG m972 light chain
(SEQ ID NO: 2)
RIVMTQSPGTLSVSPGETATLSCRAS<u>QSFSNML</u>AWYQQKSGQPPRLLIY<u>G</u>

<u>VS</u>TRAAGVPARFSGSGSGTEFTLTISNLQSEDFAVYYC<u>QQYGDWPRYT</u>FG

QGTKVERKRTVAAPSVFIFPPSDEQLKSGTASVVCLLNNFYPREAKVQWK

-continued

VDNALQSGNSQESVTEQDSKDSTYSLSSTLTLSKADYEKHKVYACEVTHQ

GLSSPVTKSFNRGEC m971 heavy chain
(SEQ ID NO: 3)
QVQLQQSGPGLVKPSQTLSLTCAIS<u>GDSVSSNSAA</u>WNWIRQSPSRGLEWL GR<u>TYYRSKWYN</u>DYAVSVKSRITINPDTSKNQFSLQLNSVTPEDTAVYYC<u>A</u>

<u>REVTGDLEDAFD</u>IWGQGTMVTVSSASTKGPSVFPLAPSSKSTSGGTAALG

CLVKDYFPEPVTVSWNSGALTSGVHTFPAVLQSSGLYSLSSVVTVPSSSL

GTQTYICNVSHKPSNTKVDKKVEPKSCDKTSGQAG m971 light chain
(SEQ ID NO: 4)
DIQMTQSPSSLSASVGDRVTITCRAS<u>QTIWSY</u>LNWYQQRPGKAPNLLIY<u>A</u>

<u>ASSLQS</u>GVPSRFSGRGSGTDFTLTISSLQAEDFATYYC<u>QQSYSIPQT</u>FGQ

GTKLEIKRTVAAPSVFIFPPSDEQLKSGTASVVCLLNNFYPREAKVQWKV

DNALQSGNSQESVTEQDSKDSTYSLSSTLTLSKADYEKHKVYACEVTHQG

LSSPVTKSFNRGEC

Figure 1B:
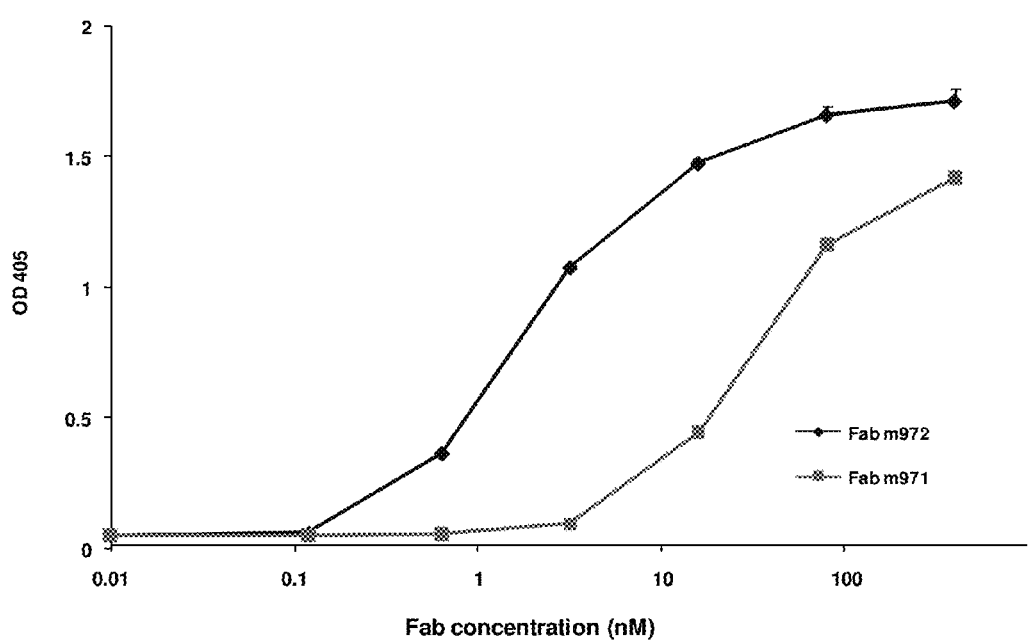
FIGS. 1B-1D are line graphs showing binding of m971 and m972 to soluble CD22. Fully human CD22 antibodies in Fab (FIG. 1B), IgG1 (FIG. 1C) and scFv (FIG. 1D) formats were purified and tested for binding to soluble CD22 by ELISA.
Figure 1C:
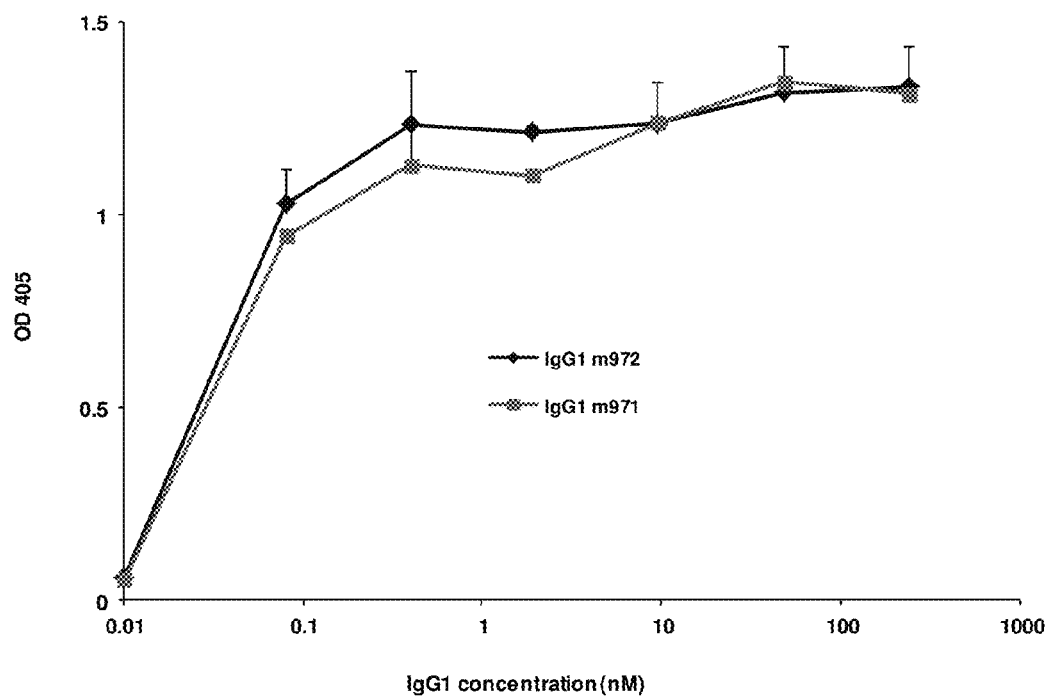
Figure 1D:
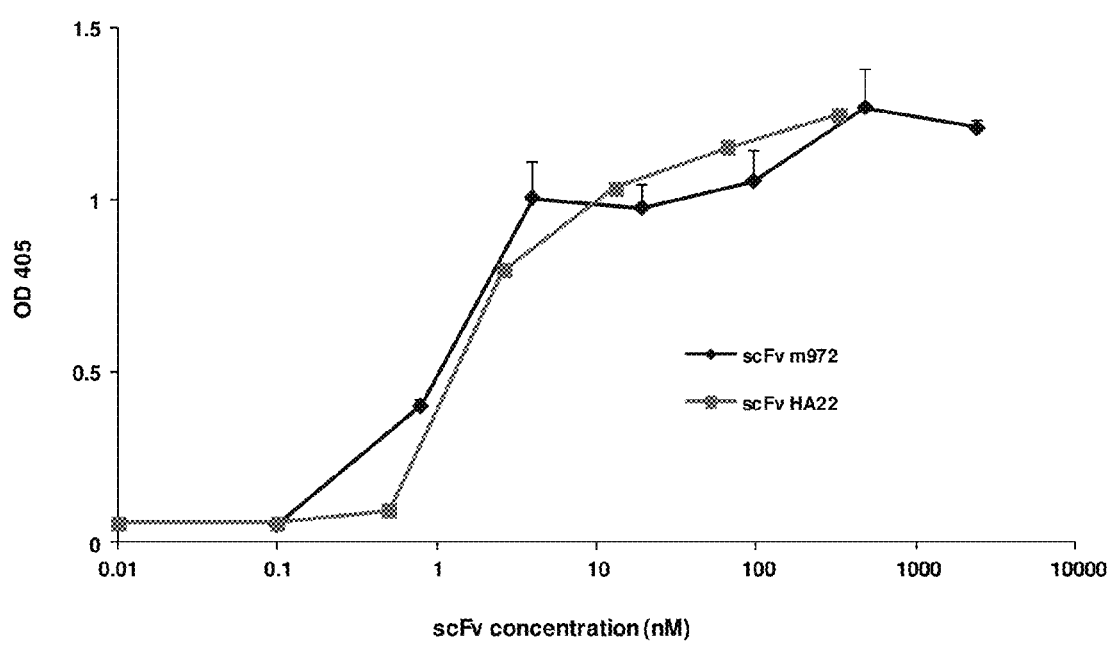
Figure 1E:
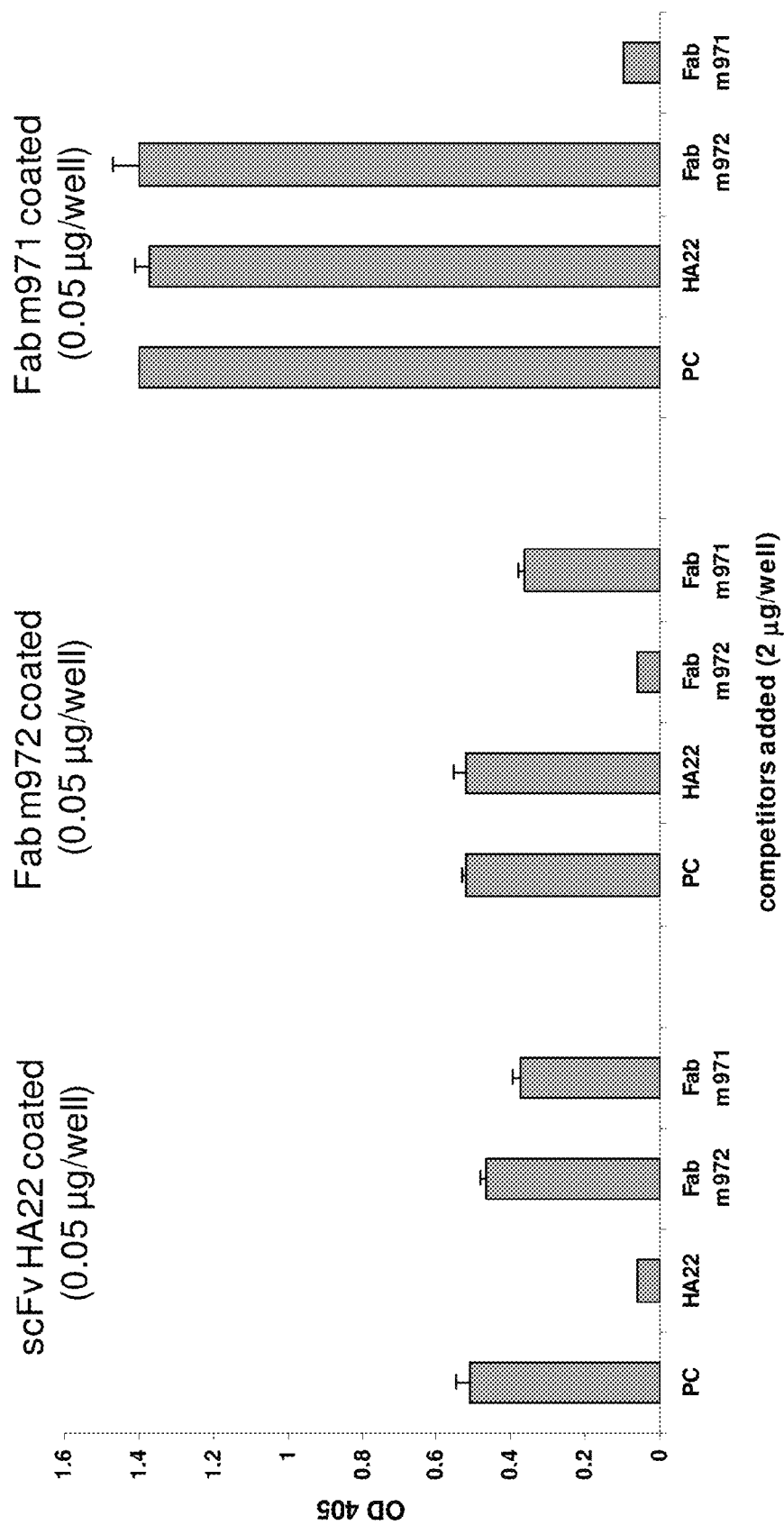
FIG. 1E is a bar graph of a competition ELISA comparing m971, m972 and HA22. ScFv HA22, Fab m972 and Fab m971 (50 ng/well) were coated to the ELISA plate and a mixture of CD22-Fc (1 µg/well) and one of the indicated antibodies was added to each well. The amount of CD22-Fc bound by the coated scFv or Fab was then detected using goat anti-human Fc-IgG-HRP. PC=no competitors added.

The clones were expressed and purified in Fab, IgG1 and, in the case of m972, scFv format (FIG. 1A). In Fab format, m972 bound CD22 ten times better than m971 with apparent EC50s of 2 and 20 nM, respectively (FIG. 1B), although the difference was less significant for their IgG1s (EC50s<1 nM) (FIG. 1C). This was probably due to the increased valency of IgG1 and the multimeric nature of CD22 (Han et al., *Nat. Chem. Biol.* 1:93-97, 2005). M972 was further converted into the scFv format; it had a similar binding affinity as its Fab format and binding was comparable to that of scFv HA22 (FIG. 1D). The two Fabs both bound to CD22-Fc, but with different profiles. As measured by ELISA, m971 bound better to CD22-Fc than both m972 and HA22, whereas m972 bound better to its selecting antigen CD22 than m971 (FIGS. 1B, 1D and 1E). This suggests that soluble CD22 purified from mammalian cells and CD22-Fc expressed from mammalian cells may adopt different conformations. It is not clear at this point if this observation has any correlation with cell surface expressed CD22, even though a report has suggested that CD22 may adopt highly flexible structures in domains 1 and 2 (Toba et al., *Exp. Hematol.* 30, 205-211, 2002). When a competition ELISA was performed among the two new Fabs and HA22 scFv, no significant cross competition was detected among them (FIG. 1E). This suggests that the two new antibodies have distinct epitopes on CD22.

Figure 2:
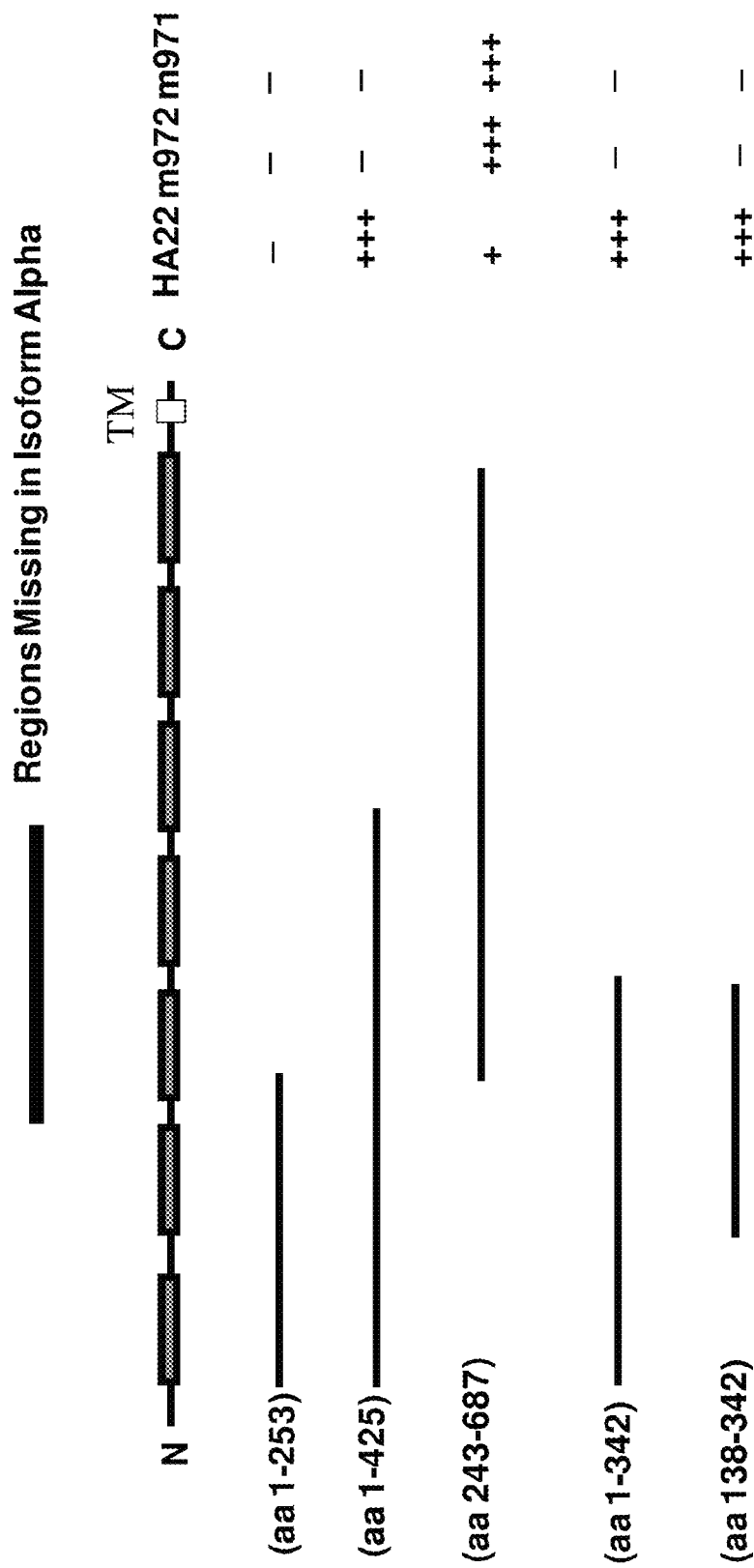
FIG. 2 is a schematic diagram illustrating epitope determination of human anti-CD22 antibodies. Sub-domains of CD22 were expressed transiently and the supernatant from transfected cells was added to ELISA plate wells coated with the three indicated antibodies. The bound CD22 domains were detected with mouse anti-Myc-IgG-HRP. The seven boxes represent the seven Immunoglobulin-like domains of CD22. Numbers in the brackets indicate the starting and ending amino acid residues of each domain construct. The symbol "+" indicates binding that is approximately 10% of binding represented by the symbol "+++". The symbol "−" indicates no binding. TM=transmembrane sequence.
Figure 3A:
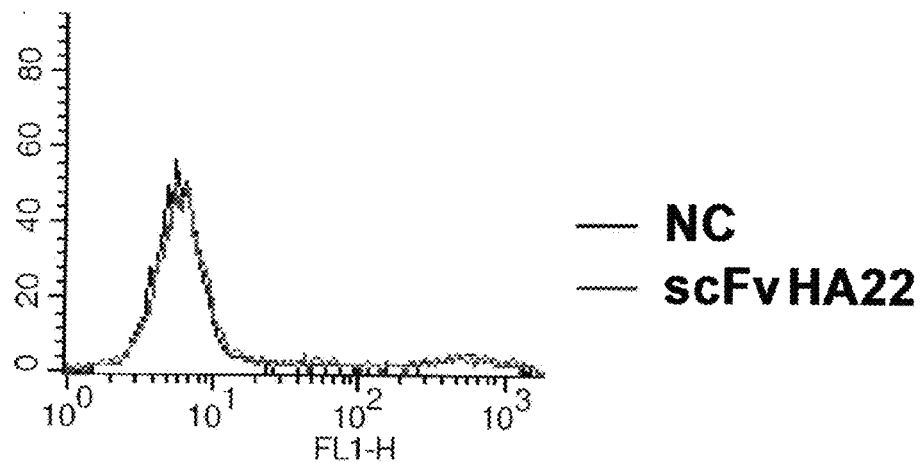
FIGS. 3A-3H are FACS plots showing detection of human CD22 antibody binding to B lymphocytes. m971, m972 and a weak CD22 binder in IgG1 format were used in flow cytometry to test their ability to recognize native, cell surface-associated CD22. HA22 in scFv format was used as the positive control. M396, a severe acute respiratory syndrome (SARS) virus-spike specific human IgG1 was used as the isotype control. An unrelated scFv was used as a negative control (NC) for HA22. SupT1 cells (FIG. 3A and FIG. 3B), which are T lymphocytes that do not express CD22, were used as the negative control cell line. Raji (FIG. 3C and FIG. 3D), BJAB (FIG. 3E and FIG. 3F) and ST486 (FIG. 3G and FIG. 3H) cells, which are B lymphoma cell lines, were used as the testing cell lines. In each histogram, cell count is shown on the y-axis and fluorescence intensity is shown on the x-axis. For each cell line, the upper panel (FIGS. 3A, 3C, 3E and 3G) shows the binding by scFv HA22 and the lower panel (FIGS. 3B, 3D, 3F and 3H) shows the binding by each human IgG1 antibody. For experiments with SupT1 and Raji cells, 10 µg/ml of each of HA22, m971, m972 and the weak CD22 binder were used. For experiments with BJAB and ST486 cells, the HA22 concentration remained the same, while 100 and 50 µg/ml were used for m971 and m972, respectively.
Figure 3B:
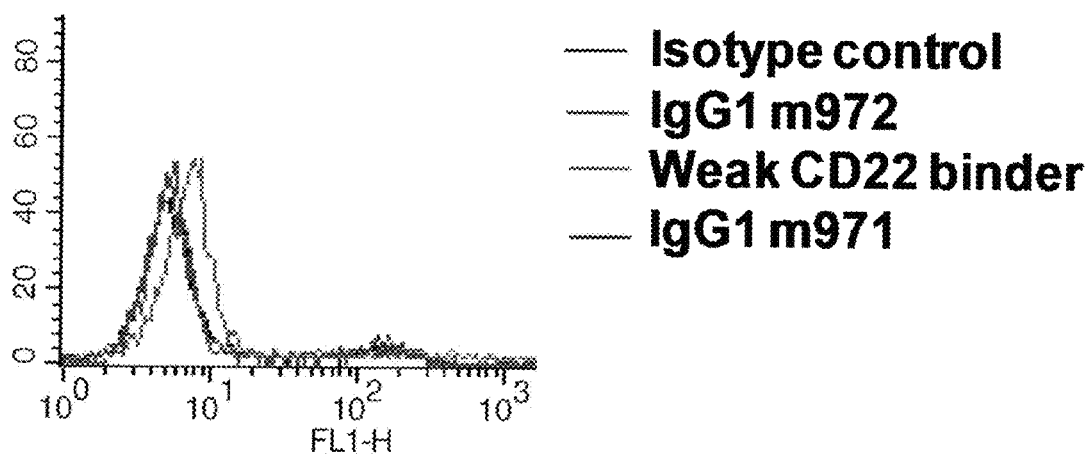
Figure 3C:
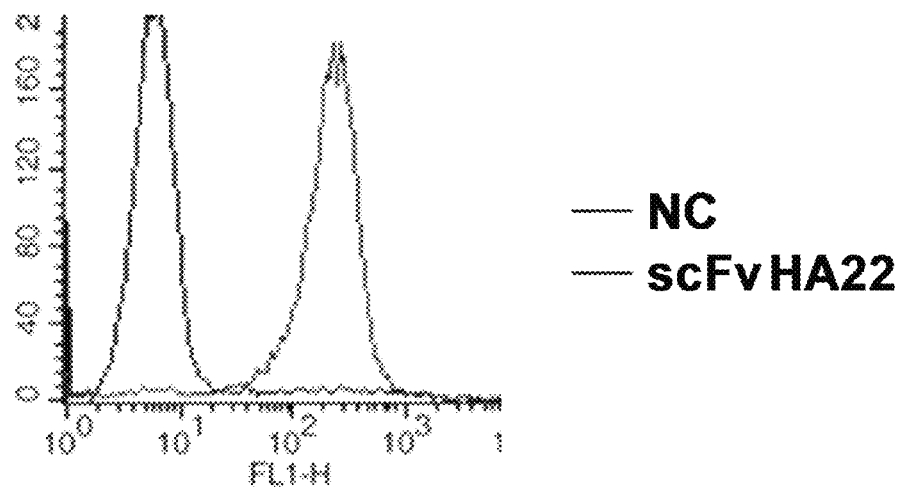
Figure 3D:
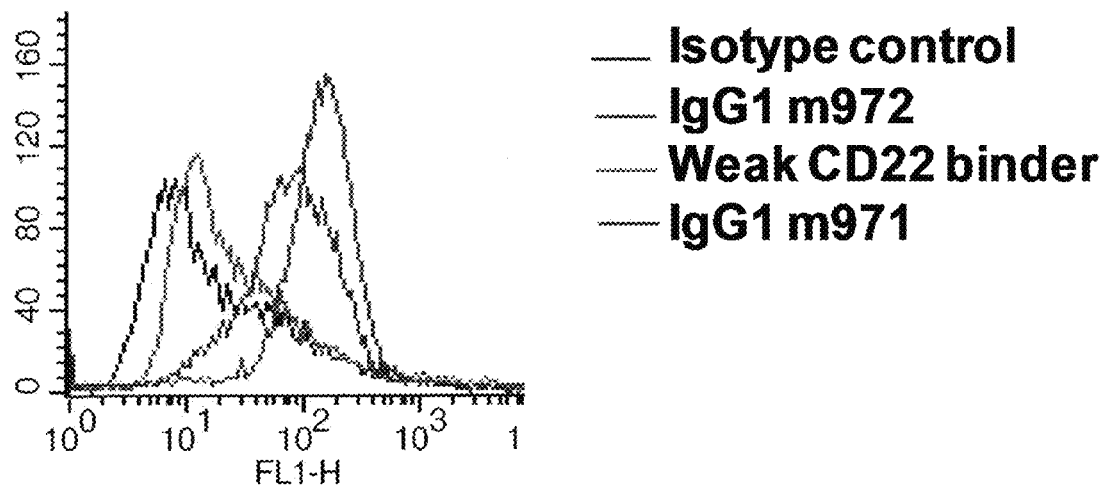
Figure 3E:
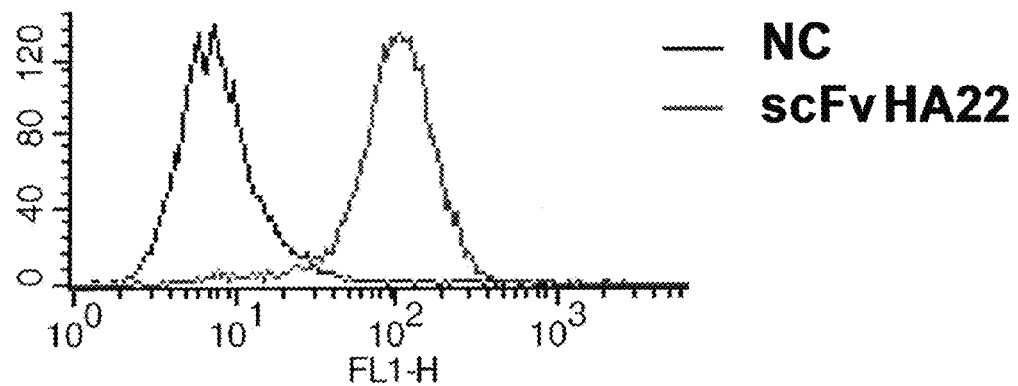
Figure 3F:
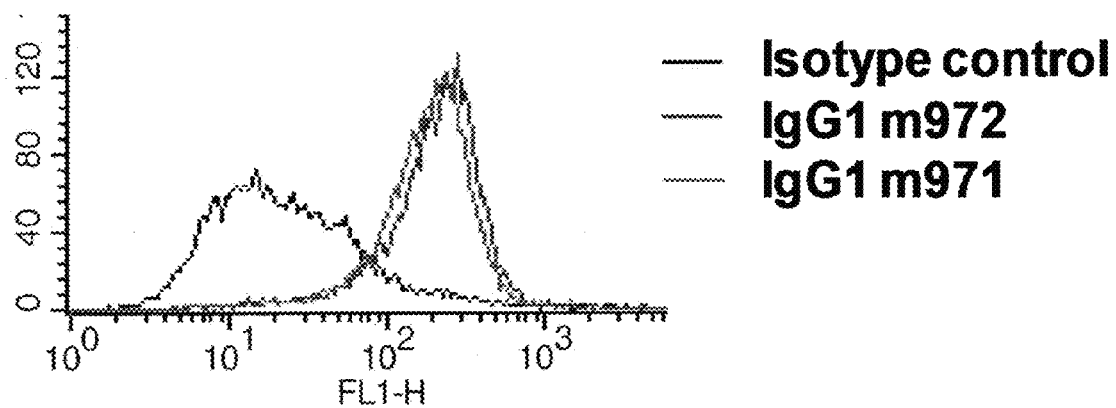
Figure 3G:
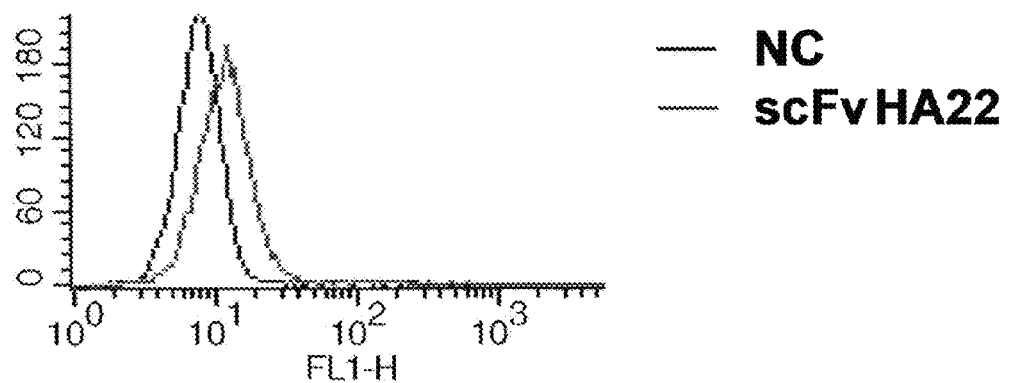
Figure 3H:
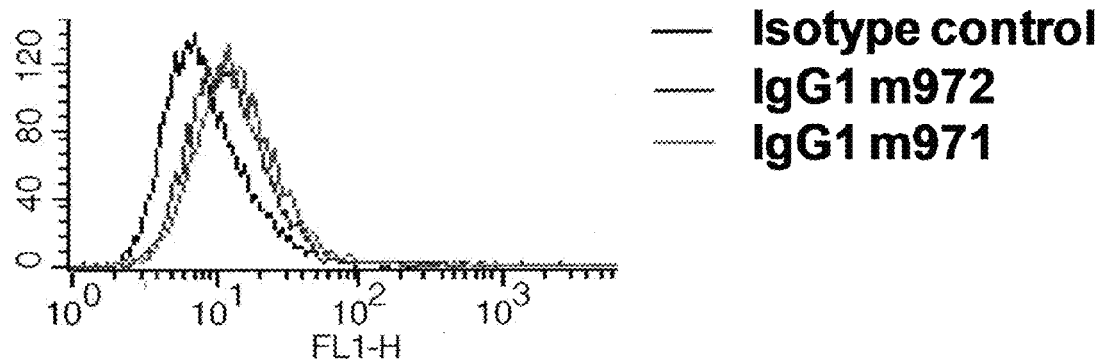

To better characterize the binding epitopes of the two antibodies, protein fragments containing different Ig-like domains of CD22 were expressed and evaluated in an ELISA. It was found that HA22 bound efficiently to CD22 fragments that included both domains 2 and 3, even though very weak binding was also detected against fragments containing only domain 3 (FIG. 2). This suggests that the HA22 epitope resides primarily in domain 3, and domain 2 is important in maintaining the integrity of the epitope. This is in agreement with the published data showing that RFB4, the parental IgG of HA22, competed partially with another mAb that binds to domain 3 (Stein et al., *Cancer Immunol. Immunother.* 37, 293-298, 1993). The two new antibodies reacted only to the region including domains 5 to 7 (FIG. 2). Since this is a rather broad region, it is not surprising that the two new antibodies do not compete with each other (FIG. 1E).

To test whether the new antibodies bind to native, cell-associated CD22, a flow cytometry assay was performed with B lymphocyte cell lines Raji, BJAB and ST486 (FIG. 3). Neither IgG1 bound to the T lymphocyte supT1 cells used as a negative control (FIG. 3). Both antibodies bound specifically as IgG1 s to the B cell lines. Specifically, when used at the same concentration (10 μg/ml), m972 bound to Raji cells better than m971. In studies using BJAB and ST486 cells, when twice as much m971 was added (100 μg/ml versus 50 μg/ml of m972), similar bindings were achieved by both (FIG. 3). These data suggest that m972 has a higher affinity to cell surface-associated CD22 compared to m971, and CD22 purified from the mammalian cells is a more accurate representation of cell surface associated CD22 than CD22-Fc fusion proteins, at least when the epitopes of the IgGs are considered. It is noteworthy that the extent to which the two human IgGs bound to the T and B cell lines closely resembled that of HA22. This is another strong indication of specific binding to cell surface CD22 by these antibodies.

In studies done in parallel to those for m971 and m972, another antibody that bound purified CD22 domains 1+2 was isolated. This molecule also recognized CD22-Fc in both Fab and IgG format specifically, albeit weakly. This antibody was referred to as "weak CD22 binder." Since it failed to show specific binding to CD22 expressing B cells (FIG. 3), further investigation was terminated. However, the binding pattern of the weak binder suggests that the domains 1+2 region is highly flexible, and significant differences exist between the in vitro-expressed and cell surface-associated CD22 domains 1+2.

Figure 4A:
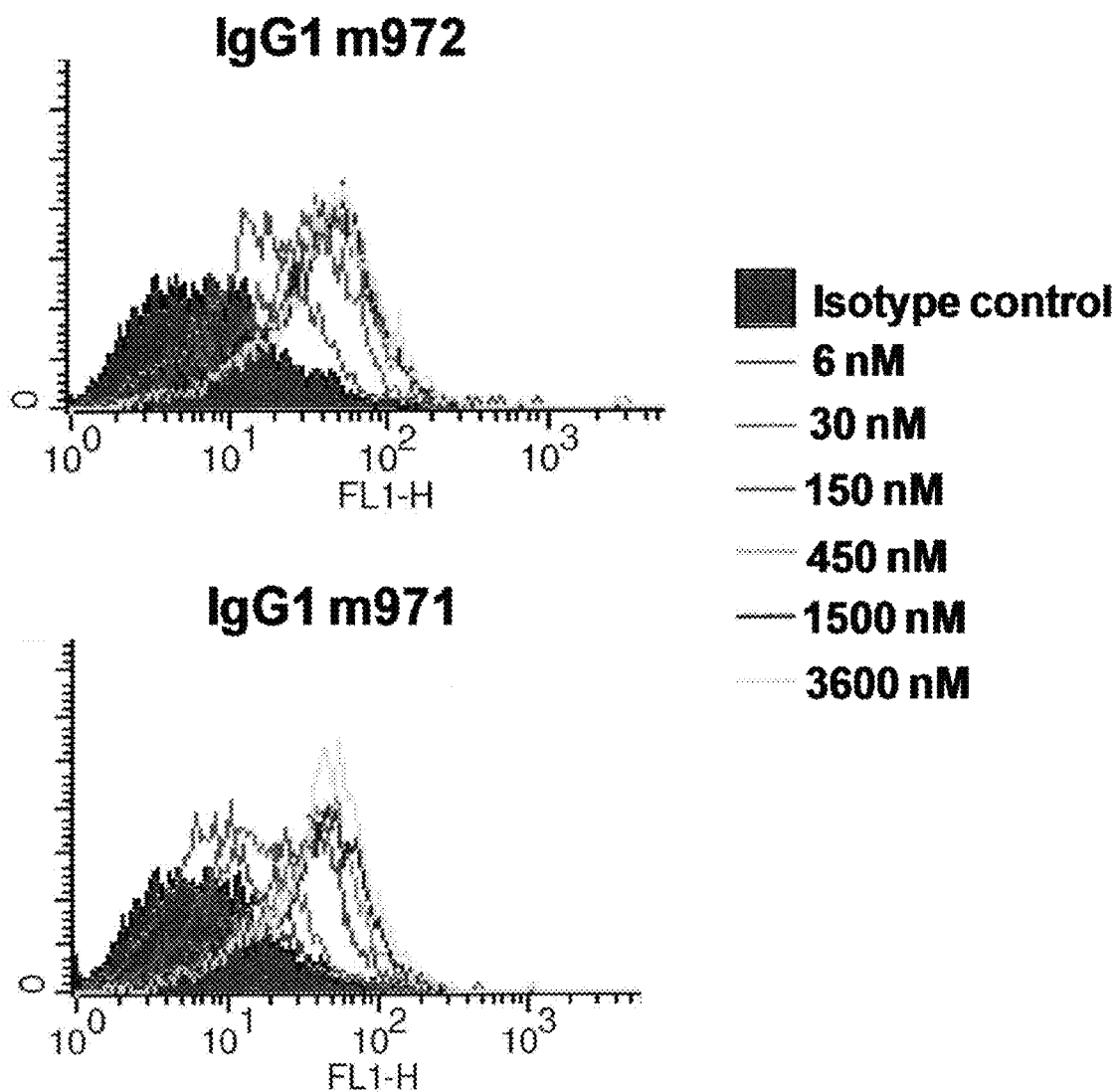
FIGS. 4A and 4B are a set of FACS plots and a line graph showing affinity determination of m971 and m972.
Figure 4B:
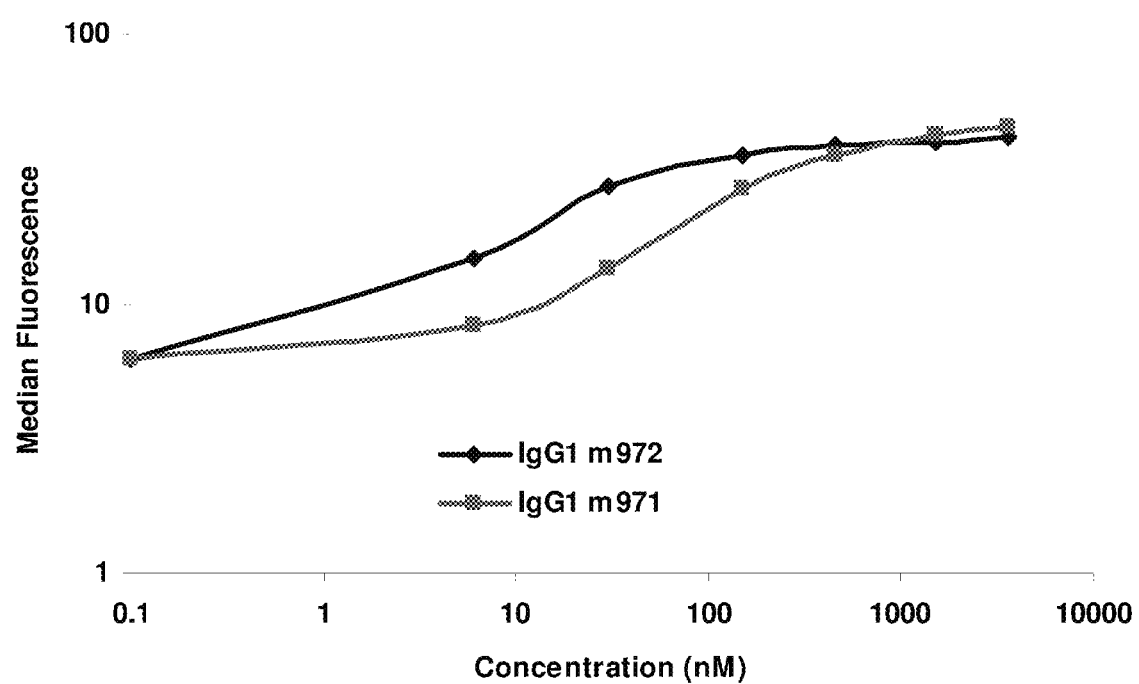

The binding characteristics of the two IgGs to cell surface-associated CD22 was further analyzed by using increasing concentrations of both IgGs against BJAB cells in a flow cytometry assay. It is evident that the binding of both IgGs to BJAB cells was saturable (FIG. 4A). This is another indication of specific binding. IgG1 m972 had an apparent affinity of approximately 15 nM, whereas m971 had an affinity of approximately 75 nM (FIG. 4B). This is in agreement with the flow cytometry data obtained with the other B cell lines showing better binding by m972. However, the affinities obtained through flow cytometry were lower than those obtained through ELISA. This suggests that differences exist between cell surface-associated CD22 and soluble CD22, despite the fact that soluble CD22 is a better representation than CD22-Fc of the cell surface associated CD22.

Finally, to assess the new antibodies' ability to down modulate cell-surface CD22, a flow cytometry assay with HA22 was performed on Raji cells with or without pretreatment with the new IgG1s. Compared to the efficient internalization and down modulation of cell surface CD22 by HA22 (Du et al., *Cancer Res.* 68:6300-6305, 2008), only slight down-modulation was detected by IgG1m972. There was a 15% down-modulation of the cell surface CD22 after a one hour incubation with 10 μg/ml of m972, whereas IgG1 m971 and an isotype control IgG1 had no effect under the same experimental conditions.

Example 2

CD22-Specific Monoclonal Antibodies for Detecting a B-Cell Malignancy in a Subject or Confirming the Diagnosis of a B-Cell Malignancy in a Subject This example describes the use of CD22-specific human monoclonal antibodies for the detection of a B-cell malignancy in a subject. This example further describes the use of these antibodies to confirm the diagnosis of a B-cell malignancy in a subject.

Levels of soluble CD22 are elevated in subjects with B-cell malignancies, relative to healthy subjects. Thus, detection and quantitation of sCD22 in patients diagnosed with, or suspected of having a B-cell malignancy, can be used to detect a B-cell malignancy or confirm the diagnosis of a B-cell malignancy in a subject. A blood sample is obtained from the patient diagnosed with, or suspected of having a B-cell malignancy. A blood sample taken from a patient that does not have a B-cell malignancy is used as a control.

In this example, a sandwich ELISA is performed to detect sCD22 in the blood samples. Human monoclonal anti-CD22 antibody is immobilized on the surface of a 96 well flat-bottomed plate by coating the plate with the antibody and incubating for 2 hours at room temperature. After washing the plate twice with 0.02% Tween PBS (T-PBS), the plate was blocked with 1% bovine serum albumin (BSA)-PBS to preclude nonspecific binding, then washed twice with T-PBS. The patient and control samples are added to the wells and incubated for approximately 15-20 hours. After washing with T-PBS three times, a second anti-CD22 antibody directly labeled with horseradish peroxidase (HRP) is added to the plate. After three more washes with T-PBS, 100 µl of 10,000-fold diluted Avidine-HRP solution (Biosource) is added and incubated 1 hour at room temperature. After three more washes with T-PBS, 100 µl of TMB solution (Pierce) and 100 µl of $H_2O_2$ are added and incubated for 5 minutes, followed by the addition of 100 µl of 2N $H_2SO_4$ to stop the color development. The levels of sCD22 are determined by measuring the OD value at 450 nm.

An increase in the level of sCD22 in the patient sample, relative to the control sample, indicates that the subject has a B-cell malignancy. Thus, detection of sCD22 can be used to detect a B-cell malignancy in a subject, or confirm the diagnosis of a B-cell malignancy in a subject.

Example 3

CD22-Specific Monoclonal Antibodies for the Treatment of B-Cell Malignancies

This example describes the use of CD22-specific human monoclonal antibodies for the treatment of B-cell malignancies that express CD22 (such as, for example, non-Hodgkin's lymphoma, Burkitt's lymphoma, small lymphocytic lymphoma, primary effusion lymphoma, diffuse large B-cell lymphoma, splenic marginal zone lymphoma, MALT lymphoma, hairy cell leukemia, chronic lymphocytic leukemia and B-cell prolymphocytic leukemia). Patients diagnosed with a B-cell malignancy can be treated according to standard procedures in the art (see, for example, U.S. Patent Application Publication No. 2006/0057136; DiJoseph et al., *Clin. Cancer Res.* 12(1):242-249, 2006; Kreitman et al., *N. Engl. J. Med.* 345(4):241-247, 2001; and Leonard et al., *Clin. Cancer Res.* 10:5327-5334, 2004).

In this example, patients diagnosed with a B-cell malignancy are administered an immunoconjugate comprising a CD22-specific human monoclonal antibody linked to *Pseudomonas* exotoxin (PE). Preparation of PE immunoconjugates has been described (see, for example, U.S. Pat. No. 7,081,518 and U.S. Patent Application Publication Nos. 2005/0214304, 2005/0118182 and 2007/0189962). The CD22 immunoconjugate is administered by intravenous infusion in four doses, one dose per week. The dose of immunoconjugate administered to a patient varies depending on the weight and gender of the patient, and mode and time course of administration. Following treatment, patients are evaluated for cancer progression and other clinical signs of illness.

This disclosure provides fully human monoclonal antibodies specific for CD22. The disclosure further provides methods of treating or detecting cancers associated with expression of human CD22. It will be apparent that the precise details of the methods described may be varied or modified without departing from the spirit of the described disclosure. We claim all such modifications and variations that fall within the scope and spirit of the claims below.

The invention claimed is:

1. A method of treating a CD22-expressing B-cell malignancy in a subject, comprising administering to the subject a therapeutically effective amount of a monoclonal antibody that specifically binds human CD22 and is conjugated to an agent that inhibits growth of malignant B cells or kills malignant B cells in the subject, the antibody comprising
   a heavy chain or portion thereof, which comprises an amino acid sequence comprising residues 26-35 of SEQ ID NO: 3, residues 53-61 of SEQ ID NO: 3 and residues 100-113 of SEQ ID NO: 3, and
   a light chain or portion thereof, which comprises an amino acid sequence comprising residues 27-32 of SEQ ID NO: 4, residues 50-52 of SEQ ID NO: 4 and residues 89-97 of SEQ ID NO: 4,
   wherein the therapeutically effective amount of the monoclonal antibody conjugated to the agent is an amount that inhibits growth of malignant B cells or kills malignant B cells in the subject,
   thereby treating the subject.

2. The method of claim 1, wherein the agent is a toxin.

3. The method of claim 2, wherein the toxin is a *Pseudomonas* exotoxin.

4. The method of claim 1, wherein the heavy chain or portion thereof comprises a variable heavy ($V_H$) region having the amino acid sequence of a VH region sequence present within SEQ ID NO: 3, or the light chain or portion thereof comprises a variable light ($V_L$) region having the amino acid sequence of a VL region sequence present within SEQ ID NO: 4, or both.

5. The method of claim 1, wherein the antibody comprises an Fab, scFv, or IgG antibody.

6. The method of claim 5, wherein the antibody comprises an scFv.

7. A method of treating a CD22-expressing B-cell malignancy in a subject, comprising administering to the subject a therapeutically effective amount of an immunoconjugate comprising a monoclonal antibody that specifically binds human CD22 and an effector molecule that inhibits growth of malignant B cells or kills malignant B cells in the subject, wherein the antibody comprises a heavy chain or portion thereof, which comprises an amino acid sequence comprising residues 26-35 of SEQ ID NO: 3, residues 53-61 of SEQ ID NO: 3 and residues 100-113 of SEQ ID NO: 3 and a light chain or portion thereof, which comprises an amino acid sequence comprising residues 27-32 of SEQ ID NO: 4, residues 50-52 of SEQ ID NO: 4 and residues 89-97 of SEQ ID NO: 4, wherein the therapeutically effective amount of the immunoconjugate is an amount sufficient to inhibit growth of malignant B cells or kill malignant B cells in the subject, thereby treating the subject.

8. The method of claim 7, wherein the effector molecule comprises a toxin.

9. The method of claim 7, wherein the heavy chain or portion thereof comprises a variable heavy ($V_H$) region having the amino acid sequence of a VH region sequence present within SEQ ID NO: 3, or the light chain or portion thereof comprises a variable light ($V_L$) region having the amino acid sequence of a VL region sequence present within SEQ ID NO: 4, or both.

10. The method of claim 7, wherein the antibody comprises an Fab, scFv, or IgG antibody.

11. The method of claim 10, wherein the antibody comprises an scFv.

12. A method of determining if a subject has a CD22-expressing B-cell malignancy, or confirming a diagnosis of a CD22-expressing B-cell malignancy in a subject, comprising:
- contacting a sample from the subject with a monoclonal antibody that specifically binds human CD22, the antibody comprising
- a heavy chain or portion thereof, which comprises an amino acid sequence comprising residues 26-35 of SEQ ID NO: 3, residues 53-61 of SEQ ID NO: 3 and residues 100-113 of SEQ ID NO: 3, and
- a light chain or portion thereof, which comprises an amino acid sequence comprising residues 27-32 of SEQ ID NO: 4, residues 50-52 of SEQ ID NO: 4 and residues 89-97 of SEQ ID NO: 4;
- detecting binding of the antibody to CD22 in the sample; and
- determining that the subject has a CD22-expressing B-cell malignancy, or confirming the diagnosis of the CD22-expressing B-cell malignancy in the subject, if an increase is detected in the binding of the antibody to CD22 in the sample as compared to binding of the antibody to a control sample.

13. The method of claim 12, wherein the monoclonal antibody is directly labeled.

* * * * *

SEQUENCE LISTING

<160> NUMBER OF SEQ ID NOS: 11

<210> SEQ ID NO 1
<211> LENGTH: 228
<212> TYPE: PRT
<213> ORGANISM: Artificial Sequence
<220> FEATURE:
<223> OTHER INFORMATION: Synthetic polypeptide

<400> SEQUENCE: 1

Glu Val Gln Leu Val Gln Ser Gly Gly Gly Val Val Arg Pro Gly Gly
1               5                   10                  15

Ser Leu Arg Leu Pro Cys Ala Ala Ser Gly Phe Thr Phe Asp Asp Tyr
            20                  25                  30

Gly Met Ser Trp Val Arg Gln Ala Pro Gly Lys Gly Leu Glu Trp Val
        35                  40                  45

Ser Gly Ile Asn Trp Asn Gly Gly Ser Thr Gly Tyr Ala Asp Ser Val
    50                  55                  60

Lys Gly Arg Phe Thr Ile Ser Arg Asp Asn Ala Lys Asn Ser Leu Tyr
65                  70                  75                  80

Leu Gln Met Asn Ser Leu Arg Ala Glu Asp Thr Ala Leu Tyr His Cys

```
                    85                  90                  95
Ala Arg Gly Gly Asp Asp Ala Phe Asp Ile Trp Gly Gln Gly Thr Met
                100                 105                 110

Val Thr Val Ser Ser Ala Ser Thr Lys Gly Pro Ser Val Phe Pro Leu
            115                 120                 125

Ala Pro Ser Ser Lys Ser Thr Ser Gly Gly Thr Ala Ala Leu Gly Cys
        130                 135                 140

Leu Val Lys Asp Tyr Phe Pro Glu Pro Val Thr Val Ser Trp Asn Ser
145                 150                 155                 160

Gly Ala Leu Thr Ser Gly Val His Thr Phe Pro Ala Val Leu Gln Ser
                165                 170                 175

Ser Gly Leu Tyr Ser Leu Ser Ser Val Val Thr Val Pro Ser Ser Ser
            180                 185                 190

Leu Gly Thr Gln Thr Tyr Ile Cys Asn Val Asn His Lys Pro Ser Asn
        195                 200                 205

Thr Lys Val Asp Lys Lys Val Glu Pro Lys Ser Cys Asp Lys Thr Ser
    210                 215                 220

Gly Gln Ala Gly
225

<210> SEQ ID NO 2
<211> LENGTH: 215
<212> TYPE: PRT
<213> ORGANISM: Artificial Sequence
<220> FEATURE:
<223> OTHER INFORMATION: Synthetic polypeptide

<400> SEQUENCE: 2

Arg Ile Val Met Thr Gln Ser Pro Gly Thr Leu Ser Val Ser Pro Gly
1               5                   10                  15

Glu Thr Ala Thr Leu Ser Cys Arg Ala Ser Gln Ser Phe Ser Asn Met
            20                  25                  30

Leu Ala Trp Tyr Gln Gln Lys Ser Gly Gln Pro Pro Arg Leu Leu Ile
        35                  40                  45

Tyr Gly Val Ser Thr Arg Ala Ala Gly Val Pro Ala Arg Phe Ser Gly
    50                  55                  60

Ser Gly Ser Gly Thr Glu Phe Thr Leu Thr Ile Ser Asn Leu Gln Ser
65                  70                  75                  80

Glu Asp Phe Ala Val Tyr Tyr Cys Gln Gln Tyr Gly Asp Trp Pro Arg
                85                  90                  95

Tyr Thr Phe Gly Gln Gly Thr Lys Val Glu Arg Lys Arg Thr Val Ala
                100                 105                 110

Ala Pro Ser Val Phe Ile Phe Pro Pro Ser Asp Glu Gln Leu Lys Ser
            115                 120                 125

Gly Thr Ala Ser Val Val Cys Leu Leu Asn Asn Phe Tyr Pro Arg Glu
        130                 135                 140

Ala Lys Val Gln Trp Lys Val Asp Asn Ala Leu Gln Ser Gly Asn Ser
145                 150                 155                 160

Gln Glu Ser Val Thr Glu Gln Asp Ser Lys Asp Ser Thr Tyr Ser Leu
                165                 170                 175

Ser Ser Thr Leu Thr Leu Ser Lys Ala Asp Tyr Glu Lys His Lys Val
            180                 185                 190

Tyr Ala Cys Glu Val Thr His Gln Gly Leu Ser Ser Pro Val Thr Lys
        195                 200                 205

Ser Phe Asn Arg Gly Glu Cys
```

<210> SEQ ID NO 3
<211> LENGTH: 235
<212> TYPE: PRT
<213> ORGANISM: Artificial Sequence
<220> FEATURE:
<223> OTHER INFORMATION: Synthetic polypeptide

<400> SEQUENCE: 3

```
Gln Val Gln Leu Gln Gln Ser Gly Pro Gly Leu Val Lys Pro Ser Gln
1               5                   10                  15

Thr Leu Ser Leu Thr Cys Ala Ile Ser Gly Asp Ser Val Ser Ser Asn
            20                  25                  30

Ser Ala Ala Trp Asn Trp Ile Arg Gln Ser Pro Ser Arg Gly Leu Glu
        35                  40                  45

Trp Leu Gly Arg Thr Tyr Tyr Arg Ser Lys Trp Tyr Asn Asp Tyr Ala
    50                  55                  60

Val Ser Val Lys Ser Arg Ile Thr Ile Asn Pro Asp Thr Ser Lys Asn
65                  70                  75                  80

Gln Phe Ser Leu Gln Leu Asn Ser Val Thr Pro Glu Asp Thr Ala Val
                85                  90                  95

Tyr Tyr Cys Ala Arg Glu Val Thr Gly Asp Leu Glu Asp Ala Phe Asp
            100                 105                 110

Ile Trp Gly Gln Gly Thr Met Val Thr Val Ser Ser Ala Ser Thr Lys
        115                 120                 125

Gly Pro Ser Val Phe Pro Leu Ala Pro Ser Ser Lys Ser Thr Ser Gly
    130                 135                 140

Gly Thr Ala Ala Leu Gly Cys Leu Val Lys Asp Tyr Phe Pro Glu Pro
145                 150                 155                 160

Val Thr Val Ser Trp Asn Ser Gly Ala Leu Thr Ser Gly Val His Thr
                165                 170                 175

Phe Pro Ala Val Leu Gln Ser Ser Gly Leu Tyr Ser Leu Ser Ser Val
            180                 185                 190

Val Thr Val Pro Ser Ser Ser Leu Gly Thr Gln Thr Tyr Ile Cys Asn
        195                 200                 205

Val Ser His Lys Pro Ser Asn Thr Lys Val Asp Lys Lys Val Glu Pro
    210                 215                 220

Lys Ser Cys Asp Lys Thr Ser Gly Gln Ala Gly
225                 230                 235
```

<210> SEQ ID NO 4
<211> LENGTH: 214
<212> TYPE: PRT
<213> ORGANISM: Artificial Sequence
<220> FEATURE:
<223> OTHER INFORMATION: Synthetic polypeptide

<400> SEQUENCE: 4

```
Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Thr Ile Trp Ser Tyr
            20                  25                  30

Leu Asn Trp Tyr Gln Gln Arg Pro Gly Lys Ala Pro Asn Leu Leu Ile
        35                  40                  45

Tyr Ala Ala Ser Ser Leu Gln Ser Gly Val Pro Ser Arg Phe Ser Gly
    50                  55                  60
```

```
Arg Gly Ser Gly Thr Asp Phe Thr Leu Thr Ile Ser Ser Leu Gln Ala
 65                  70                  75                  80

Glu Asp Phe Ala Thr Tyr Tyr Cys Gln Gln Ser Tyr Ser Ile Pro Gln
                 85                  90                  95

Thr Phe Gly Gln Gly Thr Lys Leu Glu Ile Lys Arg Thr Val Ala Ala
            100                 105                 110

Pro Ser Val Phe Ile Phe Pro Pro Ser Asp Glu Gln Leu Lys Ser Gly
        115                 120                 125

Thr Ala Ser Val Val Cys Leu Leu Asn Asn Phe Tyr Pro Arg Glu Ala
    130                 135                 140

Lys Val Gln Trp Lys Val Asp Asn Ala Leu Gln Ser Gly Asn Ser Gln
145                 150                 155                 160

Glu Ser Val Thr Glu Gln Asp Ser Lys Asp Ser Thr Tyr Ser Leu Ser
                165                 170                 175

Ser Thr Leu Thr Leu Ser Lys Ala Asp Tyr Glu Lys His Lys Val Tyr
            180                 185                 190

Ala Cys Glu Val Thr His Gln Gly Leu Ser Ser Pro Val Thr Lys Ser
        195                 200                 205

Phe Asn Arg Gly Glu Cys
    210

<210> SEQ ID NO 5
<211> LENGTH: 3293
<212> TYPE: DNA
<213> ORGANISM: Homo sapiens
<220> FEATURE:
<221> NAME/KEY: CDS
<222> LOCATION: (78)..(2621)

<400> SEQUENCE: 5
cttttgctct cagatgctgc cagggtccct gaagagggaa gacacgcgga aacaggcttg    60
cacccagaca cgacacc atg cat ctc ctc ggc ccc tgg ctc ctg ctc ctg       110
                   Met His Leu Leu Gly Pro Trp Leu Leu Leu Leu
                     1               5                  10 gtt cta gaa tac ttg gct ttc tct gac tca agt aaa tgg gtt ttt gag     158
Val Leu Glu Tyr Leu Ala Phe Ser Asp Ser Ser Lys Trp Val Phe Glu
             15                  20                  25 cac cct gaa acc ctc tac gcc tgg gag ggg gcc tgc gtc tgg atc ccc     206
His Pro Glu Thr Leu Tyr Ala Trp Glu Gly Ala Cys Val Trp Ile Pro
         30                  35                  40 tgc acc tac aga gcc cta gat ggt gac ctg gaa agc ttc atc ctg ttc     254
Cys Thr Tyr Arg Ala Leu Asp Gly Asp Leu Glu Ser Phe Ile Leu Phe
     45                  50                  55 cac aat cct gag tat aac aag aac acc tcg aag ttt gat ggg aca aga     302
His Asn Pro Glu Tyr Asn Lys Asn Thr Ser Lys Phe Asp Gly Thr Arg
 60                  65                  70                  75 ctc tat gaa agc aca aag gat ggg aag gtt cct tct gag cag aaa agg     350
Leu Tyr Glu Ser Thr Lys Asp Gly Lys Val Pro Ser Glu Gln Lys Arg
                 80                  85                  90 gtg caa ttc ctg gga gac aag aat aag aac tgc aca ctg agt atc cac     398
Val Gln Phe Leu Gly Asp Lys Asn Lys Asn Cys Thr Leu Ser Ile His
             95                 100                 105 ccg gtg cac ctc aat gac agt ggt cag ctg ggg ctg agg atg gag tcc     446
Pro Val His Leu Asn Asp Ser Gly Gln Leu Gly Leu Arg Met Glu Ser
        110                 115                 120 aag act gag aaa tgg atg gaa cga ata cac ctc aat gtc tct gaa agg     494
Lys Thr Glu Lys Trp Met Glu Arg Ile His Leu Asn Val Ser Glu Arg
    125                 130                 135
```

```
cct ttt cca cct cat atc cag ctc cct cca gaa att caa gag tcc cag      542
Pro Phe Pro Pro His Ile Gln Leu Pro Pro Glu Ile Gln Glu Ser Gln
140             145                 150                 155 gaa gtc act ctg acc tgc ttg ctg aat ttc tcc tgc tat ggg tat ccg      590
Glu Val Thr Leu Thr Cys Leu Leu Asn Phe Ser Cys Tyr Gly Tyr Pro
                160                 165                 170 atc caa ttg cag tgg ctc cta gag ggg gtt cca atg agg cag gct gct      638
Ile Gln Leu Gln Trp Leu Leu Glu Gly Val Pro Met Arg Gln Ala Ala
            175                 180                 185 gtc acc tcg acc tcc ttg acc atc aag tct gtc ttc acc cgg agc gag      686
Val Thr Ser Thr Ser Leu Thr Ile Lys Ser Val Phe Thr Arg Ser Glu
        190                 195                 200 ctc aag ttc tcc cca cag tgg agt cac cat ggg aag att gtg acc tgc      734
Leu Lys Phe Ser Pro Gln Trp Ser His His Gly Lys Ile Val Thr Cys
    205                 210                 215 cag ctt cag gat gca gat ggg aag ttc ctc tcc aat gac acg gtg cag      782
Gln Leu Gln Asp Ala Asp Gly Lys Phe Leu Ser Asn Asp Thr Val Gln
220                 225                 230                 235 ctg aac gtg aag cac acc ccg aag ttg gag atc aag gtc act ccc agt      830
Leu Asn Val Lys His Thr Pro Lys Leu Glu Ile Lys Val Thr Pro Ser
                240                 245                 250 gat gcc ata gtg agg gag ggg gac tct gtg acc atg acc tgc gag gtc      878
Asp Ala Ile Val Arg Glu Gly Asp Ser Val Thr Met Thr Cys Glu Val
            255                 260                 265 agc agc agc aac ccg gag tac acg acg gta tcc tgg ctc aag gat ggg      926
Ser Ser Ser Asn Pro Glu Tyr Thr Thr Val Ser Trp Leu Lys Asp Gly
        270                 275                 280 acc tcg ctg aag aag cag aat aca ttc acg cta aac ctg cgc gaa gtg      974
Thr Ser Leu Lys Lys Gln Asn Thr Phe Thr Leu Asn Leu Arg Glu Val
    285                 290                 295 acc aag gac cag agt ggg aag tac tgc tgt cag gtc tcc aat gac gtg     1022
Thr Lys Asp Gln Ser Gly Lys Tyr Cys Cys Gln Val Ser Asn Asp Val
300                 305                 310                 315 ggc ccg gga agg tcg gaa gaa gtg ttc ctg caa gtg cag tat gcc ccg     1070
Gly Pro Gly Arg Ser Glu Glu Val Phe Leu Gln Val Gln Tyr Ala Pro
                320                 325                 330 gaa cct tcc acg gtt cag atc ctc cac tca ccg gct gtg gag gga agt     1118
Glu Pro Ser Thr Val Gln Ile Leu His Ser Pro Ala Val Glu Gly Ser
            335                 340                 345 caa gtc gag ttt ctt tgc atg tca ctg gcc aat cct ctt cca aca aat     1166
Gln Val Glu Phe Leu Cys Met Ser Leu Ala Asn Pro Leu Pro Thr Asn
        350                 355                 360 tac acg tgg tac cac aat ggg aaa gaa atg cag gga agg aca gag gag     1214
Tyr Thr Trp Tyr His Asn Gly Lys Glu Met Gln Gly Arg Thr Glu Glu
    365                 370                 375 aaa gtc cac atc cca aag atc ctc ccc tgg cac gct ggg act tat tcc     1262
Lys Val His Ile Pro Lys Ile Leu Pro Trp His Ala Gly Thr Tyr Ser
380                 385                 390                 395 tgt gtg gca gaa aac att ctt ggt act gga cag agg ggc ccg gga gct     1310
Cys Val Ala Glu Asn Ile Leu Gly Thr Gly Gln Arg Gly Pro Gly Ala
                400                 405                 410 gag ctg gat gtc cag tat cct ccc aag aag gtg acc aca gtg att caa     1358
Glu Leu Asp Val Gln Tyr Pro Pro Lys Lys Val Thr Thr Val Ile Gln
            415                 420                 425 aac ccc atg ccg att cga gaa gga gac aca gtg acc ctt tcc tgt aac     1406
Asn Pro Met Pro Ile Arg Glu Gly Asp Thr Val Thr Leu Ser Cys Asn
        430                 435                 440 tac aat tcc agt aac ccc agt gtt acc cgg tat gaa tgg aaa ccc cat     1454
Tyr Asn Ser Ser Asn Pro Ser Val Thr Arg Tyr Glu Trp Lys Pro His
    445                 450                 455
```

-continued

```
ggc gcc tgg gag gag cca tcg ctt ggg gtg ctg aag atc caa aac gtt    1502
Gly Ala Trp Glu Glu Pro Ser Leu Gly Val Leu Lys Ile Gln Asn Val
460             465                 470                 475 ggc tgg gac aac aca acc atc gcc tgc gca gct tgt aat agt tgg tgc    1550
Gly Trp Asp Asn Thr Thr Ile Ala Cys Ala Ala Cys Asn Ser Trp Cys
                480                 485                 490 tcg tgg gcc tcc cct gtc gcc ctg aat gtc cag tat gcc ccc cga gac    1598
Ser Trp Ala Ser Pro Val Ala Leu Asn Val Gln Tyr Ala Pro Arg Asp
                    495                 500                 505 gtg agg gtc cgg aaa atc aag ccc ctt tcc gag att cac tct gga aac    1646
Val Arg Val Arg Lys Ile Lys Pro Leu Ser Glu Ile His Ser Gly Asn
                510                 515                 520 tcg gtc agc ctc caa tgt gac ttc tca agc agc cac ccc aaa gaa gtc    1694
Ser Val Ser Leu Gln Cys Asp Phe Ser Ser Ser His Pro Lys Glu Val
                525                 530                 535 cag ttc ttc tgg gag aaa aat ggc agg ctt ctg ggg aaa gaa agc cag    1742
Gln Phe Phe Trp Glu Lys Asn Gly Arg Leu Leu Gly Lys Glu Ser Gln
540             545                 550                 555 ctg aat ttt gac tcc atc tcc cca gaa gat gct ggg agt tac agc tgc    1790
Leu Asn Phe Asp Ser Ile Ser Pro Glu Asp Ala Gly Ser Tyr Ser Cys
                    560                 565                 570 tgg gtg aac aac tcc ata gga cag aca gcg tcc aag gcc tgg aca ctt    1838
Trp Val Asn Asn Ser Ile Gly Gln Thr Ala Ser Lys Ala Trp Thr Leu
                575                 580                 585 gaa gtg ctg tat gca ccc agg agg ctg cgt gtg tcc atg agc ccg ggg    1886
Glu Val Leu Tyr Ala Pro Arg Arg Leu Arg Val Ser Met Ser Pro Gly
                590                 595                 600 gac caa gtg atg gag ggg aag agt gca acc ctg acc tgt gag agc gac    1934
Asp Gln Val Met Glu Gly Lys Ser Ala Thr Leu Thr Cys Glu Ser Asp
                605                 610                 615 gcc aac cct ccc gtc tcc cac tac acc tgg ttt gac tgg aat aac caa    1982
Ala Asn Pro Pro Val Ser His Tyr Thr Trp Phe Asp Trp Asn Asn Gln
620             625                 630                 635 agc ctc ccc tac cac agc cag aag ctg aga ttg gag ccg gtg aag gtc    2030
Ser Leu Pro Tyr His Ser Gln Lys Leu Arg Leu Glu Pro Val Lys Val
                640                 645                 650 cag cac tcg ggt gcc tac tgg tgc cag ggg acc aac agt gtg ggc aag    2078
Gln His Ser Gly Ala Tyr Trp Cys Gln Gly Thr Asn Ser Val Gly Lys
                655                 660                 665 ggc cgt tcg cct ctc agc acc ctc acc gtc tac tat agc ccg gag acc    2126
Gly Arg Ser Pro Leu Ser Thr Leu Thr Val Tyr Tyr Ser Pro Glu Thr
                670                 675                 680 atc ggc agg cga gtg gct gtg gga ctc ggg tcc tgc ctc gcc atc ctc    2174
Ile Gly Arg Arg Val Ala Val Gly Leu Gly Ser Cys Leu Ala Ile Leu
                685                 690                 695 atc ctg gca atc tgt ggg ctc aag ctc cag cga cgt tgg aag agg aca    2222
Ile Leu Ala Ile Cys Gly Leu Lys Leu Gln Arg Arg Trp Lys Arg Thr
700             705                 710                 715 cag agc cag cag ggg ctt cag gag aat tcc agc ggc cag agc ttc ttt    2270
Gln Ser Gln Gln Gly Leu Gln Glu Asn Ser Ser Gly Gln Ser Phe Phe
                720                 725                 730 gtg agg aat aaa aag gtt aga agg gcc ccc ctc tct gaa ggc ccc cac    2318
Val Arg Asn Lys Lys Val Arg Arg Ala Pro Leu Ser Glu Gly Pro His
                735                 740                 745 tcc ctg gga tgc tac aat cca atg atg gaa gat ggc att agc tac acc    2366
Ser Leu Gly Cys Tyr Asn Pro Met Met Glu Asp Gly Ile Ser Tyr Thr
                750                 755                 760 acc ctg cgc ttt ccc gag atg aac ata cca cga act gga gat gca gag    2414
Thr Leu Arg Phe Pro Glu Met Asn Ile Pro Arg Thr Gly Asp Ala Glu
```

-continued

```
              765                 770                 775
tcc tca gag atg cag aga cct ccc ccg gac tgc gat gac acg gtc act   2462
Ser Ser Glu Met Gln Arg Pro Pro Pro Asp Cys Asp Asp Thr Val Thr
780                 785                 790                 795 tat tca gca ttg cac aag cgc caa gtg ggc gac tat gag aac gtc att   2510
Tyr Ser Ala Leu His Lys Arg Gln Val Gly Asp Tyr Glu Asn Val Ile
                800                 805                 810 cca gat ttt cca gaa gat gag ggg att cat tac tca gag ctg atc cag   2558
Pro Asp Phe Pro Glu Asp Glu Gly Ile His Tyr Ser Glu Leu Ile Gln
            815                 820                 825 ttt ggg gtc ggg gag cgg cct cag gca caa gaa aat gtg gac tat gtg   2606
Phe Gly Val Gly Glu Arg Pro Gln Ala Gln Glu Asn Val Asp Tyr Val
        830                 835                 840 atc ctc aaa cat tga cactggatgg gctgcagcag aggcactggg ggcagcgggg   2661
Ile Leu Lys His
    845 gccagggaag tccccgagtt tccccagaca ccgccacatg gcttcctcct gcgcgcatgt   2721 gcgcacacac acacacacac gcacacacac acacacacac tcactgcgga gaaccttgtg   2781 cctggctcag agccagtctt tttggtgagg gtaaccccaa acctccaaaa ctcctgcccc   2841 tgttctcttc cactctcctt gctacccaga atccatcta aatacctgcc ctgacatgca   2901 cacctccccc tgcccccacc acggccactg gcatctcca ccccagctg cttgtgtccc   2961 tcctgggatc tgctcgtcat cattttttcct tcccttctcc atctctctgg ccctctaccc   3021 ctgatctgac atccccactc acgaatatta tgcccagttt ctgcctctga gggaaagccc   3081 agaaaaggac agaaacgaag tagaaagggg cccagtcctg gcctggcttc tcctttggaa   3141 gtgaggcatt gcacggggag acgtacgtat cagcggcccc ttgactctgg ggactccggg   3201 tttgagatgg acacactggt gtggattaac ctgccaggga gacagagctc acaataaaaa   3261 tggctcagat gccacttcaa agaaaaaaaa aa                                3293

<210> SEQ ID NO 6
<211> LENGTH: 847
<212> TYPE: PRT
<213> ORGANISM: Homo sapiens

<400> SEQUENCE: 6

Met His Leu Leu Gly Pro Trp Leu Leu Leu Val Leu Glu Tyr Leu
1               5                   10                  15

Ala Phe Ser Asp Ser Ser Lys Trp Val Phe Glu His Pro Glu Thr Leu
                20                  25                  30

Tyr Ala Trp Glu Gly Ala Cys Val Trp Ile Pro Cys Thr Tyr Arg Ala
            35                  40                  45

Leu Asp Gly Asp Leu Glu Ser Phe Ile Leu Phe His Asn Pro Glu Tyr
        50                  55                  60

Asn Lys Asn Thr Ser Lys Phe Asp Gly Thr Arg Leu Tyr Glu Ser Thr
65                  70                  75                  80

Lys Asp Gly Lys Val Pro Ser Glu Gln Lys Arg Val Gln Phe Leu Gly
                85                  90                  95

Asp Lys Asn Lys Asn Cys Thr Leu Ser Ile His Pro Val His Leu Asn
            100                 105                 110

Asp Ser Gly Gln Leu Gly Leu Arg Met Glu Ser Lys Thr Glu Lys Trp
        115                 120                 125

Met Glu Arg Ile His Leu Asn Val Ser Glu Arg Pro Phe Pro Pro His
    130                 135                 140
```

-continued

```
Ile Gln Leu Pro Pro Glu Ile Gln Glu Ser Gln Val Thr Leu Thr
145                 150                 155                 160

Cys Leu Leu Asn Phe Ser Cys Tyr Gly Tyr Pro Ile Gln Leu Gln Trp
                165                 170                 175

Leu Leu Glu Gly Val Pro Met Arg Gln Ala Ala Val Thr Ser Thr Ser
            180                 185                 190

Leu Thr Ile Lys Ser Val Phe Thr Arg Ser Glu Leu Lys Phe Ser Pro
        195                 200                 205

Gln Trp Ser His His Gly Lys Ile Val Thr Cys Gln Leu Gln Asp Ala
210                 215                 220

Asp Gly Lys Phe Leu Ser Asn Asp Thr Val Gln Leu Asn Val Lys His
225                 230                 235                 240

Thr Pro Lys Leu Glu Ile Lys Val Thr Pro Ser Asp Ala Ile Val Arg
                245                 250                 255

Glu Gly Asp Ser Val Thr Met Thr Cys Glu Val Ser Ser Ser Asn Pro
            260                 265                 270

Glu Tyr Thr Thr Val Ser Trp Leu Lys Asp Gly Thr Ser Leu Lys Lys
        275                 280                 285

Gln Asn Thr Phe Thr Leu Asn Leu Arg Glu Val Thr Lys Asp Gln Ser
290                 295                 300

Gly Lys Tyr Cys Cys Gln Val Ser Asn Asp Val Gly Pro Gly Arg Ser
305                 310                 315                 320

Glu Glu Val Phe Leu Gln Val Gln Tyr Ala Pro Glu Pro Ser Thr Val
                325                 330                 335

Gln Ile Leu His Ser Pro Ala Val Glu Gly Ser Gln Val Glu Phe Leu
            340                 345                 350

Cys Met Ser Leu Ala Asn Pro Leu Pro Thr Asn Tyr Thr Trp Tyr His
        355                 360                 365

Asn Gly Lys Glu Met Gln Gly Arg Thr Glu Glu Lys Val His Ile Pro
370                 375                 380

Lys Ile Leu Pro Trp His Ala Gly Thr Tyr Ser Cys Val Ala Glu Asn
385                 390                 395                 400

Ile Leu Gly Thr Gly Gln Arg Gly Pro Gly Ala Glu Leu Asp Val Gln
                405                 410                 415

Tyr Pro Pro Lys Lys Val Thr Thr Val Ile Gln Asn Pro Met Pro Ile
            420                 425                 430

Arg Glu Gly Asp Thr Val Thr Leu Ser Cys Asn Tyr Asn Ser Ser Asn
        435                 440                 445

Pro Ser Val Thr Arg Tyr Glu Trp Lys Pro His Gly Ala Trp Glu Glu
450                 455                 460

Pro Ser Leu Gly Val Leu Lys Ile Gln Asn Val Gly Trp Asp Asn Thr
465                 470                 475                 480

Thr Ile Ala Cys Ala Ala Cys Asn Ser Trp Cys Ser Trp Ala Ser Pro
                485                 490                 495

Val Ala Leu Asn Val Gln Tyr Ala Pro Arg Asp Val Arg Val Arg Lys
            500                 505                 510

Ile Lys Pro Leu Ser Glu Ile His Ser Gly Asn Ser Val Ser Leu Gln
        515                 520                 525

Cys Asp Phe Ser Ser Ser His Pro Lys Glu Val Gln Phe Phe Trp Glu
530                 535                 540

Lys Asn Gly Arg Leu Leu Gly Lys Glu Ser Gln Leu Asn Phe Asp Ser
545                 550                 555                 560

Ile Ser Pro Glu Asp Ala Gly Ser Tyr Ser Cys Trp Val Asn Asn Ser
```

```
                565                 570                 575
Ile Gly Gln Thr Ala Ser Lys Ala Trp Thr Leu Glu Val Leu Tyr Ala
            580                 585                 590

Pro Arg Arg Leu Arg Val Ser Met Ser Pro Gly Asp Gln Val Met Glu
        595                 600                 605

Gly Lys Ser Ala Thr Leu Thr Cys Glu Ser Asp Ala Asn Pro Pro Val
    610                 615                 620

Ser His Tyr Thr Trp Phe Asp Trp Asn Asn Gln Ser Leu Pro Tyr His
625                 630                 635                 640

Ser Gln Lys Leu Arg Leu Glu Pro Val Lys Val Gln His Ser Gly Ala
                645                 650                 655

Tyr Trp Cys Gln Gly Thr Asn Ser Val Gly Lys Gly Arg Ser Pro Leu
            660                 665                 670

Ser Thr Leu Thr Val Tyr Tyr Ser Pro Glu Thr Ile Gly Arg Arg Val
        675                 680                 685

Ala Val Gly Leu Gly Ser Cys Leu Ala Ile Leu Ile Leu Ala Ile Cys
    690                 695                 700

Gly Leu Lys Leu Gln Arg Arg Trp Lys Arg Thr Gln Ser Gln Gln Gly
705                 710                 715                 720

Leu Gln Glu Asn Ser Ser Gly Gln Ser Phe Phe Val Arg Asn Lys Lys
                725                 730                 735

Val Arg Arg Ala Pro Leu Ser Glu Gly Pro His Ser Leu Gly Cys Tyr
            740                 745                 750

Asn Pro Met Met Glu Asp Gly Ile Ser Tyr Thr Thr Leu Arg Phe Pro
        755                 760                 765

Glu Met Asn Ile Pro Arg Thr Gly Asp Ala Glu Ser Ser Glu Met Gln
    770                 775                 780

Arg Pro Pro Pro Asp Cys Asp Asp Thr Val Thr Tyr Ser Ala Leu His
785                 790                 795                 800

Lys Arg Gln Val Gly Asp Tyr Glu Asn Val Ile Pro Asp Phe Pro Glu
                805                 810                 815

Asp Glu Gly Ile His Tyr Ser Glu Leu Ile Gln Phe Gly Val Gly Glu
            820                 825                 830

Arg Pro Gln Ala Gln Glu Asn Val Asp Tyr Val Ile Leu Lys His
        835                 840                 845

<210> SEQ ID NO 7
<211> LENGTH: 675
<212> TYPE: DNA
<213> ORGANISM: Artificial Sequence
<220> FEATURE:
<223> OTHER INFORMATION: Synthetic polynucleotide

<400> SEQUENCE: 7
gaagtgcagc tggtgcagtc tgggggaggt gtggtacggc ctggggggtc cctgagactc      60
ccctgtgcag cctctggatt cacctttgat gattatggca tgagctgggt ccgccaagct     120
ccagggaagg ggctggagtg ggtctctggt attaattgga atggtggtag cacaggttat     180
gcagactctg tgaagggccg attcaccatc tccagagaca acgccaagaa ctccctgtat     240
ctgcaaatga acagtctgag agccgaggac acggccttgt atcactgtgc gagagggggt     300
gactacgacg ctttgatat ctggggccaa gggacaatgg tcaccgtctc ctcagcctcc     360
accaagggcc catcggtctt ccccctggca ccctcctcca agagcacctc tgggggcaca     420
gcggccctgg gctgcctggt caaggactac ttccccgaac cggtgacggt gtcgtggaac     480
```

```
tcaggcgccc tgaccagcgg cgtgcacacc ttcccggctg tcctacagtc ctcaggactc      540
tactccctca gcagcgtggt gaccgtgccc tccagcagct ggggcaccca gacctacatc      600
tgcaacgtga atcacaagcc cagcaacacc aaggtggaca gaaagttga gcccaaatct      660 tgtgacaaaa ctagt                                                       675

<210> SEQ ID NO 8
<211> LENGTH: 645
<212> TYPE: DNA
<213> ORGANISM: Artificial Sequence
<220> FEATURE:
<223> OTHER INFORMATION: Synthetic polynucleotide

<400> SEQUENCE: 8
cgaattgtga tgacgcagtc tccaggcacc ctgtctgtgt ctccggggga aacagccacc       60
ctctcctgca gggccagtca gagttttagc aacatgttag cctggtatca acagaaatct      120
ggccagcctc ccaggctcct catctatggt gtgtccacca gggccgctgg tgtcccagcc      180
aggttcagtg gcagcgggtc tgggacagag ttcactctca ccatcagcaa cctgcagtct      240
gaggattttg cagtttatta ctgtcagcag tatggtgact ggccccggta cacttttggc      300
caggggacca aggtggagag gaaacgaact gtggctgcac catctgtctt catcttcccg      360
ccatctgatg agcagttgaa atctggaact gcctctgttg tgtgcctgct gaataacttc      420
tatcccagag aggccaaagt acagtggaag gtggataacg ccctccaatc gggtaactcc      480
caggagagtg tcacagagca ggacagcaag gacagcacct acagcctcag cagcaccctg      540
acgctgagca agcagacta cgagaaacac aaagtctacg cctgcgaagt cacccatcag      600
ggcctgagct cgcccgtcac aaagagcttc aacaggggag agtgt                      645

<210> SEQ ID NO 9
<211> LENGTH: 693
<212> TYPE: DNA
<213> ORGANISM: Artificial Sequence
<220> FEATURE:
<223> OTHER INFORMATION: Synthetic polynucleotide

<400> SEQUENCE: 9
caggtacagc tgcagcagtc aggtccagga ctggtgaagc cctcgcagac cctctcactc       60
acctgtgcca tctccgggga cagtgtctct agcaacagtg ctgcttggaa ctggatcagg      120
cagtccccat cgagaggcct tgagtggctg ggaaggacat actacaggtc caagtggtat      180
aatgattatg cagtatctgt gaaaagtcga ataaccatca cccagacac atccaagaac      240 cagttctccc tgcagctgaa ctctgtgact cccgaggaca cggctgtgta ttactgtgca      300
agagaagtga ctggggatct cgaggatgct tttgatatct ggggccaagg acaatggtc      360 accgtctcct cagcctccac caagggccca tcggtcttcc ccctggcacc ctcctccaag      420
agcacctctg ggggcacagc ggccctgggc tgcctggtca aggactactt ccccgaaccg      480
gtgacggtgt cgtggaactc aggcgccctg accagcggcg tgcacacctt cccggctgtc      540
ctacagtcct caggactcta ctccctcagc agcgtggtga ccgtgccctc cagcagcttg      600
ggcacccaga cctacatctg caacgtgagt cacaagccca gcaacaccaa ggtggacaag      660
aaagttgagc ccaaatcttg tgacaaaact agt                                   693

<210> SEQ ID NO 10
<211> LENGTH: 642
<212> TYPE: DNA
<213> ORGANISM: Artificial Sequence
```

```
<220> FEATURE:
<223> OTHER INFORMATION: Synthetic polynucleotide

<400> SEQUENCE: 10
gacatccaga tgacccagtc tccatcgtcc ctgtctgcat ctgtaggaga cagagtcacc        60
atcacttgcc gggcaagcca gaccatttgg agctacttaa attggtatca gcagagacca      120
gggaaagccc ctaacctcct gatctatgct gcatccagtt tgcaaagtgg ggtcccatca      180
aggttcagtg gcaggggatc tgggacagat ttcactctca ccatcagcag tctgcaagct      240
gaagattttg caacttacta ctgtcaacag agttacagta tccctcagac ttttggccag      300
gggaccaagc tggagatcaa acgaactgtg gctgcaccat ctgtcttcat cttcccgcca      360
tctgatgagc agttgaaatc tggaactgcc tctgttgtgt gcctgctgaa taacttctat      420
cccagagagg ccaaagtaca gtggaaggtg gataacgccc tccaatcggg taactcccag      480
gagagtgtca cagagcagga cagcaaggac agcacctaca gcctcagcag caccctgacg      540
ctgagcaaag cagactacga gaaacacaaa gtctacgcct gcgaagtcac ccatcagggc      600
ctgagctcgc ccgtcacaaa gagcttcaac aggggagagt gt                         642

<210> SEQ ID NO 11
<211> LENGTH: 5
<212> TYPE: PRT
<213> ORGANISM: Artificial Sequence
<220> FEATURE:
<223> OTHER INFORMATION: Synthetic polypeptide

<400> SEQUENCE: 11

Gly Gly Gly Gly Ser
1               5
```